US012673975B2

(12) United States Patent
Minami

(10) Patent No.: US 12,673,975 B2
(45) Date of Patent: Jul. 7, 2026

(54) CYCLIC PEPTIDE, CELL SCAFFOLD MATERIAL, CELL SEPARATING MATERIAL, AND MEDIUM

(71) Applicant: FUJIFILM Corporation, Tokyo (JP)

(72) Inventor: Koichi Minami, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 882 days.

(21) Appl. No.: 17/643,533

(22) Filed: Dec. 9, 2021

(65) Prior Publication Data

US 2022/0089647 A1 Mar. 24, 2022

Related U.S. Application Data

(63) Continuation of application No. PCT/JP2020/022558, filed on Jun. 8, 2020.

(30) Foreign Application Priority Data

Jun. 11, 2019 (JP) ................................ 2019-108962

(51) Int. Cl.

*C07K 7/64* (2006.01)
*C07K 7/60* (2006.01)
*C12N 1/02* (2006.01)
*C12N 5/074* (2010.01)

(52) U.S. Cl.

CPC .................. *C07K 7/64* (2013.01); *C07K 7/60* (2013.01); *C12N 1/02* (2013.01); *C12N 5/0696* (2013.01); *C12N 2513/00* (2013.01); *C12N 2533/50* (2013.01)

(58) Field of Classification Search

None

See application file for complete search history.

(56) References Cited

U.S. PATENT DOCUMENTS

| | | | |
|---|---|---|---|
| 5,493,007 A | 2/1996 | Burnier et al. | |
| 2005/0070466 A1 | 3/2005 | Cuthbertson et al. | |
| 2005/0142068 A1 | 6/2005 | Verdugo-Gazdik | |
| 2010/0316565 A1 | 12/2010 | Newton et al. | |
| 2013/0197189 A1 | 8/2013 | Aimetti et al. | |
| 2018/0170977 A1 | 6/2018 | Hedhammar | |
| 2022/0098240 A1* | 3/2022 | Minami | C12M 25/14 |

FOREIGN PATENT DOCUMENTS

| | | | |
|---|---|---|---|
| CN | 108026152 | A | 5/2018 |
| JP | 06-509551 | A | 10/1994 |
| JP | 2005-507376 | A | 3/2005 |
| JP | 2011-506273 | A | 3/2011 |
| JP | 2018-527404 | A | 9/2018 |
| WO | 2018/115203 | A1 | 6/2018 |

OTHER PUBLICATIONS

Biosynthesis, "Unnatural/Unusual Amino acids," available online at https://www.biosyn.com/unnatural-unusual-amino-acids.aspx, 3 pages (first available 2014) (Year: 2014).*

Office Action issued Jun. 13, 2024 in Chinese Application No. 202080042693.4.

Office Action dated Sep. 27, 2022 issued by the Japanese Patent Office in Japanese Application No. 2021-526079.

Ivanov, B. et al., "Synthesis and Use of a New Bromoacetyl-Derivatized Heterotrifunctional Amino Acid for Conjugation of Cyclic RGD-Containing Peptides Derived from Human Bone Sialoprotein", Bioconjugate Chem, 1995, vol. 6, p. 269-277 (9 pages total).

Koehler, K. C. et al., "Development of a Maleimide Amino Acid for Use as a Tool for Peptide Conjugation and Modification", International Journal of Peptide Research and Therapeutics, 2013, vol. 19, pp. 265-274 (10 pages total).

Internal Search Report dated Aug. 25, 2020 from the International Searching Authority in International Application No. PCT/JP2020/022558.

Written Opinion dated Aug. 25, 2020 from the International Searching Authority in International Application No. PCT/JP2020/022558.

Internal Preliminary Report on Patentability with the translation of Written Opinion dated Dec. 14, 2021 from the International Bureau in International Application No. PCT/JP2020/022558.

Communication dated Jul. 29, 2022, issued by the European Patent Office in European Patent Application No. 20821877.6.

Barker, P. L. et al., "Cyclic RGD Peptide Analogues as Antiplatelet Antithrombotics", Journal Of Medicinal Chemistry, American Chemical Society, May 29, 1992, vol. 35, No. 11, p. 2040-2048, (9 pages total).

Ojima, I., et al., "Antithrombotic Agents: From RGD to Peptide Mimetics", Bioorganic & Medicinal Chemistry, Elsevier Science Ltd, Jan. 1995, vol. 3, No. 4, pp. 337-360, (24 pages total).

Office Action issued Sep. 1, 2023 in Chinese Application No. 202080042693.4.

Office Action issued Jan. 2, 2025 in European Patent Application No. 20821877.6.

* cited by examiner

*Primary Examiner* — Thea D'Ambrosio

(74) *Attorney, Agent, or Firm* — Sughrue Mion, PLLC

(57) ABSTRACT

There is provided a cyclic peptide containing a cyclic segment containing an RGD sequence and having 8 to 14 amino acid residues. A thioether bond is formed between an amino acid residue $X^a$ located on a most N-terminal side of the cyclic segment and an amino acid residue $X^b$ located on a most C-terminal side of the cyclic segment. However, in a case where one of the amino acid residue $X^a$ and the amino acid residue $X^b$ is a cysteine residue, an α carbon of the other amino acid residue of the amino acid residue $X^a$ and the amino acid residue $X^b$ is separated from a sulfur atom of the cysteine residue by five or more atoms.

14 Claims, No Drawings

Specification includes a Sequence Listing.

SEQUENCE LISTING

<160> NUMBER OF SEQ ID NOS: 174

<210> SEQ ID NO 1
<211> LENGTH: 8
<212> TYPE: PRT
<213> ORGANISM: Artificial Sequence
<220> FEATURE:
<223> OTHER INFORMATION: Synthetic Sequence, Region in Cyclic Segment

<400> SEQUENCE: 1

Ile Pro Arg Gly Asp Asn Phe Arg
1 5

<210> SEQ ID NO 2
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 1
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 2

Lys Lys Lys Gly Xaa Ile Pro Arg Gly Asp Asn Phe Arg Xaa Ala
1 5 10 15

<210> SEQ ID NO 3
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 2
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 3

Lys Lys Lys Ala Xaa Ile Pro Arg Gly Asp Asn Phe Arg Xaa Ala
1 5 10 15

<210> SEQ ID NO 4
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic Peptide 3
<220> FEATURE:
<221> NAME/KEY: misc_feature
<222> LOCATION: (4)..(4)
<223> OTHER INFORMATION: Homocystein

```
<220> FEATURE:
<221> NAME/KEY: thioeth
<222> LOCATION: (4)..(13)
<223> OTHER INFORMATION: Thioether bridge between residues 4 and 13
<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 4

Lys Lys Lys Xaa Ile Pro Arg Gly Asp Asn Phe Arg Xaa Ala
1               5                   10


<210> SEQ ID NO 5
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic
      Peptide 4
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(13)
<223> OTHER INFORMATION: Thioether bridge between residues 4 and 13
<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 5

Lys Lys Lys Xaa Ile Pro Arg Gly Asp Asn Phe Arg Xaa Gly
1               5                   10


<210> SEQ ID NO 6
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic
      Peptide 5
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(13)
<223> OTHER INFORMATION: Thioether bridge between residues 4 and 13
<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 6

Lys Lys Lys Xaa Ile Pro Arg Gly Asp Asn Phe Arg Xaa Asp
1               5                   10


<210> SEQ ID NO 7
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic
      Peptide 6
<220> FEATURE:
<221> NAME/KEY: misc_feature
<222> LOCATION: (5)..(5)
<223> OTHER INFORMATION: Homocystein
<220> FEATURE:
```

<221> NAME/KEY: thioeth
<222> LOCATION: (5)..(13)
<223> OTHER INFORMATION: Thioether bridge between residues 5 and 13
<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 7

Lys Lys Lys Gly Xaa Ile Pro Arg Gly Asp Asn Phe Xaa Ala
1 5 10

<210> SEQ ID NO 8
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic Peptide 7
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 8

Lys Lys Lys Gly Xaa Ile Pro Arg Gly Asp Asn Phe Arg Xaa
1 5 10

<210> SEQ ID NO 9
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic Peptide 8
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(13)
<223> OTHER INFORMATION: Thioether bridge between residues 5 and 13
<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 9

Lys Lys Lys Gly Xaa Pro Arg Gly Asp Asn Phe Arg Xaa Ala
1 5 10

<210> SEQ ID NO 10
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic Peptide 9
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth

```
<222> LOCATION: (4)..(12)
<223> OTHER INFORMATION: Thioether bridge between residues 4 and 12
<220> FEATURE:
<221> NAME/KEY: misc_feature
<222> LOCATION: (12)..(12)
<223> OTHER INFORMATION: 2-amino-4-(acetylamino)butanoic acid

<400> SEQUENCE: 10

Lys Lys Lys Xaa Pro Arg Gly Asp Asn Phe Arg Xaa Ala
1               5                   10


<210> SEQ ID NO 11
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic
      Peptide 10
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(12)
<223> OTHER INFORMATION: Thioether bridge between residues 4 and 12
<220> FEATURE:
<221> NAME/KEY: misc_feature
<222> LOCATION: (12)..(12)
<223> OTHER INFORMATION: 2-amino-4-(acetylamino)butanoic acid

<400> SEQUENCE: 11

Lys Lys Lys Xaa Ile Pro Arg Gly Asp Asn Phe Xaa Ala
1               5                   10


<210> SEQ ID NO 12
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic
      Peptide 11
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(13)
<223> OTHER INFORMATION: Thioether bridge between residues 4 and 13
<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 12

Lys Lys Lys Xaa Ile Pro Arg Gly Asp Asn Phe Arg Xaa
1               5                   10


<210> SEQ ID NO 13
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic
      Peptide 12
<220> FEATURE:
<221> NAME/KEY: misc_feature
<222> LOCATION: (4)..(4)
<223> OTHER INFORMATION: 2-amino-3-(acetylamino)propanoic acid
<220> FEATURE:
<221> NAME/KEY: thioeth
<222> LOCATION: (4)..(13)
```

<223> OTHER INFORMATION: Thioether bridge between residues 4 and 13
<220> FEATURE:
<221> NAME/KEY: misc_feature
<222> LOCATION: (13)..(13)
<223> OTHER INFORMATION: Homocystein

<400> SEQUENCE: 13

Lys Lys Lys Xaa Ile Pro Arg Gly Asp Asn Phe Arg Xaa
1 5 10

<210> SEQ ID NO 14
<211> LENGTH: 12
<212> TYPE: PRT
<213> ORGANISM: Artificial Sequence
<220> FEATURE:
<223> OTHER INFORMATION: Synthetic Sequence, Integrin-binding Cyclic Peptide 13
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(12)
<223> OTHER INFORMATION: Thioether bridge between residues 4 and 12
<220> FEATURE:
<221> NAME/KEY: misc_feature
<222> LOCATION: (12)..(12)
<223> OTHER INFORMATION: 2-amino-4-(acetylamino)butanoic acid

<400> SEQUENCE: 14

Lys Lys Lys Xaa Ile Pro Arg Gly Asp Asn Phe Xaa
1 5 10

<210> SEQ ID NO 15
<211> LENGTH: 12
<212> TYPE: PRT
<213> ORGANISM: Artificial Sequence
<220> FEATURE:
<223> OTHER INFORMATION: Synthetic Sequence, Integrin-binding Cyclic Peptide 14
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(12)
<223> OTHER INFORMATION: Thioether bridge between residues 4 and 12
<220> FEATURE:
<221> NAME/KEY: misc_feature
<222> LOCATION: (12)..(12)
<223> OTHER INFORMATION: 2-amino-4-(acetylamino)butanoic acid

<400> SEQUENCE: 15

Lys Lys Lys Xaa Val Pro Arg Gly Asp Asn Phe Xaa
1 5 10

<210> SEQ ID NO 16
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 15
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(14)
<223> OTHER INFORMATION: Thioether bridge between residues 4 and 14

```
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 16

Lys Lys Lys Xaa Ala Ile Pro Arg Gly Asp Asn Phe Arg Xaa Ala
1               5                   10                  15


<210> SEQ ID NO 17
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 16
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(14)
<223> OTHER INFORMATION: Thioether bridge between residues 4 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 17

Lys Lys Lys Xaa Ile Pro Arg Gly Asp Asn Phe Arg Ala Xaa Ala
1               5                   10                  15


<210> SEQ ID NO 18
<211> LENGTH: 16
<212> TYPE: PRT
<213> ORGANISM: Artificial Sequence
<220> FEATURE:
<223> OTHER INFORMATION: Synthetic Sequence, Integrin-binding Cyclic
      Peptide 17
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(15)
<223> OTHER INFORMATION: Thioether bridge between residues 4 and 15
<220> FEATURE:
<221> NAME/KEY: misc_feature
<222> LOCATION: (15)..(15)
<223> OTHER INFORMATION: 2-amino-4-(acetylamino)butanoic acid

<400> SEQUENCE: 18

Lys Lys Lys Xaa Ala Ile Pro Arg Gly Asp Asn Phe Arg Ala Xaa Ala
1               5                   10                  15


<210> SEQ ID NO 19
<211> LENGTH: 16
<212> TYPE: PRT
<213> ORGANISM: Artificial Sequence
<220> FEATURE:
<223> OTHER INFORMATION: Synthetic Sequence, Integrin-binding Cyclic
      Peptide 18
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(15)
<223> OTHER INFORMATION: Thioether bridge between residues 4 and 15
<220> FEATURE:
```

-continued

<221> NAME/KEY: misc_feature
<222> LOCATION: (15)..(15)
<223> OTHER INFORMATION: 2-amino-4-(acetylamino)butanoic acid

<400> SEQUENCE: 19

Lys Lys Lys Xaa Ala Ala Ile Pro Arg Gly Asp Asn Phe Arg Xaa Ala
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetic Sequence, Integrin-binding Cyclic Peptide 19
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(15)
<223> OTHER INFORMATION: Thioether bridge between residues 4 and 15
<220> FEATURE:
<221> NAME/KEY: misc_feature
<222> LOCATION: (15)..(15)
<223> OTHER INFORMATION: 2-amino-4-(acetylamino)butanoic acid

<400> SEQUENCE: 20

Lys Lys Lys Xaa Ile Pro Arg Gly Asp Asn Phe Arg Ala Ala Xaa Ala
1               5                   10                  15

<210> SEQ ID NO 21
<211> LENGTH: 17
<212> TYPE: PRT
<213> ORGANISM: Artificial Sequence
<220> FEATURE:
<223> OTHER INFORMATION: Synthetic Sequence, Integrin-binding Cyclic Peptide 20
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(16)
<223> OTHER INFORMATION: Thioether bridge between residues 5 and 16
<220> FEATURE:
<221> NAME/KEY: misc_feature
<222> LOCATION: (16)..(16)
<223> OTHER INFORMATION: 2-amino-4-(acetylamino)butanoic acid

<400> SEQUENCE: 21

Lys Lys Lys Gly Xaa Ala Ile Pro Arg Gly Asp Asn Phe Arg Ala Xaa
1               5                   10                  15

Ala

<210> SEQ ID NO 22
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic Peptide 21
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(13)
<223> OTHER INFORMATION: Thioether bridge between residues 4 and 13

-continued

<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 22

Lys Lys Lys Xaa Val Pro Arg Gly Asp Asn Phe Arg Xaa Ala
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic
      Peptide 22
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(13)
<223> OTHER INFORMATION: Thioether bridge between residues 4 and 13
<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 23

Lys Lys Lys Xaa Asp Pro Arg Gly Asp Asn Phe Arg Xaa Ala
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic
      Peptide 23
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(13)
<223> OTHER INFORMATION: Thioether bridge between residues 4 and 13
<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 24

Lys Lys Lys Xaa Glu Pro Arg Gly Asp Asn Phe Arg Xaa Ala
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic
      Peptide 24
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(13)
<223> OTHER INFORMATION: Thioether bridge between residues 4 and 13
<220> FEATURE:

-continued

<221> NAME/KEY: misc_feature
<222> LOCATION: (13)..(13)
<223> OTHER INFORMATION: 2-amino-4-(acetylamino)butanoic acid

<400> SEQUENCE: 25

Lys Lys Lys Xaa Tyr Pro Arg Gly Asp Asn Phe Arg Xaa Ala
1 5 10

<210> SEQ ID NO 26
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic Peptide 25
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(13)
<223> OTHER INFORMATION: Thioether bridge between residues 4 and 13
<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 26

Lys Lys Lys Xaa Ile Pro Arg Gly Asp Ser Phe Arg Xaa Ala
1 5 10

<210> SEQ ID NO 27
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic Peptide 26
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(13)
<223> OTHER INFORMATION: Thioether bridge between residues 4 and 13
<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 27

Lys Lys Lys Xaa Ile Pro Arg Gly Asp Asn Tyr Arg Xaa Ala
1 5 10

<210> SEQ ID NO 28
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 27
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 28

Lys Lys Lys Gly Xaa Leu Pro Arg Gly Asp Asn Phe Arg Xaa Ala
1 5 10 15

<210> SEQ ID NO 29
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 28
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 29

Lys Lys Lys Gly Xaa Leu Pro Arg Gly Asp Ser Phe Arg Xaa Ala
1 5 10 15

<210> SEQ ID NO 30
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 29
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 30

Lys Lys Lys Ala Xaa Val Pro Arg Gly Asp Asn Tyr Arg Xaa Asp
1 5 10 15

<210> SEQ ID NO 31
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 30
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)

-continued

<223> OTHER INFORMATION: 2-amino-4-(acetylamino)butanoic acid

<400> SEQUENCE: 31

Lys Lys Lys Ala Xaa Ile Pro Arg Gly Asp Asn Tyr Arg Xaa Asp
1 5 10 15

<210> SEQ ID NO 32
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 31
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 32

Lys Lys Lys Ala Xaa Leu Pro Arg Gly Asp Asn Tyr Arg Xaa Asp
1 5 10 15

<210> SEQ ID NO 33
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 32
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 33

Lys Lys Lys Ala Xaa Tyr Pro Arg Gly Asp Asn Tyr Arg Xaa Asp
1 5 10 15

<210> SEQ ID NO 34
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 33
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 34

Lys Lys Lys Ala Xaa Glu Pro Arg Gly Asp Ser Tyr Arg Xaa Asp
1 5 10 15

<210> SEQ ID NO 35
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 34
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 35

Lys Lys Lys Ala Xaa Glu Pro Arg Gly Asp Asn Phe Arg Xaa Asp
1 5 10 15

<210> SEQ ID NO 36
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 35
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 36

Lys Lys Lys Ala Xaa Glu Pro Arg Gly Asp Asn Tyr Asp Xaa Asp
1 5 10 15

<210> SEQ ID NO 37
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 36
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 37

Lys Lys Lys Ala Xaa Glu Pro Arg Gly Asp Asn Tyr Glu Xaa Asp
1 5 10 15

<210> SEQ ID NO 38
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 37
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 38

Lys Lys Lys Gly Xaa Glu Pro Arg Gly Asp Asn Tyr Arg Xaa Asp
1 5 10 15

<210> SEQ ID NO 39
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 38
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 39

Lys Lys Lys Asp Xaa Glu Pro Arg Gly Asp Asn Tyr Arg Xaa Asp
1 5 10 15

<210> SEQ ID NO 40
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 39
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 40

-continued

Lys Lys Lys Glu Xaa Glu Pro Arg Gly Asp Asn Tyr Arg Xaa Asp
1 5 10 15

<210> SEQ ID NO 41
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 40
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 41

Lys Lys Lys Ala Xaa Glu Pro Arg Gly Asp Asn Tyr Arg Xaa Gly
1 5 10 15

<210> SEQ ID NO 42
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 41
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 42

Lys Lys Lys Ala Xaa Glu Pro Arg Gly Asp Asn Tyr Arg Xaa Ala
1 5 10 15

<210> SEQ ID NO 43
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 42
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 43

Lys Lys Lys Ala Xaa Glu Pro Arg Gly Asp Asn Tyr Arg Xaa Asp
1 5 10 15

<210> SEQ ID NO 44
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 43
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 44

Lys Lys Lys Ala Xaa Glu Pro Arg Gly Asp Asn Tyr Arg Xaa Glu
1 5 10 15

<210> SEQ ID NO 45
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic Peptide 44
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(13)
<223> OTHER INFORMATION: Thioether bridge between residues 4 and 13
<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 45

Lys Lys Lys Xaa Glu Pro Arg Gly Asp Asn Tyr Arg Xaa
1 5 10

<210> SEQ ID NO 46
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic Peptide 45
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 46

Lys Lys Lys Ala Xaa Glu Pro Arg Gly Asp Asn Tyr Arg Xaa

-continued 1 5 10

<210> SEQ ID NO 47
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic
Peptide 46
<220> FEATURE:
<221> NAME/KEY: misc_feature
<222> LOCATION: (4)..(4)
<223> OTHER INFORMATION: 2-amino-3-(acetylamino)propanoic acid
<220> FEATURE:
<221> NAME/KEY: thioeth
<222> LOCATION: (4)..(13)
<223> OTHER INFORMATION: Thioether bridge between residues 4 and 13
<220> FEATURE:
<221> NAME/KEY: misc_feature
<222> LOCATION: (13)..(13)
<223> OTHER INFORMATION: Homocystein

<400> SEQUENCE: 47

Lys Lys Lys Xaa Glu Pro Arg Gly Asp Asn Tyr Arg Xaa
1 5 10

<210> SEQ ID NO 48
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic
Peptide 47
<220> FEATURE:
<221> NAME/KEY: misc_feature
<222> LOCATION: (5)..(5)
<223> OTHER INFORMATION: 2-amino-3-(acetylamino)propanoic acid
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: Homocystein

<400> SEQUENCE: 48

Lys Lys Lys Ala Xaa Glu Pro Arg Gly Asp Asn Tyr Arg Xaa
1 5 10

<210> SEQ ID NO 49
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
Peptide 48
<220> FEATURE:
<221> NAME/KEY: misc_feature
<222> LOCATION: (5)..(5)
<223> OTHER INFORMATION: 2-amino-3-(acetylamino)propanoic acid
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: Homocystein

<400> SEQUENCE: 49

Lys Lys Lys Ala Xaa Glu Pro Arg Gly Asp Asn Tyr Arg Xaa Asp
1 5 10 15

<210> SEQ ID NO 50
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic
Peptide 49
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(13)
<223> OTHER INFORMATION: Thioether bridge between residues 4 and 13
<220> FEATURE:
<221> NAME/KEY: MOD_RES
<222> LOCATION: (13)..(13)
<223> OTHER INFORMATION: AMIDATION
<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 50

Lys Lys Lys Xaa Glu Pro Arg Gly Asp Asn Tyr Arg Xaa
1 5 10

<210> SEQ ID NO 51
<211> LENGTH: 14
<212> TYPE: PRT
<213> ORGANISM: Artificial Sequence
<220> FEATURE:
<223> OTHER INFORMATION: Integrin-binding Cyclic Peptide 50
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid
<220> FEATURE:
<221> NAME/KEY: MOD_RES
<222> LOCATION: (14)..(14)
<223> OTHER INFORMATION: AMIDATION

<400> SEQUENCE: 51

Lys Lys Lys Ala Xaa Glu Pro Arg Gly Asp Asn Tyr Arg Xaa
1 5 10

<210> SEQ ID NO 52
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic
Peptide 51
<220> FEATURE:
<221> NAME/KEY: misc_feature
<222> LOCATION: (4)..(4)
<223> OTHER INFORMATION: beta-alanine
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)

-continued

<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid
<220> FEATURE:
<221> NAME/KEY: MOD_RES
<222> LOCATION: (14)..(14)
<223> OTHER INFORMATION: AMIDATION

<400> SEQUENCE: 52

Lys Lys Lys Xaa Xaa Glu Pro Arg Gly Asp Asn Tyr Arg Xaa
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic
      Peptide 52
<220> FEATURE:
<221> NAME/KEY: misc_feature
<222> LOCATION: (4)..(4)
<223> OTHER INFORMATION: 2-amino-3-(acetylamino)propanoic acid
<220> FEATURE:
<221> NAME/KEY: thioeth
<222> LOCATION: (4)..(13)
<223> OTHER INFORMATION: Thioether bridge between residues 4 and 13
<220> FEATURE:
<221> NAME/KEY: misc_feature
<222> LOCATION: (13)..(13)
<223> OTHER INFORMATION: Homocystein
<220> FEATURE:
<221> NAME/KEY: MOD_RES
<222> LOCATION: (13)..(13)
<223> OTHER INFORMATION: AMIDATION

<400> SEQUENCE: 53

Lys Lys Lys Xaa Glu Pro Arg Gly Asp Asn Tyr Arg Xaa
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic
      Peptide 53
<220> FEATURE:
<221> NAME/KEY: misc_feature
<222> LOCATION: (5)..(5)
<223> OTHER INFORMATION: 2-amino-3-(acetylamino)propanoic acid
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: Homocystein
<220> FEATURE:
<221> NAME/KEY: MOD_RES
<222> LOCATION: (14)..(14)
<223> OTHER INFORMATION: AMIDATION

<400> SEQUENCE: 54

Lys Lys Lys Ala Xaa Glu Pro Arg Gly Asp Asn Tyr Arg Xaa
1               5                   10

<210> SEQ ID NO 55
<211> LENGTH: 15
<212> TYPE: PRT

<213> ORGANISM: Artificial Sequence
<220> FEATURE:
<223> OTHER INFORMATION: Synthetic Sequence, Integrin-binding Cyclic
      Peptide 54
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 55

Lys Lys Lys Gly Xaa Ile Pro Arg Gly Asp Thr Phe Arg Xaa Ala
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 55
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 56

Lys Lys Lys Gly Xaa Ile Pro Arg Gly Asp Thr Phe Arg Xaa Gly
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 56
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 57

Lys Lys Lys Ala Xaa Ile Pro Arg Gly Asp Thr Phe Arg Xaa Ala
1               5                   10                  15

<210> SEQ ID NO 58
<211> LENGTH: 14
<212> TYPE: PRT
<213> ORGANISM: Artificial Sequence

```
<220> FEATURE:
<223> OTHER INFORMATION: Synthetic Sequence, Integrin-binding Cyclic
      Peptide 57
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(13)
<223> OTHER INFORMATION: Thioether bridge between residues 4 and 13
<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 58

Lys Lys Lys Xaa Ile Pro Arg Gly Asp Thr Phe Arg Xaa Ala
1               5                   10


<210> SEQ ID NO 59
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic
      Peptide 58
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(13)
<223> OTHER INFORMATION: Thioether bridge between residues 5 and 13
<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 59

Lys Lys Lys Gly Xaa Ile Pro Arg Gly Asp Thr Phe Xaa Ala
1               5                   10


<210> SEQ ID NO 60
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic
      Peptide 59
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 60

Lys Lys Lys Gly Xaa Ile Pro Arg Gly Asp Thr Phe Arg Xaa
1               5                   10


<210> SEQ ID NO 61
<211> LENGTH: 13
<212> TYPE: PRT
<213> ORGANISM: Artificial Sequence
<220> FEATURE:
```

<223> OTHER INFORMATION: Synthetic Sequence, Integrin-binding Cyclic
      Peptide 60
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(12)
<223> OTHER INFORMATION: Thioether bridge between residues 4 and 12
<220> FEATURE:
<221> NAME/KEY: misc_feature
<222> LOCATION: (12)..(12)
<223> OTHER INFORMATION: 2-amino-4-(acetylamino)butanoic acid

<400> SEQUENCE: 61

Lys Lys Lys Xaa Ile Pro Arg Gly Asp Thr Phe Xaa Ala
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic
      Peptide 61
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(13)
<223> OTHER INFORMATION: Thioether bridge between residues 4 and 13
<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 62

Lys Lys Lys Xaa Ile Pro Arg Gly Asp Thr Phe Arg Xaa
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic
      Peptide 62
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(13)
<223> OTHER INFORMATION: Thioether bridge between residues 4 and 13
<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 63

Lys Lys Lys Xaa Ile Pro Arg Gly Asp Thr Phe Ala Xaa
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Synthetic Sequence, Integrin-binding Cyclic -continued

```
      Peptide 63
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(12)
<223> OTHER INFORMATION: Thioether bridge between residues 4 and 12
<220> FEATURE:
<221> NAME/KEY: misc_feature
<222> LOCATION: (12)..(12)
<223> OTHER INFORMATION: 2-amino-4-(acetylamino)butanoic acid

<400> SEQUENCE: 64

Lys Lys Lys Xaa Ile Pro Arg Gly Asp Thr Phe Xaa
1               5                   10


<210> SEQ ID NO 65
<211> LENGTH: 12
<212> TYPE: PRT
<213> ORGANISM: Artificial Sequence
<220> FEATURE:
<223> OTHER INFORMATION: Synthetic Sequence, Integrin-binding Cyclic
      Peptide 64
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(12)
<223> OTHER INFORMATION: Thioether bridge between residues 4 and 12
<220> FEATURE:
<221> NAME/KEY: misc_feature
<222> LOCATION: (12)..(12)
<223> OTHER INFORMATION: 2-amino-4-(acetylamino)butanoic acid

<400> SEQUENCE: 65

Lys Lys Lys Xaa Val Pro Arg Gly Asp Thr Phe Xaa
1               5                   10


<210> SEQ ID NO 66
<211> LENGTH: 12
<212> TYPE: PRT
<213> ORGANISM: Artificial Sequence
<220> FEATURE:
<223> OTHER INFORMATION: Synthetic Sequence, Integrin-binding Cyclic
      Peptide 65
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(12)
<223> OTHER INFORMATION: Thioether bridge between residues 4 and 12
<220> FEATURE:
<221> NAME/KEY: misc_feature
<222> LOCATION: (12)..(12)
<223> OTHER INFORMATION: 2-amino-4-(acetylamino)butanoic acid

<400> SEQUENCE: 66

Lys Lys Lys Xaa Ile Pro Arg Gly Asp Val Phe Xaa
1               5                   10


<210> SEQ ID NO 67
<211> LENGTH: 12
<212> TYPE: PRT
<213> ORGANISM: Artificial Sequence
<220> FEATURE:
<223> OTHER INFORMATION: Synthetic Sequence, Integrin-binding Cyclic
      Peptide 66
```

<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(12)
<223> OTHER INFORMATION: Thioether bridge between residues 4 and 12
<220> FEATURE:
<221> NAME/KEY: misc_feature
<222> LOCATION: (12)..(12)
<223> OTHER INFORMATION: 2-amino-4-(acetylamino)butanoic acid

<400> SEQUENCE: 67

Lys Lys Lys Xaa Val Pro Arg Gly Asp Val Phe Xaa
1 5 10

<210> SEQ ID NO 68
<211> LENGTH: 17
<212> TYPE: PRT
<213> ORGANISM: Artificial Sequence
<220> FEATURE:
<223> OTHER INFORMATION: Synthetic Sequence, Integrin-binding Cyclic Peptide 67
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(16)
<223> OTHER INFORMATION: Thioether bridge between residues 5 and 16
<220> FEATURE:
<221> NAME/KEY: misc_feature
<222> LOCATION: (16)..(16)
<223> OTHER INFORMATION: 2-amino-4-(acetylamino)butanoic acid

<400> SEQUENCE: 68

Lys Lys Lys Gly Xaa Ala Ile Pro Arg Gly Asp Thr Phe Arg Ala Xaa
1 5 10 15

Ala

<210> SEQ ID NO 69
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 68
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (6)..(6)
<223> OTHER INFORMATION: Homotyrosine
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 69

Lys Lys Lys Gly Xaa Xaa Pro Arg Gly Asp Thr Phe Arg Xaa Ala
1 5 10 15

<210> SEQ ID NO 70
<211> LENGTH: 15

```
<212> TYPE: PRT
<213> ORGANISM: Artificial Sequence
<220> FEATURE:
<223> OTHER INFORMATION: Synthetic Sequence, Integrin-binding Cyclic
      Peptide 69
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 70

Lys Lys Lys Gly Xaa Glu Pro Arg Gly Asp Thr Phe Arg Xaa Ala
1               5                   10                  15


<210> SEQ ID NO 71
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 70
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 71

Lys Lys Lys Gly Xaa Val Pro Arg Gly Asp Thr Phe Arg Xaa Ala
1               5                   10                  15


<210> SEQ ID NO 72
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 71
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 72

Lys Lys Lys Gly Xaa Leu Pro Arg Gly Asp Thr Phe Arg Xaa Ala
1               5                   10                  15


<210> SEQ ID NO 73
<211> LENGTH: 15
<212> TYPE: PRT
```

<213> ORGANISM: Artificial Sequence
<220> FEATURE:
<223> OTHER INFORMATION: Synthetic Sequence, Integrin-binding Cyclic
Peptide 72
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 73

Lys Lys Lys Gly Xaa Ile Pro Arg Gly Asp Ser Phe Arg Xaa Ala
1 5 10 15

<210> SEQ ID NO 74
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
Peptide 73
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (11)..(11)
<223> OTHER INFORMATION: Homoserine
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 74

Lys Lys Lys Gly Xaa Ile Pro Arg Gly Asp Xaa Phe Arg Xaa Ala
1 5 10 15

<210> SEQ ID NO 75
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
Peptide 74
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 75

Lys Lys Lys Ala Xaa Val Pro Arg Gly Asp Thr Phe Arg Xaa Ala
1 5 10 15

```
<210> SEQ ID NO 76
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 75
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 76

Lys Lys Lys Ala Xaa Thr Pro Arg Gly Asp Thr Phe Arg Xaa Ala
1               5                   10                  15


<210> SEQ ID NO 77
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 76
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 77

Lys Lys Lys Ala Xaa Ile Thr Arg Gly Asp Thr Phe Arg Xaa Ala
1               5                   10                  15


<210> SEQ ID NO 78
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 77
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 78

Lys Lys Lys Ala Xaa Ile Ser Arg Gly Asp Thr Phe Arg Xaa Ala
1               5                   10                  15


<210> SEQ ID NO 79
```

```
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 78
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 79

Lys Lys Lys Ala Xaa Ile Pro Arg Gly Asp Val Phe Arg Xaa Ala
1               5                   10                  15


<210> SEQ ID NO 80
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 79
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 80

Lys Lys Lys Ala Xaa Ile Pro Arg Gly Asp Ala Phe Arg Xaa Ala
1               5                   10                  15


<210> SEQ ID NO 81
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 80
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 81

Lys Lys Lys Ala Xaa Ile Pro Arg Gly Asp Thr Pro Arg Xaa Ala
1               5                   10                  15


<210> SEQ ID NO 82
<211> LENGTH: 15
```

<212> TYPE: PRT
<213> ORGANISM: Artificial Sequence
<220> FEATURE:
<223> OTHER INFORMATION: Synthetic Sequence, Integrin-binding Cyclic
Peptide 81
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 82

Lys Lys Lys Ala Xaa Ile Pro Arg Gly Asp Thr Tyr Arg Xaa Ala
1 5 10 15

<210> SEQ ID NO 83
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
Peptide 82
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 83

Lys Lys Lys Ala Xaa Ile Pro Arg Gly Asp Thr Phe Thr Xaa Ala
1 5 10 15

<210> SEQ ID NO 84
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
Peptide 83
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 84

Lys Lys Lys Ala Xaa Ile Pro Arg Gly Asp Thr Phe Ser Xaa Ala
1 5 10 15

<210> SEQ ID NO 85
<211> LENGTH: 15
<212> TYPE: PRT

<213> ORGANISM: Artificial Sequence
<220> FEATURE:
<223> OTHER INFORMATION: Synthetic Sequence, Integrin-binding Cyclic
      Peptide 84
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 85

Lys Lys Lys Gly Xaa Ile Pro Arg Gly Asp Thr Phe Ala Xaa Gly
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 85
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 86

Lys Lys Lys Ala Xaa Ile Pro Arg Gly Asp Thr Phe Ala Xaa Gly
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 86
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 87

Lys Lys Lys Gly Xaa Ile Pro Arg Gly Asp Thr Phe Ala Xaa Ala
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
Peptide 87
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 88

Lys Lys Lys Ala Xaa Ile Pro Arg Gly Asp Thr Phe Ala Xaa Ala
1 5 10 15

<210> SEQ ID NO 89
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
Peptide 88
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 89

Lys Lys Lys Ala Xaa Ile Pro Arg Gly Asp Thr Phe Gly Xaa Ala
1 5 10 15

<210> SEQ ID NO 90
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
Peptide 89
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 90

Lys Lys Lys Ala Xaa Val Thr Arg Gly Asp Thr Phe Arg Xaa Ala
1 5 10 15

<210> SEQ ID NO 91
<211> LENGTH: 15
<212> TYPE: PRT
<213> ORGANISM: Artificial Sequence
<220> FEATURE:

<223> OTHER INFORMATION: Synthetic Sequence, Integrin-binding Cyclic
      Peptide 90
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 91

Lys Lys Lys Ala Xaa Ile Pro Arg Gly Asp Ala Phe Ala Xaa Ala
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 91
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 92

Lys Lys Lys Ala Xaa Val Pro Arg Gly Asp Ala Phe Ala Xaa Ala
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 92
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 93

Lys Lys Lys Ala Xaa Ile Pro Arg Gly Asp Ser Phe Ala Xaa Ala
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic -continued

```
      Peptide 93
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 94

Lys Lys Lys Ala Xaa Ile Pro Arg Gly Asp Ser Phe Ala Xaa Gly
1               5                   10                  15


<210> SEQ ID NO 95
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 94
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 95

Lys Lys Lys Gly Xaa Ile Pro Arg Gly Asp Ser Phe Ala Xaa Ala
1               5                   10                  15


<210> SEQ ID NO 96
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 95
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 96

Lys Lys Lys Gly Xaa Ile Pro Arg Gly Asp Ser Phe Ala Xaa Gly
1               5                   10                  15


<210> SEQ ID NO 97
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 96
```

<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 97

Lys Lys Lys Ala Xaa Val Pro Arg Gly Asp Ser Phe Ala Xaa Ala
1 5 10 15

<210> SEQ ID NO 98
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 97
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 98

Lys Lys Lys Ala Xaa Val Pro Arg Gly Asp Ser Phe Ala Xaa Gly
1 5 10 15

<210> SEQ ID NO 99
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 98
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 99

Lys Lys Lys Gly Xaa Val Pro Arg Gly Asp Ser Phe Ala Xaa Ala
1 5 10 15

<210> SEQ ID NO 100
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 99
<220> FEATURE:

<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 100

Lys Lys Lys Gly Xaa Val Pro Arg Gly Asp Ser Phe Ala Xaa Gly
1 5 10 15

<210> SEQ ID NO 101
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 100
<220> FEATURE:
<221> NAME/KEY: misc_feature
<222> LOCATION: (2)..(2)
<223> OTHER INFORMATION: Homocystein
<220> FEATURE:
<221> NAME/KEY: thioeth
<222> LOCATION: (2)..(11)
<223> OTHER INFORMATION: Thioether bridge between residues 2 and 11
<220> FEATURE:
<221> NAME/KEY: misc_feature
<222> LOCATION: (11)..(11)
<223> OTHER INFORMATION: 2-amino-4-(acetylamino)butanoic acid

<400> SEQUENCE: 101

Ala Xaa Ile Pro Arg Gly Asp Ser Phe Ala Xaa Ala Lys Lys Lys
1 5 10 15

<210> SEQ ID NO 102
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic Peptide 101
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(13)
<223> OTHER INFORMATION: Thioether bridge between residues 4 and 13
<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 102

Lys Lys Lys Xaa Ile Pro Arg Gly Asp Ser Phe Ala Xaa
1 5 10

<210> SEQ ID NO 103
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic Peptide 102
<220> FEATURE:
<221> NAME/KEY: misc_feature

```
<222> LOCATION: (4)..(4)
<223> OTHER INFORMATION: Homocystein
<220> FEATURE:
<221> NAME/KEY: thioeth
<222> LOCATION: (4)..(13)
<223> OTHER INFORMATION: Thioether bridge between residues 4 and 13
<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 103

Lys Lys Lys Xaa Val Pro Arg Gly Asp Ser Phe Ala Xaa
1               5                   10


<210> SEQ ID NO 104
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic
      Peptide 103
<220> FEATURE:
<221> NAME/KEY: misc_feature
<222> LOCATION: (1)..(1)
<223> OTHER INFORMATION: Homocystein
<220> FEATURE:
<221> NAME/KEY: thioeth
<222> LOCATION: (1)..(10)
<223> OTHER INFORMATION: Thioether bridge between residues 1 and 10
<220> FEATURE:
<221> NAME/KEY: misc_feature
<222> LOCATION: (10)..(10)
<223> OTHER INFORMATION: 2-amino-4-(acetylamino)butanoic acid

<400> SEQUENCE: 104

Xaa Val Pro Arg Gly Asp Thr Phe Ala Xaa Lys Lys Lys
1               5                   10


<210> SEQ ID NO 105
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic
      Peptide 104
<220> FEATURE:
<221> NAME/KEY: misc_feature
<222> LOCATION: (4)..(4)
<223> OTHER INFORMATION: Homocystein
<220> FEATURE:
<221> NAME/KEY: thioeth
<222> LOCATION: (4)..(13)
<223> OTHER INFORMATION: Thioether bridge between residues 4 and 13
<220> FEATURE:
<221> NAME/KEY: misc_feature
<222> LOCATION: (13)..(13)
<223> OTHER INFORMATION: 2-amino-4-(acetylamino)butanoic acid

<400> SEQUENCE: 105

Lys Lys Lys Xaa Val Pro Arg Gly Asp Thr Phe Ala Xaa
1               5                   10


<210> SEQ ID NO 106
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 105
<220> FEATURE:
<221> NAME/KEY: misc_feature
<222> LOCATION: (5)..(5)
```

```
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 106

Lys Lys Lys Gly Xaa Val Pro Arg Gly Asp Thr Phe Ala Xaa Gly
1               5                   10                  15


<210> SEQ ID NO 107
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 106
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 107

Lys Lys Lys Gly Xaa Val Pro Arg Gly Asp Thr Phe Ala Xaa Ala
1               5                   10                  15


<210> SEQ ID NO 108
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 107
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 108

Lys Lys Lys Ala Xaa Val Pro Arg Gly Asp Thr Phe Ala Xaa Gly
1               5                   10                  15


<210> SEQ ID NO 109
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 108
<220> FEATURE:
<221> NAME/KEY: misc_feature
<222> LOCATION: (5)..(5)
<223> OTHER INFORMATION: Homocystein
```

<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 109

Lys Lys Lys Ala Xaa Val Pro Arg Gly Asp Thr Phe Ala Xaa Ala
1 5 10 15

<210> SEQ ID NO 110
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 109
<220> FEATURE:
<221> NAME/KEY: misc_feature
<222> LOCATION: (2)..(2)
<223> OTHER INFORMATION: Homocystein
<220> FEATURE:
<221> NAME/KEY: thioeth
<222> LOCATION: (2)..(11)
<223> OTHER INFORMATION: Thioether bridge between residues 2 and 11
<220> FEATURE:
<221> NAME/KEY: misc_feature
<222> LOCATION: (11)..(11)
<223> OTHER INFORMATION: 2-amino-4-(acetylamino)butanoic acid

<400> SEQUENCE: 110

Ala Xaa Val Pro Arg Gly Asp Thr Phe Ala Xaa Ala Lys Lys Lys
1 5 10 15

<210> SEQ ID NO 111
<211> LENGTH: 16
<212> TYPE: PRT
<213> ORGANISM: Artificial Sequence
<220> FEATURE:
<223> OTHER INFORMATION: Synthetic Sequence, Integrin-binding Cyclic Peptide 110
<220> FEATURE:
<221> NAME/KEY: misc_feature
<222> LOCATION: (6)..(6)
<223> OTHER INFORMATION: Homocystein
<220> FEATURE:
<221> NAME/KEY: thioeth
<222> LOCATION: (6)..(15)
<223> OTHER INFORMATION: Thioether bridge between residues 6 and 15
<220> FEATURE:
<221> NAME/KEY: misc_feature
<222> LOCATION: (15)..(15)
<223> OTHER INFORMATION: 2-amino-4-(acetylamino)butanoic acid

<400> SEQUENCE: 111

Lys Lys Lys Lys Ala Xaa Val Pro Arg Gly Asp Thr Phe Ala Xaa Ala
1 5 10 15

<210> SEQ ID NO 112
<211> LENGTH: 17
<212> TYPE: PRT
<213> ORGANISM: Artificial Sequence
<220> FEATURE:
<223> OTHER INFORMATION: Synthetic Sequence, Integrin-binding Cyclic Peptide 111
<220> FEATURE:
<221> NAME/KEY: misc_feature
<222> LOCATION: (7)..(7)
<223> OTHER INFORMATION: Homocystein
<220> FEATURE:

<221> NAME/KEY: thioeth
<222> LOCATION: (7)..(16)
<223> OTHER INFORMATION: Thioether bridge between residues 7 and 16
<220> FEATURE:
<221> NAME/KEY: misc_feature
<222> LOCATION: (16)..(16)
<223> OTHER INFORMATION: 2-amino-4-(acetylamino)butanoic acid

<400> SEQUENCE: 112

Lys Lys Lys Lys Lys Ala Xaa Val Pro Arg Gly Asp Thr Phe Ala Xaa
1 5 10 15

Ala

<210> SEQ ID NO 113
<211> LENGTH: 18
<212> TYPE: PRT
<213> ORGANISM: Artificial Sequence
<220> FEATURE:
<223> OTHER INFORMATION: Synthetic Sequence, Integrin-binding Cyclic Peptide 112
<220> FEATURE:
<221> NAME/KEY: misc_feature
<222> LOCATION: (8)..(8)
<223> OTHER INFORMATION: Homocystein
<220> FEATURE:
<221> NAME/KEY: thioeth
<222> LOCATION: (8)..(17)
<223> OTHER INFORMATION: Thioether bridge between residues 8 and 17
<220> FEATURE:
<221> NAME/KEY: misc_feature
<222> LOCATION: (17)..(17)
<223> OTHER INFORMATION: 2-amino-4-(acetylamino)butanoic acid

<400> SEQUENCE: 113

Lys Lys Lys Lys Lys Lys Ala Xaa Val Pro Arg Gly Asp Thr Phe Ala
1 5 10 15

Xaa Ala

<210> SEQ ID NO 114
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 113
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 114

Lys Lys Lys Ala Xaa Val Thr Arg Gly Asp Val Phe Thr Xaa Ala
1 5 10 15

<210> SEQ ID NO 115
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 114
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-3-(acetylamino)propanoic acid

<400> SEQUENCE: 115

Lys Lys Lys Gly Xaa Ile Pro Arg Gly Asp Thr Phe Arg Xaa Ala
1 5 10 15

<210> SEQ ID NO 116
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
Peptide 115
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: N-delta-acetyl-ornithine

<400> SEQUENCE: 116

Lys Lys Lys Gly Xaa Ile Pro Arg Gly Asp Thr Phe Arg Xaa Ala
1 5 10 15

<210> SEQ ID NO 117
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
Peptide 116
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: N-epsilon-acetyl-lysine

<400> SEQUENCE: 117

Lys Lys Lys Gly Xaa Ile Pro Arg Gly Asp Thr Phe Arg Xaa Ala
1 5 10 15

<210> SEQ ID NO 118
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
Peptide 117
<220> FEATURE:
<221> NAME/KEY: misc_feature
<222> LOCATION: (5)..(5)

<223> OTHER INFORMATION: 2-amino-3-(acetylamino)propanoic acid
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: Homocystein

<400> SEQUENCE: 118

Lys Lys Lys Gly Xaa Ile Pro Arg Gly Asp Thr Phe Arg Xaa Ala
1 5 10 15

<210> SEQ ID NO 119
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 118
<220> FEATURE:
<221> NAME/KEY: misc_feature
<222> LOCATION: (5)..(5)
<223> OTHER INFORMATION: 2-amino-4-(acetylamino)butanoic acid
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: Homocystein

<400> SEQUENCE: 119

Lys Lys Lys Gly Xaa Ile Pro Arg Gly Asp Thr Phe Arg Xaa Ala
1 5 10 15

<210> SEQ ID NO 120
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 119
<220> FEATURE:
<221> NAME/KEY: misc_feature
<222> LOCATION: (5)..(5)
<223> OTHER INFORMATION: N-delta-acetyl-ornithine
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: Homocystein

<400> SEQUENCE: 120

Lys Lys Lys Gly Xaa Ile Pro Arg Gly Asp Thr Phe Arg Xaa Ala
1 5 10 15

<210> SEQ ID NO 121
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 120
<220> FEATURE:
<221> NAME/KEY: misc_feature
<222> LOCATION: (5)..(5)
<223> OTHER INFORMATION: N-epsilon-acetyl-lysine
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: Homocystein

<400> SEQUENCE: 121

```
Lys Lys Lys Gly Xaa Ile Pro Arg Gly Asp Thr Phe Arg Xaa Ala
1               5                   10                  15
```

<210> SEQ ID NO 122
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 121
<220> FEATURE:
<221> NAME/KEY: misc_feature
<222> LOCATION: (5)..(5)
<223> OTHER INFORMATION: Homocystein
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: N-epsilon-oacetyl-lysine

<400> SEQUENCE: 122

```
Lys Lys Lys Ala Xaa Val Pro Arg Gly Asp Thr Phe Ala Xaa Ala
1               5                   10                  15
```

<210> SEQ ID NO 123
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 122
<220> FEATURE:
<221> NAME/KEY: misc_feature
<222> LOCATION: (5)..(5)
<223> OTHER INFORMATION: 2-amino-4-(acetylamino)butanoic acid
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: Homocystein

<400> SEQUENCE: 123

```
Lys Lys Lys Ala Xaa Val Pro Arg Gly Asp Thr Phe Ala Xaa Ala
1               5                   10                  15
```

<210> SEQ ID NO 124
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 123
<220> FEATURE:
<221> NAME/KEY: misc_feature
<222> LOCATION: (5)..(5)
<223> OTHER INFORMATION: Homocystein
<220> FEATURE:

-continued

<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: N-epsilon-acetyl-lysine

<400> SEQUENCE: 124

Lys Lys Lys Ala Xaa Ile Pro Arg Gly Asp Ser Phe Ala Xaa Ala
1 5 10 15

<210> SEQ ID NO 125
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 124
<220> FEATURE:
<221> NAME/KEY: misc_feature
<222> LOCATION: (5)..(5)
<223> OTHER INFORMATION: 2-amino-4-(acetylamino)butanoic acid
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: Homocystein

<400> SEQUENCE: 125

Lys Lys Lys Ala Xaa Ile Pro Arg Gly Asp Ser Phe Ala Xaa Ala
1 5 10 15

<210> SEQ ID NO 126
<211> LENGTH: 12
<212> TYPE: PRT
<213> ORGANISM: Artificial Sequence
<220> FEATURE:
<223> OTHER INFORMATION: Synthetic Sequence, Integrin-binding Cyclic Peptide 125
<220> FEATURE:
<221> NAME/KEY: misc_feature
<222> LOCATION: (2)..(2)
<223> OTHER INFORMATION: Homocystein
<220> FEATURE:
<221> NAME/KEY: thioeth
<222> LOCATION: (2)..(11)
<223> OTHER INFORMATION: Thioether bridge between residues 2 and 11
<220> FEATURE:
<221> NAME/KEY: misc_feature
<222> LOCATION: (11)..(11)
<223> OTHER INFORMATION: 2-amino-4-(acetylamino)butanoic acid

<400> SEQUENCE: 126

Ala Xaa Val Pro Arg Gly Asp Thr Phe Ala Xaa Ala
1 5 10

<210> SEQ ID NO 127
<211> LENGTH: 12
<212> TYPE: PRT
<213> ORGANISM: Artificial Sequence
<220> FEATURE:
<223> OTHER INFORMATION: Synthetic Sequence, Integrin-binding Cyclic Peptide 126
<220> FEATURE:
<221> NAME/KEY: misc_feature
<222> LOCATION: (2)..(2)
<223> OTHER INFORMATION: Homocystein
<220> FEATURE:
<221> NAME/KEY: thioeth -continued
<222> LOCATION: (2)..(11)
<223> OTHER INFORMATION: Thioether bridge between residues 2 and 11
<220> FEATURE:
<221> NAME/KEY: misc_feature
<222> LOCATION: (11)..(11)
<223> OTHER INFORMATION: 2-amino-4-(acetylamino)butanoic acid

<400> SEQUENCE: 127

Ala Xaa Ile Pro Arg Gly Asp Ser Phe Ala Xaa Ala
1 5 10

<210> SEQ ID NO 128
<211> LENGTH: 12
<212> TYPE: PRT
<213> ORGANISM: Artificial Sequence
<220> FEATURE:
<223> OTHER INFORMATION: Synthetic Sequence, Integrin-binding Cyclic Peptide 127
<220> FEATURE:
<221> NAME/KEY: misc_feature
<222> LOCATION: (2)..(2)
<223> OTHER INFORMATION: Homocystein
<220> FEATURE:
<221> NAME/KEY: thioeth
<222> LOCATION: (2)..(11)
<223> OTHER INFORMATION: Thioether bridge between residues 2 and 11
<220> FEATURE:
<221> NAME/KEY: misc_feature
<222> LOCATION: (11)..(11)
<223> OTHER INFORMATION: 2-amino-4-(acetylamino)butanoic acid

<400> SEQUENCE: 128

Ala Xaa Ile Pro Arg Gly Asp Ser Phe Ala Xaa Gly
1 5 10

<210> SEQ ID NO 129
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 128
<220> FEATURE:
<221> NAME/KEY: misc_feature
<222> LOCATION: (5)..(5)
<223> OTHER INFORMATION: Penicillamine
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-3-(acetylamino)propanoic acid

<400> SEQUENCE: 129

Lys Lys Lys Gly Xaa Ile Pro Arg Gly Asp Thr Phe Arg Xaa Ala
1 5 10 15

<210> SEQ ID NO 130
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 129
<220> FEATURE:
<221> NAME/KEY: misc_feature
<222> LOCATION: (5)..(5)
<223> OTHER INFORMATION: Penicillamine
<220> FEATURE:
<221> NAME/KEY: thioeth
<222> LOCATION: (5)..(14)

<223> OTHER INFORMATION: Thioether bridge between residues 5 and 14
<220> FEATURE:
<221> NAME/KEY: misc_feature
<222> LOCATION: (14)..(14)
<223> OTHER INFORMATION: 2-amino-4-(acetylamino)butanoic acid

<400> SEQUENCE: 130

Lys Lys Lys Gly Xaa Ile Pro Arg Gly Asp Thr Phe Arg Xaa Ala
1 5 10 15

<210> SEQ ID NO 131
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 130
<220> FEATURE:
<221> NAME/KEY: misc_feature
<222> LOCATION: (5)..(5)
<223> OTHER INFORMATION: Penicillamine
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: N-delta-acetyl-ornithine

<400> SEQUENCE: 131

Lys Lys Lys Gly Xaa Ile Pro Arg Gly Asp Thr Phe Arg Xaa Ala
1 5 10 15

<210> SEQ ID NO 132
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 131
<220> FEATURE:
<221> NAME/KEY: misc_feature
<222> LOCATION: (5)..(5)
<223> OTHER INFORMATION: Penicillamine
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: N-epsilon-acetyl-lysine

<400> SEQUENCE: 132

Lys Lys Lys Gly Xaa Ile Pro Arg Gly Asp Thr Phe Arg Xaa Ala
1 5 10 15

<210> SEQ ID NO 133
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 132
<220> FEATURE:
<221> NAME/KEY: misc_feature
<222> LOCATION: (5)..(5)
<223> OTHER INFORMATION: 2-amino-3-(acetylamino)propanoic acid
<220> FEATURE:
<221> NAME/KEY: thioeth
<222> LOCATION: (5)..(14)
<223> OTHER INFORMATION: Thioether bridge between residues 5 and 14

<220> FEATURE:
<221> NAME/KEY: misc_feature
<222> LOCATION: (14)..(14)
<223> OTHER INFORMATION: Penicillamine

<400> SEQUENCE: 133

Lys Lys Lys Gly Xaa Ile Pro Arg Gly Asp Thr Phe Arg Xaa Ala
1 5 10 15

<210> SEQ ID NO 134
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
Peptide 133
<220> FEATURE:
<221> NAME/KEY: misc_feature
<222> LOCATION: (5)..(5)
<223> OTHER INFORMATION: 2-amino-4-(acetylamino)butanoic acid
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: Penicillamine

<400> SEQUENCE: 134

Lys Lys Lys Gly Xaa Ile Pro Arg Gly Asp Thr Phe Arg Xaa Ala
1 5 10 15

<210> SEQ ID NO 135
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
Peptide 134
<220> FEATURE:
<221> NAME/KEY: misc_feature
<222> LOCATION: (5)..(5)
<223> OTHER INFORMATION: N-delta-acetyl-ornithine
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: Penicillamine

<400> SEQUENCE: 135

Lys Lys Lys Gly Xaa Ile Pro Arg Gly Asp Thr Phe Arg Xaa Ala
1 5 10 15

<210> SEQ ID NO 136
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
Peptide 135
<220> FEATURE:
<221> NAME/KEY: misc_feature
<222> LOCATION: (5)..(5)
<223> OTHER INFORMATION: N-epsilon-acetyl-lysine
<220> FEATURE:
<221> NAME/KEY: thioeth
<222> LOCATION: (5)..(14)
<223> OTHER INFORMATION: Thioether bridge between residues 5 and 14
<220> FEATURE:

<221> NAME/KEY: misc_feature
<222> LOCATION: (14)..(14)
<223> OTHER INFORMATION: Penicillamine

<400> SEQUENCE: 136

Lys Lys Lys Gly Xaa Ile Pro Arg Gly Asp Thr Phe Arg Xaa Ala
1 5 10 15

<210> SEQ ID NO 137
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 136
<220> FEATURE:
<221> NAME/KEY: misc_feature
<222> LOCATION: (5)..(5)
<223> OTHER INFORMATION: 2-amino-4-(acetylamino)butanoic acid
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: Penicillamine

<400> SEQUENCE: 137

Lys Lys Lys Ala Xaa Val Pro Arg Gly Asp Thr Phe Ala Xaa Ala
1 5 10 15

<210> SEQ ID NO 138
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 137
<220> FEATURE:
<221> NAME/KEY: misc_feature
<222> LOCATION: (5)..(5)
<223> OTHER INFORMATION: 2-amino-4-(acetylamino)butanoic acid
<220> FEATURE:
<221> NAME/KEY: thioeth
<222> LOCATION: (5)..(14)
<223> OTHER INFORMATION: Thioether bridge between residues 5 and 14
<220> FEATURE:
<221> NAME/KEY: misc_feature
<222> LOCATION: (14)..(14)
<223> OTHER INFORMATION: Penicillamine

<400> SEQUENCE: 138

Lys Lys Lys Ala Xaa Ile Pro Arg Gly Asp Ser Phe Ala Xaa Ala
1 5 10 15

<210> SEQ ID NO 139
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 138
<220> FEATURE:
<221> NAME/KEY: misc_feature
<222> LOCATION: (5)..(5)
<223> OTHER INFORMATION: 2-amino-4-(acetylamino)butanoic acid
<220> FEATURE:
<221> NAME/KEY: thioeth
<222> LOCATION: (5)..(14)
<223> OTHER INFORMATION: Thioether bridge between residues 5 and 14

<400> SEQUENCE: 139

```
Lys Lys Lys Gly Xaa Ile Pro Arg Gly Asp Thr Phe Arg Cys Ala
1               5                   10                  15


<210> SEQ ID NO 140
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 139
<220> FEATURE:
<221> NAME/KEY: misc_feature
<222> LOCATION: (5)..(5)
<223> OTHER INFORMATION: N-delta-acetyl-ornithine
<220> FEATURE:
<221> NAME/KEY: thioeth
<222> LOCATION: (5)..(14)
<223> OTHER INFORMATION: Thioether bridge between residues 5 and 14

<400> SEQUENCE: 140

Lys Lys Lys Gly Xaa Ile Pro Arg Gly Asp Thr Phe Arg Cys Ala
1               5                   10                  15


<210> SEQ ID NO 141
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 140
<220> FEATURE:
<221> NAME/KEY: misc_feature
<222> LOCATION: (5)..(5)
<223> OTHER INFORMATION: N-epsilon-acetyl-lysine
<220> FEATURE:
<221> NAME/KEY: thioeth
<222> LOCATION: (5)..(14)
<223> OTHER INFORMATION: Thioether bridge between residues 5 and 14

<400> SEQUENCE: 141

Lys Lys Lys Gly Xaa Ile Pro Arg Gly Asp Thr Phe Arg Cys Ala
1               5                   10                  15


<210> SEQ ID NO 142
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic
      Peptide 141
<220> FEATURE:
<221> NAME/KEY: misc_feature
<222> LOCATION: (4)..(4)
<223> OTHER INFORMATION: 2-amino-4-(acetylamino)butanoic acid
<220> FEATURE:
<221> NAME/KEY: thioeth
<222> LOCATION: (4)..(13)
<223> OTHER INFORMATION: Thioether bridge between residues 4 and 13

<400> SEQUENCE: 142

Lys Lys Lys Xaa Val Pro Arg Gly Asp Thr Phe Ala Cys
1               5                   10


<210> SEQ ID NO 143
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
      Peptide 142
<220> FEATURE:
```

<221> NAME/KEY: misc_feature
<222> LOCATION: (5)..(5)
<223> OTHER INFORMATION: 2-amino-4-(acetylamino)butanoic acid
<220> FEATURE:
<221> NAME/KEY: thioeth
<222> LOCATION: (5)..(14)
<223> OTHER INFORMATION: Thioether bridge between residues 5 and 14

<400> SEQUENCE: 143

Lys Lys Lys Ala Xaa Val Pro Arg Gly Asp Thr Phe Ala Cys Ala
1 5 10 15

<210> SEQ ID NO 144
<211> LENGTH: 12
<212> TYPE: PRT
<213> ORGANISM: Artificial Sequence
<220> FEATURE:
<223> OTHER INFORMATION: Synthetic Sequence, Integrin-binding Cyclic Peptide 143
<220> FEATURE:
<221> NAME/KEY: misc_feature
<222> LOCATION: (4)..(4)
<223> OTHER INFORMATION: 2-amino-4-(acetylamino)butanoic acid
<220> FEATURE:
<221> NAME/KEY: thioeth
<222> LOCATION: (4)..(12)
<223> OTHER INFORMATION: Thioether bridge between residues 4 and 12

<400> SEQUENCE: 144

Lys Lys Lys Xaa Val Pro Arg Gly Asp Asn Phe Cys
1 5 10

<210> SEQ ID NO 145
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic Peptide 144
<220> FEATURE:
<221> NAME/KEY: MISC_FEATURE
<222> LOCATION: (4)..(4)
<223> OTHER INFORMATION: Homocystein
<220> FEATURE:
<221> NAME/KEY: THIOETH
<222> LOCATION: (4)..(13)
<223> OTHER INFORMATION: Thioether bridge between residues 4 and 13
<220> FEATURE:
<221> NAME/KEY: MISC_FEATURE
<222> LOCATION: (13)..(13)
<223> OTHER INFORMATION: 2-amino-4-(acetylamino)butanoic acid

<400> SEQUENCE: 145

Lys Lys Lys Xaa Asp Pro Arg Gly Asp Thr Phe Ala Xaa
1 5 10

<210> SEQ ID NO 146
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic Peptide 145
<220> FEATURE:
<221> NAME/KEY: MISC_FEATURE
<222> LOCATION: (4)..(4)
<223> OTHER INFORMATION: Homocystein
<220> FEATURE:
<221> NAME/KEY: THIOETH
<222> LOCATION: (4)..(13)
<223> OTHER INFORMATION: Thioether bridge between residues 4 and 13
<220> FEATURE:
<221> NAME/KEY: MISC_FEATURE
<222> LOCATION: (13)..(13)
<223> OTHER INFORMATION: 2-amino-4-(acetylamino)butanoic acid

<400> SEQUENCE: 146

Lys Lys Lys Xaa Glu Pro Arg Gly Asp Thr Phe Ala Xaa
1 5 10

<210> SEQ ID NO 147
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic Peptide 146
<220> FEATURE:
<221> NAME/KEY: MISC_FEATURE
<222> LOCATION: (4)..(4)
<223> OTHER INFORMATION: Homocystein
<220> FEATURE:
<221> NAME/KEY: THIOETH
<222> LOCATION: (4)..(13)
<223> OTHER INFORMATION: Thioether bridge between residues 4 and 13
<220> FEATURE:
<221> NAME/KEY: MISC_FEATURE
<222> LOCATION: (13)..(13)
<223> OTHER INFORMATION: 2-amino-4-(acetylamino)butanoic acid

<400> SEQUENCE: 147

Lys Lys Lys Xaa Leu Pro Arg Gly Asp Thr Phe Ala Xaa
1 5 10

<210> SEQ ID NO 148
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic Peptide 147
<220> FEATURE:
<221> NAME/KEY: MISC_FEATURE
<222> LOCATION: (4)..(4)
<223> OTHER INFORMATION: Homocystein
<220> FEATURE:
<221> NAME/KEY: THIOETH
<222> LOCATION: (4)..(13)
<223> OTHER INFORMATION: Thioether bridge between residues 4 and 13
<220> FEATURE:
<221> NAME/KEY: MISC_FEATURE
<222> LOCATION: (13)..(13)
<223> OTHER INFORMATION: 2-amino-4-(acetylamino)butanoic acid

<400> SEQUENCE: 148

Lys Lys Lys Xaa Thr Pro Arg Gly Asp Thr Phe Ala Xaa
1 5 10

<210> SEQ ID NO 149
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic Peptide 148
<220> FEATURE:
<221> NAME/KEY: MISC_FEATURE
<222> LOCATION: (4)..(4)
<223> OTHER INFORMATION: Homocystein
<220> FEATURE:
<221> NAME/KEY: THIOETH
<222> LOCATION: (4)..(13)
<223> OTHER INFORMATION: Thioether bridge between residues 4 and 13
<220> FEATURE:
<221> NAME/KEY: MISC_FEATURE
<222> LOCATION: (13)..(13)

```
<223> OTHER INFORMATION: 2-amino-4-(acetylamino)butanoic acid

<400> SEQUENCE: 149

Lys Lys Lys Xaa Tyr Pro Arg Gly Asp Thr Phe Ala Xaa
1               5                   10


<210> SEQ ID NO 150
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic
      Peptide 149
<220> FEATURE:
<221> NAME/KEY: MISC_FEATURE
<222> LOCATION: (4)..(4)
<223> OTHER INFORMATION: Homocystein
<220> FEATURE:
<221> NAME/KEY: THIOETH
<222> LOCATION: (4)..(13)
<223> OTHER INFORMATION: Thioether bridge between residues 4 and 13
<220> FEATURE:
<221> NAME/KEY: MISC_FEATURE
<222> LOCATION: (13)..(13)
<223> OTHER INFORMATION: 2-amino-4-(acetylamino)butanoic acid

<400> SEQUENCE: 150

Lys Lys Lys Xaa Val Ser Arg Gly Asp Thr Phe Ala Xaa
1               5                   10


<210> SEQ ID NO 151
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic
      Peptide 150
<220> FEATURE:
<221> NAME/KEY: MISC_FEATURE
<222> LOCATION: (4)..(4)
<223> OTHER INFORMATION: Homocystein
<220> FEATURE:
<221> NAME/KEY: THIOETH
<222> LOCATION: (4)..(13)
<223> OTHER INFORMATION: Thioether bridge between residues 4 and 13
<220> FEATURE:
<221> NAME/KEY: MISC_FEATURE
<222> LOCATION: (13)..(13)
<223> OTHER INFORMATION: 2-amino-4-(acetylamino)butanoic acid

<400> SEQUENCE: 151

Lys Lys Lys Xaa Val Thr Arg Gly Asp Thr Phe Ala Xaa
1               5                   10


<210> SEQ ID NO 152
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic
      Peptide 151
<220> FEATURE:
<221> NAME/KEY: MISC_FEATURE
<222> LOCATION: (4)..(4)
<223> OTHER INFORMATION: Homocystein
<220> FEATURE:
<221> NAME/KEY: THIOETH
<222> LOCATION: (4)..(13)
<223> OTHER INFORMATION: Thioether bridge between residues 4 and 13
<220> FEATURE:
<221> NAME/KEY: MISC_FEATURE
<222> LOCATION: (13)..(13)
<223> OTHER INFORMATION: 2-amino-4-(acetylamino)butanoic acid
```

<400> SEQUENCE: 152

Lys Lys Lys Xaa Val Pro Arg Gly Asp Val Phe Ala Xaa
1 5 10

<210> SEQ ID NO 153
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic Peptide 152
<220> FEATURE:
<221> NAME/KEY: MISC_FEATURE
<222> LOCATION: (4)..(4)
<223> OTHER INFORMATION: Homocystein
<220> FEATURE:
<221> NAME/KEY: THIOETH
<222> LOCATION: (4)..(13)
<223> OTHER INFORMATION: Thioether bridge between residues 4 and 13
<220> FEATURE:
<221> NAME/KEY: MISC_FEATURE
<222> LOCATION: (13)..(13)
<223> OTHER INFORMATION: 2-amino-4-(acetylamino)butanoic acid

<400> SEQUENCE: 153

Lys Lys Lys Xaa Val Pro Arg Gly Asp Thr Phe Gly Xaa
1 5 10

<210> SEQ ID NO 154
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic Peptide 153
<220> FEATURE:
<221> NAME/KEY: MISC_FEATURE
<222> LOCATION: (4)..(4)
<223> OTHER INFORMATION: Homocystein
<220> FEATURE:
<221> NAME/KEY: THIOETH
<222> LOCATION: (4)..(13)
<223> OTHER INFORMATION: Thioether bridge between residues 4 and 13
<220> FEATURE:
<221> NAME/KEY: MISC_FEATURE
<222> LOCATION: (13)..(13)
<223> OTHER INFORMATION: 2-amino-4-(acetylamino)butanoic acid

<400> SEQUENCE: 154

Lys Lys Lys Xaa Val Pro Arg Gly Asp Thr Phe Ser Xaa
1 5 10

<210> SEQ ID NO 155
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic Peptide 154
<220> FEATURE:
<221> NAME/KEY: MISC_FEATURE
<222> LOCATION: (4)..(4)
<223> OTHER INFORMATION: Homocystein
<220> FEATURE:
<221> NAME/KEY: THIOETH
<222> LOCATION: (4)..(13)
<223> OTHER INFORMATION: Thioether bridge between residues 4 and 13
<220> FEATURE:
<221> NAME/KEY: MISC_FEATURE
<222> LOCATION: (13)..(13)
<223> OTHER INFORMATION: 2-amino-4-(acetylamino)butanoic acid -continued

<400> SEQUENCE: 155

Lys Lys Lys Xaa Val Pro Arg Gly Asp Thr Phe Thr Xaa
1 5 10

<210> SEQ ID NO 156
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic Peptide 155
<220> FEATURE:
<221> NAME/KEY: MISC_FEATURE
<222> LOCATION: (4)..(4)
<223> OTHER INFORMATION: Homocystein
<220> FEATURE:
<221> NAME/KEY: THIOETH
<222> LOCATION: (4)..(13)
<223> OTHER INFORMATION: Thioether bridge between residues 4 and 13
<220> FEATURE:
<221> NAME/KEY: MISC_FEATURE
<222> LOCATION: (13)..(13)
<223> OTHER INFORMATION: 2-amino-4-(acetylamino)butanoic acid

<400> SEQUENCE: 156

Lys Lys Lys Xaa Thr Thr Arg Gly Asp Thr Phe Ala Xaa
1 5 10

<210> SEQ ID NO 157
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic Peptide 156
<220> FEATURE:
<221> NAME/KEY: MISC_FEATURE
<222> LOCATION: (4)..(4)
<223> OTHER INFORMATION: Homocystein
<220> FEATURE:
<221> NAME/KEY: THIOETH
<222> LOCATION: (4)..(13)
<223> OTHER INFORMATION: Thioether bridge between residues 4 and 13
<220> FEATURE:
<221> NAME/KEY: MISC_FEATURE
<222> LOCATION: (13)..(13)
<223> OTHER INFORMATION: 2-amino-4-(acetylamino)butanoic acid

<400> SEQUENCE: 157

Lys Lys Lys Xaa Thr Pro Arg Gly Asp Ser Phe Ala Xaa
1 5 10

<210> SEQ ID NO 158
<211> LENGTH: 13
<212> TYPE: PRT
<213> ORGANISM: Artificial Sequence
<220> FEATURE:
<223> OTHER INFORMATION: Synthetic Sequence, Integrin-binding Cyclic Peptide 157
<220> FEATURE:
<221> NAME/KEY: MISC_FEATURE
<222> LOCATION: (4)..(4)
<223> OTHER INFORMATION: Homocystein
<220> FEATURE:
<221> NAME/KEY: THIOETH
<222> LOCATION: (4)..(13)
<223> OTHER INFORMATION: Thioether bridge between residues 4 and 13
<220> FEATURE:
<221> NAME/KEY: MISC_FEATURE
<222> LOCATION: (13)..(13)
<223> OTHER INFORMATION: 2-amino-4-(acetylamino)butanoic acid

<400> SEQUENCE: 158

Lys Lys Lys Xaa Thr Thr Arg Gly Asp Ser Phe Ala Xaa
1 5 10

<210> SEQ ID NO 159
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic
Peptide 158
<220> FEATURE:
<221> NAME/KEY: MISC_FEATURE
<222> LOCATION: (5)..(5)
<223> OTHER INFORMATION: Homocystein
<220> FEATURE:
<221> NAME/KEY: THIOETH
<222> LOCATION: (5)..(14)
<223> OTHER INFORMATION: Thioether bridge between residues 5 and 14
<220> FEATURE:
<221> NAME/KEY: MISC_FEATURE
<222> LOCATION: (14)..(14)
<223> OTHER INFORMATION: 2-amino-4-(acetylamino)butanoic acid

<400> SEQUENCE: 159

Lys Lys Lys Ala Xaa Thr Pro Arg Gly Asp Thr Phe Ala Xaa
1 5 10

<210> SEQ ID NO 160
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic
Peptide 159
<220> FEATURE:
<221> NAME/KEY: MISC_FEATURE
<222> LOCATION: (4)..(4)
<223> OTHER INFORMATION: Homocystein
<220> FEATURE:
<221> NAME/KEY: THIOETH
<222> LOCATION: (4)..(13)
<223> OTHER INFORMATION: Thioether bridge between residues 4 and 13
<220> FEATURE:
<221> NAME/KEY: MISC_FEATURE
<222> LOCATION: (13)..(13)
<223> OTHER INFORMATION: 2-amino-4-(acetylamino)butanoic acid

<400> SEQUENCE: 160

Lys Lys Lys Xaa Thr Pro Arg Gly Asp Thr Phe Ala Xaa Ala
1 5 10

<210> SEQ ID NO 161
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic
Peptide 160
<220> FEATURE:
<221> NAME/KEY: MISC_FEATURE
<222> LOCATION: (5)..(5)
<223> OTHER INFORMATION: Homocystein
<220> FEATURE:
<221> NAME/KEY: THIOETH
<222> LOCATION: (5)..(14)
<223> OTHER INFORMATION: Thioether bridge between residues 5 and 14
<220> FEATURE:
<221> NAME/KEY: MISC_FEATURE
<222> LOCATION: (14)..(14)
<223> OTHER INFORMATION: 2-amino-4-(acetylamino)butanoic acid

<400> SEQUENCE: 161

Lys Lys Lys Ala Xaa Thr Pro Arg Gly Asp Thr Phe Ala Xaa Ala
1 5 10 15

<210> SEQ ID NO 162
<211> LENGTH: 15
<212> TYPE: PRT
<213> ORGANISM: Artificial Sequence
<220> FEATURE:
<223> OTHER INFORMATION: Synthetic Sequence, Integrin-binding Cyclic Peptide 161
<220> FEATURE:
<221> NAME/KEY: MISC_FEATURE
<222> LOCATION: (5)..(5)
<223> OTHER INFORMATION: Homocystein
<220> FEATURE:
<221> NAME/KEY: THIOETH
<222> LOCATION: (5)..(14)
<223> OTHER INFORMATION: Thioether bridge between residues 5 and 14
<220> FEATURE:
<221> NAME/KEY: MISC_FEATURE
<222> LOCATION: (14)..(14)
<223> OTHER INFORMATION: 2-amino-4-(acetylamino)butanoic acid

<400> SEQUENCE: 162

Lys Lys Lys Ala Xaa Thr Thr Arg Gly Asp Ser Phe Ala Xaa Ala
1 5 10 15

<210> SEQ ID NO 163
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic Peptide 162
<220> FEATURE:
<221> NAME/KEY: MISC_FEATURE
<222> LOCATION: (5)..(5)
<223> OTHER INFORMATION: Homocystein
<220> FEATURE:
<221> NAME/KEY: THIOETH
<222> LOCATION: (5)..(14)
<223> OTHER INFORMATION: Thioether bridge between residues 5 and 14
<220> FEATURE:
<221> NAME/KEY: MISC_FEATURE
<222> LOCATION: (14)..(14)
<223> OTHER INFORMATION: 2-amino-4-(acetylamino)butanoic acid

<400> SEQUENCE: 163

Lys Lys Lys Ala Xaa Ile Pro Arg Gly Asp Ser Phe Ala Xaa
1 5 10

<210> SEQ ID NO 164
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic Peptide 163
<220> FEATURE:
<221> NAME/KEY: MISC_FEATURE
<222> LOCATION: (4)..(4)
<223> OTHER INFORMATION: Homocystein
<220> FEATURE:
<221> NAME/KEY: THIOETH
<222> LOCATION: (4)..(13)
<223> OTHER INFORMATION: Thioether bridge between residues 4 and 13
<220> FEATURE:
<221> NAME/KEY: MISC_FEATURE
<222> LOCATION: (13)..(13)
<223> OTHER INFORMATION: 2-amino-4-(acetylamino)butanoic acid

<400> SEQUENCE: 164

Lys Lys Lys Xaa Ile Pro Arg Gly Asp Ser Phe Ala Xaa Ala 1 5 10

<210> SEQ ID NO 165
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic Peptide 164
<220> FEATURE:
<221> NAME/KEY: MISC_FEATURE
<222> LOCATION: (5)..(5)
<223> OTHER INFORMATION: Homocystein
<220> FEATURE:
<221> NAME/KEY: THIOETH
<222> LOCATION: (5)..(14)
<223> OTHER INFORMATION: Thioether bridge between residues 5 and 14
<220> FEATURE:
<221> NAME/KEY: MISC_FEATURE
<222> LOCATION: (14)..(14)
<223> OTHER INFORMATION: 2-amino-4-(acetylamino)butanoic acid

<400> SEQUENCE: 165

Lys Lys Lys Ala Xaa Val Pro Arg Gly Asp Thr Phe Ala Xaa
1 5 10

<210> SEQ ID NO 166
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic Peptide 165
<220> FEATURE:
<221> NAME/KEY: MISC_FEATURE
<222> LOCATION: (4)..(4)
<223> OTHER INFORMATION: Homocystein
<220> FEATURE:
<221> NAME/KEY: THIOETH
<222> LOCATION: (4)..(13)
<223> OTHER INFORMATION: Thioether bridge between residues 4 and 13
<220> FEATURE:
<221> NAME/KEY: MISC_FEATURE
<222> LOCATION: (13)..(13)
<223> OTHER INFORMATION: 2-amino-4-(acetylamino)butanoic acid

<400> SEQUENCE: 166

Lys Lys Lys Xaa Val Pro Arg Gly Asp Thr Phe Ala Xaa Ala
1 5 10

<210> SEQ ID NO 167
<211> LENGTH: 14
<212> TYPE: PRT
<213> ORGANISM: Artificial Sequence
<220> FEATURE:
<223> OTHER INFORMATION: Synthetic Sequence, Integrin-binding Cyclic Peptide 166
<220> FEATURE:
<221> NAME/KEY: misc_feature
<222> LOCATION: (5)..(5)
<223> OTHER INFORMATION: 2-amino-3-(acetylamino)propanoic acid
<220> FEATURE:
<221> NAME/KEY: thioeth
<222> LOCATION: (5)..(14)
<223> OTHER INFORMATION: Thioether bridge between residues 5 and 14

<400> SEQUENCE: 167

Lys Lys Lys Ala Xaa Glu Pro Arg Gly Asp Asn Tyr Arg Cys
1 5 10

<210> SEQ ID NO 168
<211> LENGTH: 13

<212> TYPE: PRT
<213> ORGANISM: Artificial Sequence
<220> FEATURE:
<223> OTHER INFORMATION: Synthetic Sequence, Integrin-binding Cyclic
      Peptide 167
<220> FEATURE:
<221> NAME/KEY: misc_feature
<222> LOCATION: (4)..(4)
<223> OTHER INFORMATION: 2-amino-3-(acetylamino)propanoic acid
<220> FEATURE:
<221> NAME/KEY: thioeth
<222> LOCATION: (4)..(13)
<223> OTHER INFORMATION: Thioether bridge between residues 4 and 13

<400> SEQUENCE: 168

Lys Lys Lys Xaa Glu Pro Arg Gly Asp Asn Tyr Arg Cys
1               5                   10

<210> SEQ ID NO 169
<211> LENGTH: 7
<212> TYPE: PRT
<213> ORGANISM: Artificial Sequence
<220> FEATURE:
<223> OTHER INFORMATION: Synthetic Sequence, Region in Cyclic Segment

<400> SEQUENCE: 169

Ile Pro Arg Gly Asp Asn Phe
1               5

<210> SEQ ID NO 170
<211> LENGTH: 8
<212> TYPE: PRT
<213> ORGANISM: Artificial Sequence
<220> FEATURE:
<223> OTHER INFORMATION: Synthetic Sequence, Region in Cyclic Segment

<400> SEQUENCE: 170

Ile Pro Arg Gly Asp Ser Phe Ala
1               5

<210> SEQ ID NO 171
<211> LENGTH: 8
<212> TYPE: PRT
<213> ORGANISM: Artificial Sequence
<220> FEATURE:
<223> OTHER INFORMATION: Synthetic Sequence, Region in Cyclic Segment

<400> SEQUENCE: 171

Val Pro Arg Gly Asp Thr Phe Ala
1               5

<210> SEQ ID NO 172
<211> LENGTH: 8
<212> TYPE: PRT
<213> ORGANISM: Artificial Sequence
<220> FEATURE:
<223> OTHER INFORMATION: Synthetic Sequence, Region in Cyclic Segment

<400> SEQUENCE: 172

Thr Pro Arg Gly Asp Thr Phe Ala
1               5

<210> SEQ ID NO 173
<211> LENGTH: 10
<212> TYPE: PRT
<213> ORGANISM: Artificial Sequence
<220> FEATURE:
<223> OTHER INFORMATION: Synthetic sequence -continued

```
<400> SEQUENCE: 173

Ala Tyr His Arg Gly Glu Leu Val Trp Glu
1               5                   10


<210> SEQ ID NO 174
<211> LENGTH: 9
<212> TYPE: PRT
<213> ORGANISM: Artificial Sequence
<220> FEATURE:
<223> OTHER INFORMATION: Synthetic sequence

<400> SEQUENCE: 174

Ser Ala Trp His Gly Glu Leu Val Trp
1               5
```

CYCLIC PEPTIDE, CELL SCAFFOLD MATERIAL, CELL SEPARATING MATERIAL, AND MEDIUM

CROSS-REFERENCE TO RELATED APPLICATION

This application is a Continuation of International Application No. PCT/JP2020/022558, filed Jun. 8, 2020, which claims priority to Japanese Patent Application No. 2019-108962 filed Jun. 11, 2019. Each of the above applications is hereby expressly incorporated by reference, in its entirety, into the present application.

BACKGROUND OF THE INVENTION

1. Field of the Invention

The present disclosure relates to a cyclic peptide, a cell scaffold material, a cell separating material, and a medium.

2. Description of the Related Art

Integrin is a cell adhesion molecule and is a heterodimeric protein consisting of two subunits, an α chain and a β chain. Integrin plays an important role not only in cell adhesion but also in cel extension, cell migration, cell proliferation, tissue formation, cancer metastasis, tissue repair, blood coagulation, and the like.

JP2005-507376A discloses a cyclic peptide that is cyclized by a disulfide bond and that binds to integrin. Other cyclic peptides having an affinity to integrin are also known. For example, JP1994-509551A (JP-H6-509551A) discloses a cyclic peptide obtained by cyclizing Tyr-Arg-Gly-Asp, as a platelet aggregation inhibitor having high specificity to GP $II_b$ $III_a$. In addition, Bioconjugate Chem., 1995, 6, p. 269-277 describes a technique for subjecting a peptide to cyclization and/or binding to a carrier protein or glass coverslip using (bromoacetyl) diaminopropionic acid.

SUMMARY OF THE INVENTION

An object to be achieved by an aspect according to the present disclosure is to provide a cyclic peptide excellent in the binding property to integrin and excellent in the molecule stability, for example, in the alkali resistance, and a cell scaffold material, a cell separating material, and a medium, which contain the cyclic peptide.

The technique for achieving the above object includes the following aspects.

<1> A cyclic peptide comprising:

a cyclic segment comprising an RGD sequence and having 8 to 14 amino acid residues, a thioether bond being formed between an amino acid residue $X^a$ located on a most N-terminal side of the cyclic segment and an amino acid residue $X^b$ located on a most C-terminal side of the cyclic segment, provided that, in a case where one of the amino acid residue $X^a$ and the amino acid residue $X^b$ is a cysteine residue, an α carbon of the other amino acid residue of the amino acid residue $X^a$ and the amino acid residue $X^b$ is separated from a sulfur atom of the cysteine residue by five or more atoms.

<2> The cyclic peptide according to <1>, further comprising at least one of a first segment between the cyclic segment and an N-terminal of the cyclic peptide or a second segment between the cyclic segment and a C-terminal of the cyclic peptide, in which the at least one of the first segment or the second segment comprises an amino acid residue having an immobilizing functional group in a side chain.

<3> The cyclic peptide according to <2>, in which the immobilizing functional group is an amino group or a thiol group.

<4> The cyclic peptide according to <2>, in which the amino acid residue having the immobilizing functional group in a side chain is selected from the group consisting of an L-lysine residue, a D-lysine residue, an L-cysteine residue, a D-cysteine residue, an L-homocysteine residue, and a D-homocysteine residue.

<5> The cyclic peptide according to any one of <2> to <4>, in which, in a case of being present, each of the first segment and the second segment has a length of 1 to 20 amino acid residues.

<6> The cyclic peptide according to any one of <1> to <5>, in which one of the amino acid residue $X^a$ and the amino acid residue $X^b$ is an amino acid residue of the following (p) or (q), (p)

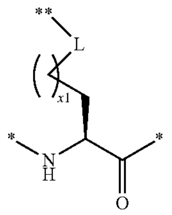

(q)

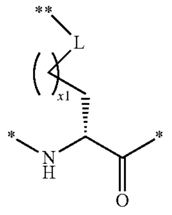

wherein * is a bonding site to an adjacent amino acid residue; ** is a bonding site to a sulfur atom of an amino acid residue which is a counterpart in the thioether bond; x1 is an integer of 0 or more; x1 pieces of carbon atoms and a carbon atom at a β-position may be substituted with one or more substituents selected from the group consisting of $—NH_2$, —SH, —COOH, a $C_1$-$C_{10}$ alkyl group, and a $C_6$-$C_{14}$ aryl group;

-L is $—(CH_2)_{y1}—C(=O)—$ or $**—(CH_2)_{y1}—C(=O)—NH—$, where y1 represents an integer of 0 or more and 10 or less; and the other of the amino acid residue $X^a$ and the amino acid residue $X^b$ is an residue of the following (t) or (u), and (t)

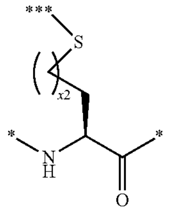

-continued (u)

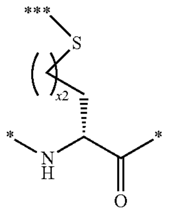

wherein * is a bonding site to an adjacent amino acid residue; *** is a bonding site to a carbon atom of an amino acid residue which is a counterpart in the thioether bond; x2 is an integer of 0 or more; and x2 pieces of carbon atoms and a carbon atom at a β-position may be substituted with one or more substituents selected from the group consisting of $—NH_2$, —SH, —COOH, a $C_1$-$C_{10}$ alkyl group, and a $C_6$-$C_{14}$ aryl group;

provided that, in a case where one of the amino acid residue $X^a$ and the amino acid residue $X^b$ is an amino acid residue of the (p) or the (q), in which x1 is 0, the other of the amino acid residue $X^a$ and the amino acid residue $X^b$ is not an L-cysteine residue or a D-cysteine residue.

<7> The cyclic peptide according to <6>, in which the amino acid residue $X^a$ is the amino acid residue of the (p) or the (q).

<8> The cyclic peptide according to <6>, in which the amino acid residue $X^b$ is the amino acid residue of the (p) or the (q).

<9> The cyclic peptide according to any one of <6> to <8>, in which the amino acid residue of the (p) or the (q) is a residue selected from the following (a) to (h):

(a)

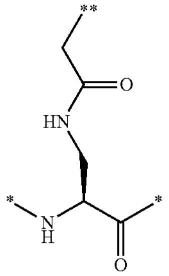

(b)

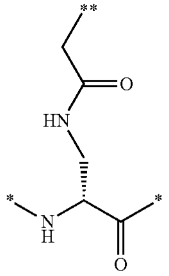

-continued (c)

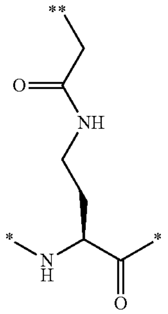

(d)

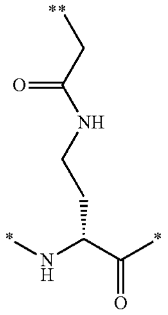

(e)

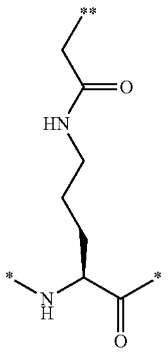

(f)

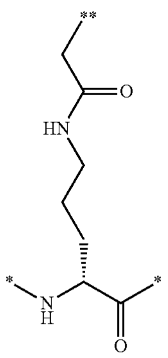

-continued (g)

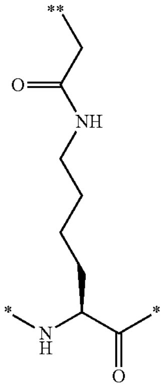

(h)

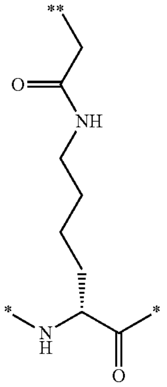

wherein * is a bonding site to an adjacent amino acid residue; ** is a bonding site to a sulfur atom of an amino acid residue which is a counterpart in the thioether bond; and the amino acid residue of the (t) or the (u) is selected from the group consisting of an L-homocysteine residue, a D-homocysteine residue, an L-penicillamine residue, a D-penicillamine residue, an L-cysteine residue, and a D-cysteine residue;

provided that a combination of the residue of the (a) or the (b) and an L-cysteine residue or a D-cysteine residue is excluded.

<10> The cyclic peptide according to any one of <1> to <9>, in which the cyclic peptide comprises a plurality of the cyclic segments, and the amino acid sequences of the respective cyclic segments may be the same or different from each other.

<11> The cyclic peptide according to <10>, in which the plurality of the cyclic segments are connected to each other by a connecting moiety having a length of 1 to 20 amino acid residues.

<12> The cyclic peptide according to any one of <1> to <11>, in which a total number of amino acid residues is 8 to 50.

<13> The cyclic peptide according to any one of <1> to <9>, in which the cyclic peptide is represented by Formula II:

Formula II $$R^N-X_{v0}-X^6_{t0}-X_{p0}-X^a-X_m-R-G-D-X_n-X^b-X_{q0}-X^7_{u0}-X_{w0}-Rc$$

in Formula II, $X^a$ represents the amino acid residue $X^a$, $X^b$ represents the amino acid residue $X^b$;

X represents any amino acid residue, where in a case where a plurality of X's are present, the plurality of X's may be the same or different from each other;

$R^N$ represents an N-terminal group; $R^C$ represents a C-terminal group;

$X^6$ and $X^7$ each independently represent an amino acid residue having an immobilizing functional group in a side chain, where in a case where a plurality of $X^6$'s or $X^7$'s are present, the plurality of $X^6$'s or $X^7$'s may be the same or different from each other;

m and n are integers and simultaneously satisfy $0 \le m \le 9$, $0 \le n \le 9$, and $3 \le m+n \le 9$;

p0 and q0 are integers and respectively satisfy $0 \le p0 \le 15$ and $0 \le q0 \le 15$;

t0 and u0 are integers and respectively satisfy $0 \le t0 \le 5$ and $0 \le u0 \le 5$;

v0 and w0 are integers and respectively satisfy $0 \le v0 \le 5$ and $0 \le w0 \le 5$; and p0, q0, t0, u0, v0, and w0 further satisfy $0 \le p0+q0+t0+u0+v0+w0 \le 39$.

<14> The cyclic peptide according to <13>, in which $X^a$—$X_m$—R-G-D-$X_n$—$X^b$ in Formula II is $X^a$—$X^t_{v5}$—$X^1$—$X^2$—R-G-D-$X^3$—$X^4$—$X^5_{v6}$—$X^t_{v7}$—$X^b$, where $X^t$ represents any amino acid residue, and in a case a plurality of $X^t$'s are present, the plurality of $X^t$'s may be the same or different from each other; $X^1$ represents I, V, D, E, Y, L, T, or homotyrosine; $X^2$ represents P, T, or S; $X^3$ represents N, S, T, V, A or homoserine; $X^4$ represents F, Y, or P; $X^5$ represents R, D, E, A, T, S, or G; v5 and v7 each independently represent an integer of 0 to 6; and v6 represents 0 or 1.

<15> The cyclic peptide according to <14>, in which the cyclic peptide satisfies at least one selected from the group consisting of the following (i) to (v);

(i) an amino acid residue represented by $X^1$ is I, V, or T, (ii) an amino acid residue represented by $X^2$ is P, (iii) an amino acid residue represented by $X^3$ is S or T, (iv) an amino acid residue represented by $X^4$ is F, and (v) v6 represents 1, and an amino acid residue represented by $X^5$ is A.

<16> The cyclic peptide according to any one of <1> to <15>, in which an amino acid sequence of a region which resides between the amino acid residue $X^a$ and the amino acid residue $X^b$ has 70% or more of a sequence identity with respect to an amino acid sequence of IPRGDNFR (SEQ ID NO: 1) or has 70% or more of a sequence identity with respect to any one of amino acid sequences of IPRGDSFA (SEQ ID NO: 170), VPRGDTFA (SEQ ID NO: 171), or TPRGDTFA (SEQ ID NO: 172).

<17> A cell scaffold material comprising a base material and the cyclic peptide according to any one of <1> to <16>.

<18> A cell separating material comprising a holding material and the cyclic peptide according to any one of <1> to <16>.

<19> A medium comprising a culture component and the cyclic peptide according to any one of <1> to <16>.

According to an aspect according to the present disclosure, there is provided a cyclic peptide excellent in the binding property to integrin and excellent in the molecule stability, for example, in the alkali resistance, and a cell scaffold material, a cell separating material, and a medium, which contain the cyclic peptide.

DESCRIPTION OF THE PREFERRED EMBODIMENTS

Hereinafter, a cyclic peptide, a cell scaffold material, a cell separating material, and a medium according to the present disclosure will be described. However, the embodiments according to the present disclosure are not limited to the following embodiments and can be implemented with appropriate modifications.

A range of numerical values shown using "to" in the disclosure means a range including numerical values before and after "to" as a minimum value and a maximum value.

In the range of numerical values disclosed stepwise in the present disclosure, an upper limit value and a lower limit value disclosed in a certain range of numerical values may be replaced with an upper limit value and a lower limit value disclosed in another range of numerical values disclosed in stepwise. In addition, in the range of numerical values disclosed in the present disclosure, an upper limit value and a lower limit value disclosed in a certain range of numerical values may be replaced with values shown in examples.

In the present disclosure, a combination of two or more preferred aspects is a more preferred aspect.

In the present disclosure, in a case where a plurality of substances corresponding to each component are present, unless otherwise particularly specified, the amount of each of components means the total amount of the plurality of substances.

In the present disclosure, the term "process" includes not only an independent process but also a process that cannot be clearly distinguished from other processes, as long as the intended purpose of the process is achieved.

The cyclic peptide according to the present disclosure contains a cyclic segment containing an RGD sequence and having 8 to 14 amino acid residues, in which a thioether bond is formed between an amino acid residue $X^a$ located on a most N-terminal side of the cyclic segment and an amino acid residue $X^b$ located on a most C-terminal side of the cyclic segment.

However, in a case where one of the amino acid residue $X^a$ and the amino acid residue $X^b$ is a cysteine residue, an α carbon of the other amino acid residue of the amino acid residue $X^a$ and the amino acid residue $X^b$ is separated from a sulfur atom of the cysteine residue by five or more atoms.

An integrin-binding cyclic peptide has an ability to bind to integrin which is a cell adhesion molecule. Since the integrin-binding cyclic peptide has an ability to bind to integrin on the cell surface, it can be used as a scaffolding material for cell culture, as a cell separating material for cell separation, and as a medium, and thus is a useful molecule. However, while a cyclic peptide may have a high binding property and a high specificity as compared with a linear peptide, the molecule stability of the cyclic peptide tends to be low as compared with the linear peptide.

For example, a cyclic peptide tends to have low alkali resistance; low acid resistance; and low resistance to actinic rays such as an X ray and a γ ray. The integrin-binding cyclic peptide is also degraded during long-term use or repeated use due to low molecule stability thereof, and thus the desired effect could not be obtained for a long period of time. Furthermore, a cyclic peptide does not always have a higher binding property than a linear peptide, and the binding property to integrin changes depending on the amino acid sequence of the cyclic peptide. As a result, it has not been easy to obtain an integrin-binding cyclic peptide having both an excellent molecule stability and an excellent integrin binding property.

However, the cyclic peptide having a specific structure according to the present disclosure has both an excellent molecule stability and an excellent integrin binding property. The cyclic peptide having a specific structure according to the present disclosure contains a cyclic segment containing an RGD sequence and having 8 to 14 amino acid residues, in which a thioether bond is formed between an amino acid residue $X^a$ located on a most N-terminal side of the cyclic segment and an amino acid residue $X^b$ located on a most C-terminal side of the cyclic segment. However, in a case where one of the amino acid residue $X^a$ and the amino acid residue $X^b$ is a cysteine residue, an α carbon of the other amino acid residue of the amino acid residue $X^a$ and the amino acid residue $X^b$ is separated from a sulfur atom of the cysteine residue by five or more atoms. Due to this specific structure, the cyclic peptide having a specific structure according to the present disclosure has an excellent molecule stability and an excellent integrin binding property. However, JP2005-507376A, JP1994-509551A (JP-H6-509551A), and Bioconjugate Chem., 1995, 6, p. 269-277 do not disclose that in a case where amino acid residues involved in a thioether bond in a cyclic peptide are set to satisfy the above-described regulations while setting a cyclic segment region to satisfy the above-described regulations, both an excellent molecule stability and an excellent integrin binding property are achieved.

<Amino Acid and Amino Acid Residue>

In the present disclosure, an amino acid is represented by, in principle, using the name, the abbreviation, and the like adopted by INTERNATIONAL UNION OF PURE AND APPLIED CHEMISTRY and INTERNATIONAL UNION OF BIOCHEMISTRY AND MOLECULAR BIOLOGY IUPAC-IUB Joint Commission on Chemical Nomenclature (JCBN). In addition, an amino acid residue is represented by using an abbreviation of an amino acid from which the amino acid residue is derived.

Unless otherwise specified, an amino acid sequence (also referred to as a "primary structure") of a peptide or protein is represented so that amino acid residues are aligned in a row from the N-terminal to the C-terminal from the left end to the right end. In a case where an amino acid residue in the amino acid sequence of a peptide or protein, including the position thereof, is specified, it may be represented by adding a number indicating the number of the amino acid residue from the N-terminal side to the right side of the abbreviation of the amino acid residue. For example, the lysine at the second position from the N-terminal may be represented as Lys2.

In addition, in a case where an amino acid is represented using the name thereof, and isomers having an enantiomeric relationship, that is, an L-form and a D-form are present, the amino acid may be, in principle, the L-form or the D-form except for the case where the distinction between the L-form and the D-form is explicitly shown. For example, "isoleucine" represents "L-isoleucine" or "D-isoleucine", and the same applies to the amino acid residue. Similarly, also in a case where an amino acid is represented using the abbreviation (the three letter abbreviation or the one letter abbreviation) thereof, and isomers having an enantiomeric relationship, that is, an L-form and a D-form are present, the amino acid may be, in principle, the L-form or the D-form except for the case where the distinction between the L-form and the D-form is explicitly shown. For example, "Lys" represents both "L-lysine" and "D-lysine", and the same applies to the amino acid residue. In addition, the L-form and the D-form can be each independently selected for each amino acid and each amino acid residue. However, in the RGD sequence present in the cyclic segment, all amino acid residues have an L-form. Except for the above RGD sequence, all the amino acid residues present in the cyclic peptide may be amino acid residues having an L-form or may be amino acid residues having a D-form, or both amino acid residues having an L-form and amino acid residues having a D-form may be present.

In addition, in a case where an amino acid is represented by a name thereof, and an isomer having a diastereomeric relationship is present, the isomer is not included in the amino acid specified by the name. The prefix "allo" is used to treat a diastereomer as a different kind of amino acid. For example, "threonine" does not include "allothreonine". The same applies to the amino acid residue.

Table 1 shows names and abbreviations (one letter abbreviations and three letter abbreviations) of amino acids for which one letter abbreviations and three letter abbreviations are officially approved.

TABLE 1

| One letter abbreviation | Three letter abbreviation | Name |
|---|---|---|
| A | Ala | Alanine |
| B | Asx | Aspartic acid or asparagine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| O | Pyl | Pyrrolysine |
| P | Pro | Proline |
| Q | Gln | Glutamine |
| R | Arg | Arginine |
| S | Ser | Serine |
| T | Thr | Threonine |
| U | Sec | Selenocysteine |
| V | Val | Valine |
| W | Trp | Tryptophan |
| X | Xaa | Any amino acid |
| Y | Tyr | Tyrosine |
| Z | Glx | Glutamic acid or glutamine |

Amino acids that are capable of being used in the cyclic peptide according to the present disclosure are not limited to the amino acids listed in Table 1, and unusual amino acids can also be used. Examples of the unusual amino acids are listed in Table 2 below; however, the unusual amino acids are not limited thereto.

TABLE 2

| Three letter abbreviation | Name |
|---|---|
| Aad | Homeglutamic acid |
| βAad | 3-aminoadipic acid |
| Abu | 2-aminobutanoic acid |
| $A_2$bu | 2,4-diaminobutanoic acid |
| Ahx | 2-aminohexanoic acid |
| Ahe | 2-aminoheptanoic acid |
| Aib | 2-aminoisobutyric acid |
| εAhx | 6-aminohexanoic acid |
| βAla | β-alanine |
| Ape | 2-aminopentanoic acid |
| $A_2$pr | 2,3-diaminopropanoic acid |
| Apm | 2-aminopimelic acid |

TABLE 2-continued

| Three letter abbreviation | Name |
|---|---|
| $A_2$pm | 2,6-diaminopimelic acid |
| Cit | Citrulline |
| Cya | Cysteic acid |
| Dbu | 2,4-diaminobutanoic acid |
| Dpm | 2,6-diaminopimelic acid |
| Pen | Penicillamine |
| Dpr | 2,3-diaminopropanoic acid |
| Gla | 4-carboxyglutamic acid |
| Glp | 5-oxoproline |
| Hcy | Homocysteine |
| Hly | Homolysine |
| Hse | Homoserine |
| Hsl | Homoserine lactone |
| 5Hyl | 5-hydroxylysine (Hyl) |
| aHyl | Allohydoxylysine |
| 3Hyp | 3-hydroxyproline |
| 4Hyp | 4-hydroxyproline |
| aIle | Alloisoleucine |
| Nle | Norleucine |
| Nva | Norvaline |
| Orn | Ornithine |
| Sar | Sarcosine |
| aThr | Allothreonine |
| Thx | Thyroxine |

Any amino acid residue contained in the cyclic peptide according to the present disclosure may be chemically modified. Examples of the chemical modification of an amino acid residue include N-acetylation, N-formylation, N-acylation, PEGylation, or the like of an amino group present in the amino acid residue and amidation, PEGylation, or the like of a carboxyl group present in the amino acid residue.

The cyclic peptide according to the present disclosure contains a cyclic segment containing an RGD sequence and having 8 to 14 amino acid residues, in which a ring is formed by the crosslinking between an amino acid residue $X^a$ located on a most N-terminal side of the cyclic segment and an amino acid residue $X^b$ located on a most C-terminal side of the cyclic segment. The cyclic peptide according to the present disclosure may consist of only a cyclic segment or may have an additional amino acid residue on at least one of the N-terminal side or the C-terminal side of the cyclic segment.

In addition, in the cyclic peptide according to the present disclosure, the number of the cyclic segments is not limited to 1, and a plurality of the cyclic segments, that is, two or more thereof may be present. In a case where a plurality of cyclic segments are present, the number of cyclic segments in the cyclic peptide according to the present disclosure may be 2 to 4, may be 2 or 3, or may be 2. The amino acid sequences of the plurality of cyclic segments may be the same or different from each other. Further, a cyclic segment and an adjacent cyclic segment may be directly connected, or an amino acid sequence serving as a connecting moiety may be present between the cyclic segment and the adjacent cyclic segment. In a case where an amino acid sequence serving as a connecting moiety is present, the amino acid sequence as the connecting moiety is not particularly limited; however, the length of each connecting moiety may be 1 to 20 amino acid residues, a may be 2 to 10 amino acid residues, and may be 3 to 5 amino acid residues.

The above cyclic segment contains an RGD sequence. In the present disclosure, the term "cyclic segment" is used for the cyclic segment in which the above RGD sequence is contained and the number of amino acid residues is 8 to 14; however, it does not matter whether a cyclic moiety which does not correspond to the cyclic moiety having an RGD sequence and having 8 to 14 amino acid residues, for example, a cyclic moiety that does not contain an RGD sequence or a cyclic moiety in which the number of amino acid residues is outside a range of 8 to 14, is additionally present.

Since the RGD sequence is a sequence required for binding to an integrin, the above cyclic peptide is composed so that the above cyclic segment contains the RGD sequence. However, in order for the RGD sequence to fully exhibit an ability to bind to integrin, it is necessary that amino acid residues are present around the RGD sequence as well, and the cyclic segment is composed so that the number of amino acid residue is 8 to 14. The number of RGD sequences present in one cyclic segment may be one, or two, three, or four RGD sequences may be present therein. The position of the RGD sequence in the cyclic segment is preferably a position to which none of the amino acid residue $X^a$ and the amino acid residue $X^b$ is adjacent. In other words, it is preferable that one or more amino acid residues are present between the RGD sequence and the amino acid residue $X^a$, and it is also preferable that one or more amino acid residues are present between the RGD sequence and the amino acid residue $X^b$. For example, it is preferable that, in a case where amino acid residues are counted toward the C terminal side with setting the amino acid residue $X^a$ as the first amino acid residue, the RGD sequence corresponds to the 3rd to 5th amino acid residues or corresponds the 4th to 6th amino acid residues from the viewpoint of increasing the binding property to integrin.

The number of amino acid residues in the cyclic segment is 8 to 14 as described above. The number of amino acid residues in the cyclic segment may be 9 to 13 or may be 10 to 12. In a case where the number of amino acid residues in the cyclic segment is within this range, the intramolecular strain of the cyclic peptide does not become too large and the higher-order structure such as a helix is stabilized, and thus the cyclic peptide according to the present disclosure has an excellent integrin binding property.

Amino acid residues other than the RGD sequence, the amino acid residue represented by $X^a$, and the amino acid residue represented by $X^b$ in the cyclic segment are not particularly limited as long as the binding property to integrin is not impaired. Each of the amino acid residues other than the RGD sequence, the amino acid residue represented by $X^a$, and the amino acid residue represented by $X^b$ in the cyclic segment may be an amino acid residue selected from an isoleucine residue, a valine residue, an aspartic acid residue, a glutamic acid residue, a tyrosine residue, a leucine residue, a threonine residue, a homotyrosine residue, a proline residue, a serine residue, an asparagine residue, an alanine residue, a homoserine residue, a phenylalanine residue, an arginine residue, and a glycine residue. The number of the amino acid residues other than the RGD sequence, the amino acid residue represented by $X^a$, and the amino acid residue represented by $X^b$ in the cyclic segment is 3 to 9, may be 4 to 8, or may be 5 to 7 in a case where one RGD sequence is contained in the cyclic segment.

For example, the cyclic segment may be a cyclic segment represented by (Formula III)

$$X^a—X^t_{v5}—X^{11}—X^{21}—R—G—D—X^{31}—X^{41}—X^{51}_{v6}—X^t_{v7}—X^b.$$

In Formula III;

$X^a$ represents an amino acid residue $X^a$ located on the most N-terminal side of the cyclic segment, and $X^b$ represents an amino acid residue $X^b$ located on the most C-terminal side of the cyclic segment, where $X^t$ represents any amino acid residue, and in a case a plurality of $X^t$'s are present, the plurality of $X^t$'s may be the same or different from each other, $X^{11}$, $X^{21}$, $X^{31}$, $X^{41}$, and $X^{51}$ each independently represent any one of amino acid residues, v5 and v7 each independently represent an integer of 0 to 6, and v6 represents 0 or 1.

However, at least one selected from the group consisting of the following (a) to (e) is satisfied.

(a) $X^{11}$ represents I, V, D, E, Y, L, T, or homotyrosine.

(b) $X^{21}$ represents P, T, or S.

(c) $X^{31}$ represents N, S, T, V, A or homoserine.

(d) $X^{41}$ represents F, Y, or P.

(e) v6 is 1, and $X^{51}$ represents R, D, E, A, T, S, or G.

Preferred examples of $X^a$ and $X^b$ in Formula (III) will be described later. v5 and v7 may be each independently 0 to 4, 0 to 2, 0 or 1, or 0. In addition, $X^t$'s may be each independently an amino acid residue selected from the group consisting of A, F, G, I, L, M, P, V, and W, may be an amino acid residue selected from the group consisting of A, G, I, L, P, and V, and may be A.

More specifically, for example, the cyclic segment may be a cyclic segment represented by (Formula IV)

$$X^a—X^t_{v5}—X^1—X^2—R—G—D—X^3—X^4—X^5_{v6}—X^t_{v7}—X^b.$$

In Formula IV, $X^a$ represents an amino acid residue $X^a$ located on the most N-terminal side of the cyclic segment, $X^b$ represents an amino acid residue $X^b$ located on the most C-terminal side of the cyclic segment, where $X^t$ represents any amino acid residue, and in a case a plurality of $X^t$'s are present, the plurality of $X^t$'s may be the same or different from each other, $X^1$ represents I, V, D, E, Y, L, T, or homotyrosine, $X^2$ represents P, T, or S, $X^3$ represents N, S, T, V, A or homoserine, $X^4$ represents F, Y, or P, $X^5$ represents R, D, E, A, T, S, or G, v5 and v7 each independently represent an integer of 0 to 6, and v6 represents 0 or 1.

Preferred examples of $X^a$ and $X^b$ will be described later. v5 and v7 may be each independently 0 to 4, 0 to 2, 0 or 1, or 0. In addition, $X^t$'s may be each independently an amino acid residue selected from the group consisting of A, F, G, I, L, M, P, V, and W, may be an amino acid residue selected from the group consisting of A, G, I, L, P, and V, and may be A.

An amino acid residue represented by $X^1$ may be I, V, or T.

An amino acid residue represented by $X^2$ may be P.

An amino acid residue represented by $X^3$ may be S or T.

An amino acid residue represented by $X^4$ may be F. In a case where v6 represents 1, the amino acid residue represented by $X^5$ may be A. In addition, in the exemplary regulations of these amino acid residue candidates for $X^1$ to $X^5$, at least one of the above may be satisfied; however, two or more of the above may be combined, and all of the above may be combined.

In the cyclic segment, the amino acid sequence of a region which resides between the amino acid residue $X^a$ and the amino acid residue $X^b$ may be the same sequence as the amino acid sequence of IPRGDNFR (SEQ ID NO: 1) or may be an amino acid residue in which an amino acid residue is added, deleted, or substituted with respect to the amino acid sequence of SEQ ID NO: 1. However, the RGD region in SEQ ID NO: 1 should not be modified. In a case of adding amino acid residues to the inside of the amino acid sequence of SEQ ID NO: 1, the total number of amino acid residues to be added is preferably 1 to 5, more preferably 1 to 3, and still more preferably 1 or 2. In a case of adding amino acid residues to the outside of the amino acid sequence of SEQ ID NO: 1, that is, to at least one of a region between the amino acid residue $X^a$ and the N-terminal I residue of SEQ ID NO: 1 or a region between the amino acid residue $X^b$ and the C-terminal R residue of SEQ ID NO: 1, the total number of amino acids to be added is preferably 1 to 10, more preferably 1 to 5, and still more preferably 1 to 3. In a case of deleting amino acid residues of the inside of the amino acid sequence of SEQ ID NO: 1, the total number of amino acid residues to be deleted is preferably 1 to 3, more preferably 1 or 2, and still more preferably 1. In a case of substituting amino acid residues of the inside of the amino acid sequence of SEQ ID NO: 1 with another amino acid residue, the total number of amino acid residues to be substituted is preferably 1 to 5, more preferably 1 to 3, and still more preferably 1 or 2.

In the cyclic segment, the amino acid sequence of a region which resides between the amino acid residue $X^a$ and the amino acid residue $X^b$ may include two or more of the addition, the deletion, and the substitution of amino acid residues as compared with the amino acid sequence of SEQ ID NO: 1. The total number of amino acid residues to be added, deleted, or substituted is preferably 1 to 15, more preferably 1 to 10, still more preferably 1 to 5, and even still more preferably 1 to 3. In a case where amino acid residues are to be added or deleted, it is preferable to carry out the addition or deletion at the terminal of the amino acid sequence of SEQ ID NO: 1. The same applies to the sequence of the region which resides between two crosslinked amino acid residues (that is, the amino acid residues $X^a$ and $X^b$) in the cyclic segment in the amino acid sequences of SEQ ID NOs: 2 to 166 described later.

For example, it is preferable that the deletion of amino acid residues occurs at the C-terminal R residue in the amino acid sequence of SEQ ID NO: 1.

In the cyclic segment, the amino acid sequence of a region which resides between the amino acid residue $X^a$ and the amino acid residue $X^b$ preferably has a sequence identity of 70% or more with respect to the amino acid sequence of IPRGDNFR (SEQ ID NO: 1). The amino acid sequence of a region which resides between the amino acid residue $X^a$ and the amino acid residue $X^b$ preferably has 70% or more of a sequence identity, more preferably has a sequence identity of 80% or more, and still more preferably has a sequence identity of 85% or more, with respect to the amino acid sequence of IPRGDNFR (SEQ ID NO: 1). Here, the range of the amino acid sequence having a sequence identity of 70% or more with respect to the amino acid sequence of IPRGDNFR (SEQ ID NO: 1) includes the amino acid sequence of IPRGDNFR (SEQ ID NO: 1) itself.

In the present disclosure, the sequence identity between two amino acid sequences is determined as follows.

(i) Two Amino Acid Sequences are Aligned.

The alignment of the two sequences can be carried out using, for example, an alignment algorithm and/or a program, such as FASTA or BLAST that can be used by default settings.

(ii) a Sequence Identity is Calculated.

Based on the obtained alignment, the sequence identity is calculated by the following expression.

The sequence identity [%]=(the number of matching positions/the total number of positions)×100 [%]

The total number of positions is the length of the alignment, and the number of matching positions is the number of positions where the kinds of amino acids match.

(iii) Calculation Example of Sequence Identity

For example, the following amino acid sequences are assumed.

```
Array A:
                                    (SEQ ID NO: 173)
AYHRGELVWE

Array B:
                                    (SEQ ID NO: 174)
SAWHGELVW
```

In a case where these are aligned under the above conditions, the result becomes as follows. Here, a symbol "|" is assigned to a place where the kind of amino acid (residue) matches between the sequences A and B for visual convenience. In addition, "-" indicates a place where there is no corresponding amino acid.

```
Array A: -AYHRGELVWE (SEQ ID NO: 173)
            || | |||||
Array B: SAWH-GELVW- (SEQ ID NO: 174)
```

In this example, the total number of positions is 11, and the number of matching positions is 7, and thus the sequence identity calculated according to the above expression is, 7/11×100=63.6%.

In the above, the number of amino acid residues to be added, deleted, or substituted with respect to the amino acid sequence of SEQ ID NO: 1 and the sequence identity to the amino acid sequence of SEQ ID NO: 1 have been described. However, the regulation of the number of amino acid residues to be added, deleted, or substituted with respect to the above amino acid sequence and the regulation of the sequence identity can be applied in the same manner to the case where the sequence of the region which resides between two crosslinked amino acid residues (that is, the amino acid residues $X^a$ and $X^b$) in the cyclic segment in the amino acid sequences of SEQ ID NOs: 2 to 166 (that is, the amino acid sequences of the cyclic peptides 1 to 165) is set as the reference sequence. For example, the regulation of the number of amino acid residues to be added, deleted, or substituted with respect to the above amino acid sequence and the regulation of the sequence identity can be applied in the same manner to the amino acid sequence of IPRGDNF (SEQ ID NO: 169), which is a region between the homocysteine residue and the 2-amino-4-acetylamino-butanoic acid residue in the cyclic peptide 10.

For example, in the cyclic segment, the amino acid sequence of a region which resides between the amino acid residue $X^a$ and the amino acid residue $X^b$ may be the same sequence as any one of the amino acid sequences of IPRGDSFA (SEQ ID NO: 170), VPRGDTFA (SEQ ID NO:

171), and TPRGDTFA (SEQ ID NO: 172), or may be an amino acid residue in which an amino acid residue is added, deleted, or substituted with respect to any one of the amino acid sequences of SEQ ID NOs: 170 to 172. However, the RGD region in SEQ ID NOs: 170 to 172 should not be modified. In a case of adding amino acid residues to the inside of any one of the amino acid sequences of SEQ ID NOs: 170 to 172, the total number of amino acid residues to be added is preferably 1 to 5, more preferably 1 to 3, and still more preferably 1 or 2. In a case of adding amino acid residues to the outside of any one of the amino acid sequences of SEQ ID NOs: 170 to 172, that is, to at least one of a region between the amino acid residue $X^a$ and the N-terminal residue of any one SEQ ID NOs: 170 to 172 or a region between the amino acid residue $X^b$ and the C-terminal residue of any one of SEQ ID NOs: 170 to 172, the total number of amino acids to be added is preferably 1 to 10, more preferably 1 to 5, and still more preferably 1 to 3. In a case of deleting amino acid residues of the inside of any one of the amino acid sequences of SEQ ID NOs: 170 to 172, the total number of amino acid residues to be deleted is preferably 1 to 3, more preferably 1 or 2, and still more preferably 1. In a case of substituting amino acid residues of the inside of any one of the amino acid sequences of SEQ ID NOs: 170 to 172 with another amino acid residue, the total number of amino acid residues to be substituted is preferably 1 to 5, more preferably 1 to 3, and still more preferably 1 or 2.

In the cyclic segment, the amino acid sequence of a region which resides between the amino acid residue $X^a$ and the amino acid residue $X^b$ may include two or more of the addition, the deletion, and the substitution of amino acid residues as compared with any one of the amino acid sequences of SEQ ID NOs: 170 to 172. The total number of amino acid residues to be added, deleted, or substituted is preferably 1 to 15, more preferably 1 to 10, still more preferably 1 to 5, and even still more preferably 1 to 3. In a case where amino acid residues are to be added or deleted, it is preferable to carry out the addition or deletion at the terminal of any one of the amino acid sequences of SEQ ID NOs: 170 to 172.

For example, it is preferable that the deletion of amino acid residues occurs at the C-terminal residue in any one of the amino acid sequences of SEQ ID NOs: 170 to 172.

In the cyclic segment, it is preferable that the amino acid sequence of a region which resides between the amino acid residue $X^a$ and the amino acid residue $X^b$ has a sequence identity of 70% or more with respect to any one of the amino acid sequences of IPRGDSFA (SEQ ID NO: 170), VPRGDTFA (SEQ ID NO: 171), or TPRGDTFA (SEQ ID NO: 172). The amino acid sequence of a region which resides between the amino acid residue $X^a$ and the amino acid residue $X^b$ preferably has 70% or more of a sequence identity, more preferably has a sequence identity of 80% or more, and still more preferably has a sequence identity of 85% or more, with respect to any one of the amino acid sequences of SEQ ID NOs: 170 to 172. Here, the range of the amino acid sequence having a sequence identity of 70% or more with respect to any one of the amino acid sequences of SEQ ID NOs: 170 to 172 includes any one of the amino acid sequences of SEQ ID NOs: 170 to 172 itself The total length (the total number of amino acid residues) of the cyclic peptide according to the present disclosure, which contains a cyclic segment, may be 8 to 50 amino acid residues, may be 9 to 30 amino acid residues, may be 10 to 20 amino acid residues, and may be 11 to 15 amino acid residues. Peptide synthesis is easier in a case where the total length is shorter.

In the present disclosure, a region between the N-terminal of the cyclic peptide according to the present disclosure and the N-terminal of the cyclic segment (in a case where a plurality of cyclic segments are contained in the cyclic peptide, the N-terminal of the cyclic segment on the most N-terminal side) may be referred to as a cyclic peptide N-terminal region or a first segment. In the present disclosure, a region between the C-terminal of the cyclic peptide according to the present disclosure and the C-terminal of the cyclic segment (in a case where a plurality of cyclic segments are contained in the cyclic peptide, the C-terminal of the cyclic segment on the most C-terminal side) may be referred to as a cyclic peptide C-terminal region or a second segment.

The presence of the N-terminal region of the cyclic peptide is optional and the N-terminal region thereof may not be present. In a case where the cyclic peptide N-terminal region is not present, the N-terminal of the cyclic segment corresponds to the N-terminal of the cyclic peptide. Similarly, the presence of the C-terminal region of the cyclic peptide is optional and the C-terminal region thereof may not be present. In a case where the cyclic peptide C-terminal region is not present, the C-terminal of the cyclic segment corresponds to the C-terminal of the cyclic peptide.

The N-terminal amino group of the cyclic peptide may be subjected to N-terminal modification such as N-acetylation, N-formylation, N-acylation, or PEGylation. In addition, the C-terminal carboxy group of the cyclic peptide may be subjected to C-terminal modification such as amidation or PEGylation.

The cyclic peptide according to the present disclosure may be a cyclic peptide represented by Formula II.

Formula II $$R^N-X_{v0}-X^6_{t0}-X_{p0}-X^a-X_m-R-G-D-X_n-X^b-X_{q0}-X^7_{u0}-X_{w0}-Rc$$

In Formula II, $X^a$ represents an amino acid residue located on the most N-terminal side of the cyclic segment, $X^b$ represents an amino acid residue located on the most C-terminal side of the cyclic segment, where a thioether bond is formed between the amino acid residue $X^a$ and the amino acid residue $X^b$, X represents any amino acid residue, where in a case where a plurality of X's are present, the plurality of X's may be the same or different from each other, $R^N$ represents an N-terminal group; $R^C$ represents a C-terminal group, $X^6$ and $X^7$ each independently represent an amino acid residue having an immobilizing functional group in a side chain, where in a case where a plurality of $X^6$'s or $X^7$'s are present, the plurality of $X^6$'s or $X^7$'s may be the same or different from each other, m and n are integers and simultaneously satisfy $0 \le m \le 9$, $0 \le n \le 9$, and $3 \le m+n \le 9$, p0 and q0 are integers and respectively satisfy $0 \le p0 \le 15$ and $0 \le q0 \le 15$, t0 and u0 are integers and respectively satisfy $0 \le t0 \le 5$ and $0 \le u0 \le 5$, v0 and w0 are integers and respectively satisfy $0 \le v0 \le 5$ and $0 \le w0 \le 5$, and further, p0, q0, t0, u0, v0, and w0 satisfy $0 \leq p0+q0+t0+u0+v0+w0 \leq 39$.

In Formula II and Formula V below, a subscript is an integer indicating how many amino acid residues represented by the symbol described just before the subscript are present. For example, p0 in the notation of $X_{p0}$ indicates that p0 pieces of amino acid residues represented by X are alignedly present. In a case where the subscript represents an integer of 2 or more, a plurality of amino acid residues represented by the symbol described just before the subscript are present; however, the plurality of amino acid residues may be the same or different from each other as long as the definition thereof is satisfied.

In the cyclic peptide represented by Formula II, $X^a$—$X_m$—R-G-D-$X_n$—$X^b$ corresponds to the cyclic segment. Preferred examples of $X^a$ and $X^b$ will be described later.

<<$X^6_{t0}$ and $X_{u0}^7$>>

In Formula II, $X^6$ and $X^7$ each independently represent an amino acid residue having an immobilizing functional group in the side chain.

In a case where a plurality of $X^6$'s or $X^7$'s are present, the plurality of $X^6$'s or $X^7$'s may be the same or different from each other.

(Immobilizing Functional Group)

The above-described "immobilizing functional group" refers to a functional group capable of forming a covalent bond by reacting with a functional group on a base material or a holding material, which will be described later.

Examples of the immobilizing functional group include an amino group, a carboxy group, a hydroxy group, a thiol group, an aldehyde group (a formyl group), a carbamoyl group, an azide group, and an alkynyl group.

Examples of the combination of the immobilizing functional group contained in the cyclic peptide according to the present disclosure and the functional group on the base material or the holding material include a combination of an amino group and a carboxy group, a combination of an amino group and an aldehyde group, a combination of an amino group and an epoxy group, a combination of a hydroxy group and an epoxy group, a combination of a carboxy group and a hydroxy group, a combination of a thiol group and an epoxy group, and a combination of an azide group and an alkynyl group.

The immobilizing functional group contained in the cyclic peptide according to the present disclosure reacts with a functional group on the base material or the holding material to form a covalent bond, whereby the cyclic peptide according to the present disclosure is immobilized on the base material or the holding material. Here, it is sufficient that at least a part of the immobilizing functional groups contained in the cyclic peptide according to the present disclosure reacts with the functional group on the base material or the holding material to form a covalent bond, and all the immobilizing functional groups do not have to react with the functional groups on the base material or the holding material.

In the amino acid having an immobilizing functional group in the side chain, the immobilizing functional group is preferably at least one selected from the group consisting of an amino group, a thiol group, and an aldehyde group, and more preferably at least one selected from the group consisting of an amino group and a thiol group.

(Amino Acid Having an Immobilizing Functional Group in Side Chain)

The amino acid having an immobilizing functional group in the side chain is preferably at least one amino acid selected from the group consisting of an L-lysine, a D-lysine, an L-cysteine, a D-cysteine, an L-homocysteine, and a D-homocysteine.

In a case where an amino group is used as the immobilizing functional group, the amino group can be bonded to the carboxy group on the base material or the holding material through an amide bond, and thus the cyclic peptide according to the present disclosure can be easily immobilized on the base material or the holding material.

In addition, in a case where a thiol group is used as the immobilizing functional group, the thiol group can be bonded to the epoxy group on the base material or the holding material through a covalent bond, and thus the cyclic peptide according to the present disclosure can be easily immobilized on the base material or the holding material.

Examples of the amino acid residue having an amino group in the side chain include an L-lysine residue and a D-lysine residue, and examples of the amino acid residue having a thiol group in the side chain include an L-cysteine residue and a D-cysteine residue. Since these amino acid residues can be introduced at a relatively low cost, the production cost of the cyclic peptide according to the present disclosure can be reduced. For this reason, the use of the above amino acid residues is preferable from an economical viewpoint.

In Formula II, t0 and u0 are integers that respectively satisfy $0 \leq t0 \leq 5$ and $0 \leq u0 \leq 5$.

t0 preferably satisfies $0 \leq t0 \leq 3$ and more preferably satisfies $0 \leq t0 \leq 2$.

u0 preferably satisfies $0 \leq u0 \leq 3$, and more preferably satisfies $0 \leq u0 \leq 2$.

<<$X_{p0}$, $X_{q0}$, $X_{v0}$, and $X_{w0}$>>

X in $X_{p0}$, $X_{q0}$, $X_{v0}$, and $X_{w0}$ represents any amino acid residue, and in a case where a plurality of X's are present, the plurality of X's may be the same or different from each other.

X may be an amino acid residue and is not particularly limited; however, it is preferably an amino acid residue derived from an amino acid selected from the group consisting of the amino acids (excluding B, Z, and X) listed in Table 1 and the amino acids listed in Table 2, and it is more preferably an amino acid residue derived from an amino acid selected from the group consisting of the amino acids (excluding B, Z, and X) listed in Table 1. In addition, an amino acid residue derived from an enantiomer or a diastereomer of the above amino acid, in a case of being present, may also be used.

p0 described above and q0 described above are integers and respectively satisfy $0 \leq p0 \leq 15$ and $0 \leq q0 \leq 15$.

p0 preferably satisfies $0 \leq p0 \leq 10$, more preferably satisfies $0 \leq p0 \leq 5$, still more preferably satisfies $0 \leq p0 \leq 3$, and even still more preferably satisfies $0 \leq p0 \leq 2$.

q0 preferably satisfies $0 \leq q0 \leq 10$, more preferably satisfies $0 \leq q0 \leq 5$, still more preferably satisfies $0 \leq q0 \leq 3$, and even still more preferably $0 \leq q0 \leq 2$.

v0 described above and w0 described above are integers that respectively satisfy $0 \leq v0 \leq 5$ and $0 \leq w0 \leq 5$.

v0 preferably satisfies $0 \leq v0 \leq 3$ and more preferably satisfies $0 \leq v0 \leq 2$.

w0 preferably satisfies $0 \leq w0 \leq 3$ and more preferably satisfies $0 \leq w0 \leq 2$.

<<$X_m$ and $X_n$>>

Each X in $X_m$ and $X_n$ may be any amino acid residue and, for example, may be an isoleucine residue, a valine residue, an aspartic acid residue, a glutamic acid residue, a tyrosine residue, a leucine residue, a threonine residue, a homotyrosine residue, a proline residue, a serine residue, an asparagine residue, an alanine residue, a homoserine residue, a phenylalanine residue, an arginine residue, or a glycine residue.

m described above and n described above are integers and simultaneously satisfy $0 \leq m \leq 9$, $0 \leq n \leq 9$, and $3 \leq m+n \leq 9$.

m preferably satisfies $0 \leq m \leq 5$, more preferably satisfies $0 \leq m \leq 3$, and still more preferably satisfies $0 \leq m \leq 2$.

n preferably satisfies $1 \leq n \leq 5$ and more preferably satisfies $2 \leq n \leq 4$. n may be an integer that satisfies $2 \leq n \leq 3$.

<<$R^N$ and $R^C$>>

$R^N$ represents the N-terminal group.

Examples of the N-terminal group include an amino group, and the amino group as the N-terminal group may be subjected to N-terminal modification such as N-acetylation, N-formylation, N-acylation, or PEGylation.

$R^C$ represents the C-terminal group.

Examples of the C-terminal group include a carboxy group, and the carboxy group as the C-terminal group may be subjected to C-terminal modification such as amidation or PEGylation.

In Formula II, $R^N$ is described on the left side of $X_{v0}$. For example, in a case where all of v0, t0, and p0 are 0, $R^N$ corresponds to an amino group or modified amino group of the amino acid residue represented by $X^a$. Similarly, in Formula II, $R^C$ is described on the right side of $X_{w0}$. For example, in a case where all of q0, u0, and w0 are 0, $R^c$ corresponds to a carboxy group or modified carboxy group of the amino acid residue represented by $X^b$.

The moiety of $X^a—X_m—$R-G-D-$X_m—X^b$ in Formula II may be a moiety represented by Formula III ($X^a—X^t_{v5}—X^{11}—X^{21}—$R-G-D-$X^{31}—X^{41}—X^{51}_{v6}—X^t_{v7}—X^b$) or Formula IV ($X^a—X^t_{v5}—X^1—X^2—$R-G-D-$X^3—X^4—X^5_{v6}—X^t_{v7}—X^b$). Since the cyclic segment is a moiety represented by Formula III or Formula IV, the integrin binding property can be obtained with higher reliability. In this case, the cyclic peptide may be a cyclic peptide having a structure represented by $X^{J1}_{g1}$-(cyclic segment)-$X^{J2}_{g2}$. Here, $X^{J1}$'s each independently represent any amino acid residue, $X^{J2}$'s also each independently represent any amino acid residue, g1 represents an integer of 0 to 8, and g2 represents an integer of 0 to 8. It is preferable that $X^{J1}$'s each independently represents K, A, G, D, E, or β-alanine. It is preferable that $X^{J2}$'s each independently represents K, A, G, D, E, or β-alanine. At least one of $X^{J1}$ or $X^{J2}$ may contain $(K)_{g3}$ (g3 pieces of consecutive K residues), where g3 represents an integer of 2 to 6 and preferably represents 3 or 4. g1 and g2 each independently represents preferably an integer of 0 to 6, may represent an integer of 0 to 4, may represent an integer of 0 to 2, may represent 0 or 1, and may represent 0. $X^{J1}_{g1}$ may be, for example, KKKA, and $X^{J2}_{g2}$ may be, for example, A.

The cyclic peptide according to the present disclosure may be a cyclic peptide represented by Formula V in a case of containing two or more cyclic segment moieties.

e0 represents an integer of 0 or more. e0 may represent an integer of 0 to 20, may represent an integer of 1 to 10, and further preferably may represent an integer of 2 to 5. d0 represents an integer of 1 or more. d0 may represent an integer of 1 to 3, may represent 1 or 2, and may represent 1. $X^a$, $X_m$, $X_n$, and $X^b$ each appear a plurality of times. $X^a$'s, where $X^a$ appears a plurality of times, may be the same or different from each other, $X^b$'s, where $X^b$ appears a plurality of times, may be the same or different from each other, $X_m$'s, where $X_m$ appears a plurality of times, may be the same or different from each other, and $X_n$'s, where $X_n$ appears a plurality of times, may be the same or different from each other. Here, that $X_m$'s are the same as each other means that a row of m pieces of X and a row of m pieces X are completely the same. That $X_m$'s are different from each other means that a row of m pieces of X and a row of m pieces of X differ in at least one X. The same applies to $X_n$.

The number of cyclic segments is not particularly limited; however, as the number of cyclic segments becomes large, the integrin binding property tends to be capable of being improved. As the number of cyclic segments becomes small, the total number of amino acid residues can be reduced, whereby the antigenicity tends to be capable of being suppressed. From the viewpoint of the cost of synthesizing the cyclic peptide, it is preferable that the number of amino acid residues is small, and it is preferable that the number of cyclic segments is small.

The amino acid residue $X^a$ and the amino acid residue $X^b$ are amino acid residues that form a thioether bond between $X^a$ and $X^b$. The thioether bond is a divalent linking structure represented by $R^1—S—R^2$, where $R^1$ and $R^2$ are an organic group and both are generally a carbon atom. In a case where the amino acid residue $X^a$ and the amino acid residue $X^b$ are crosslinked by a thioether bond, a high bond stability can be obtained as compared with the case of crosslinking with a disulfide bond. In the present disclosure, the technique for forming the thioether bond is not particularly limited, however; for example, in a case where a thiol group is allowed to react with an organic group having a halogen, it is possible to form a thioether bond in which a sulfur atom of the thiol group is bonded to an organic group, with the generation of a hydrogen halide. Examples of the organic group having a halogen include a haloacetyl group. The halogen atom of the haloacetyl group may be any one of a fluorine atom, a chlorine atom, a bromine atom, an iodine atom, and the like. Among these, a bromine atom or a chlorine atom is preferable, and a chlorine atom is more preferable, from the viewpoint of the reactivity, the ease of formation of a thioether bond, and safety.

In a case where the amino acid residue $X^a$ is an amino acid residue derived from an a amino acid, it is preferable that the thioether bond is present on the side chain of an amino acid residue derived from the α amino acid but not on an amino group or modified amino group bonded to the α carbon of the α amino acid. Similarly, regarding the amino acid residue $X^b$ as well, in a case where the amino acid residue $X^b$ is an amino acid residue derived from an α amino acid, it is preferable that the thioether bond is present on the side chain of an amino acid residue derived from the α amino acid but not on a carboxy group or modified carboxy group bonded to the α carbon of the α amino acid.

Formula V $$R^N-X_{v0}-X^6_{t0}-X_{p0}-X^a-X_m-R-G-D-X_n-X^b-(X_{e0}-X^a-X_m-R-G-D-X_n-X^b)_{d0}-X_{q0}-X^7_{u0}\cdot X_{w0}-Rc$$

In Formula V, $R^N$, X, v0, $X^6$, t0, p0, $X^a$, m, n, $X^b$, q0, $X^7$, u0, w0, and $R^c$ are each synonymous with $R^N$, X, v0, $X^6$, t0, p0, $X^a$, m, n, $X^b$, q0, $X^7$, u0, w0, and $R^c$ in Formula (II), and the preferred examples thereof and ranges thereof are the same as those in Formula II.

In order to form a thioether bond on the side chain of the amino acid residue as described above, it is preferable that one of the amino acid residue $X^a$ and the amino acid residue $X^b$ before the formation of a thioether bond is an amino acid residue having a thiol group on the side chain, and the other thereof is an amino acid residue having an organic group having a halogen, on the side chain. Examples of the amino acid residue having a thiol group on the side chain include an amino acid residue represented by the following Structural Formula (t-2) or (u-2).

(t-2)

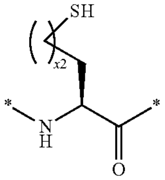

(u-2)

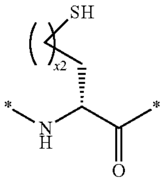

In the Structural Formulae (t-2) and (u-2), * is a bonding site to an adjacent amino acid residue, x2 is an integer of 0 or more, and x2 pieces of carbon atoms and a carbon atom at the β-position may be substituted with one or more substituents selected from the group consisting of $—NH_2$, —SH, —COOH, a $C_1$-$C_{10}$ alkyl group, and a $C_6$-$C_{14}$ aryl group. x2 may be an integer of 0 to 10, may be an integer of 0 to 6, and may be an integer of 1 to 4. Examples of the $C_1$ to $C_{10}$ alkyl group include a methyl group, an ethyl group, an n-propyl group, an i-propyl group, an n-butyl group, an i-butyl group, and a tert-butyl group. Examples of the $C_6$ to $C_{14}$ aryl group include a phenyl group, a naphthyl group, an anthranyl group, and a phenanthrene group.

More specific examples of the amino acid residue having a thiol group on the side chain include a cysteine residue, a penicillamine residue, a homocysteine residue (a residue derived from 2-amino-4-mercaptobutanoic acid), and a residue derived from 2-amino-5-mercaptopentanoic acid.

Examples of the amino acid residue having an organic group having a halogen, on the side chain, include an amino acid residue represented by the following Structural Formula (p-2) or (q-2).

(p-2)

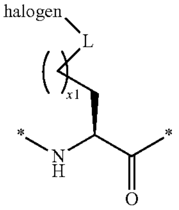

-continued (q-2)

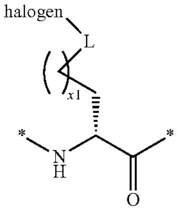

In the Structural Formulae (p-2) and (q-2), * is a bonding site to an adjacent amino acid residue, the halogen is any halogen atom, for example, F, Cl, Br, or I, x1 is an integer of 0 or more, x1 pieces of carbon atoms and a carbon atom at a β-position may be substituted with one or more substituents selected from the group consisting of $—NH_2$, —SH, —COOH, a $C_1$-$C_{10}$ alkyl group, and a $C_6$-$C_{14}$ aryl group, and the halogen-L is halogen atom-$(CH_2)_{y1}$—C(═O)— or halogen atom-$(CH_2)_{y1}$—C(═O)—NH—, where y1 represents an integer of 0 or more and 10 or less. x1 may be an integer of 0 to 10, may be an integer of 1 to 6, and may be an integer of 2 to 4. y1 may be an integer of 0 to 10, may be an integer of 1 to 6, and may be an integer of 1 to 3. Examples of the $C_1$ to $C_{10}$ alkyl group include a methyl group, an ethyl group, an n-propyl group, an i-propyl group, an n-butyl group, an i-butyl group, and a tert-butyl group. Examples of the $C_6$ to $C_{14}$ aryl group include a phenyl group, a naphthyl group, an anthranyl group, and a phenanthrene group.

More specific examples of the amino acid residue having an organic group having a halogen atom, on the side chain, include, which are not limited thereto, amino acid residues derived from 2-amino-3-[(2-haloacetyl)amino]propanoic acid, 2-amino-4-[(2)-haloacetyl)amino]butanoic acid, N-ε-haloacetylornithine, N-ε-haloacetyllysine, and N-ζ-haloacetylhomolysine. Examples of the halogen atom in these amino acid residues include a fluorine atom, a chlorine atom, a bromine atom, and an iodine atom. Among them, a chlorine atom or a bromine atom is preferable, and a chlorine atom is more preferable.

In an exemplary embodiment, the amino acid residue that does not supply the sulfur atom of the thioether bond, among the amino acid residue $X^a$ and the amino acid residue $X^b$ after the formation of a thioether bond, is an amino acid residue represented by the following (p) or (g).

(p)

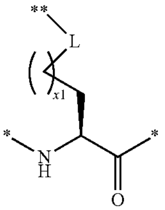

(q)

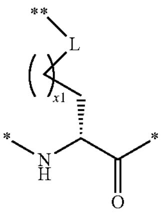

Here, in the formulae (p) and (q), * is a bonding site to an adjacent amino acid residue, ** is a bonding site to a sulfur atom of an amino acid residue which is a counterpart in the thioether bond, x1 is an integer of 0 or more, x1 pieces of carbon atoms and a carbon atom at a β-position may be substituted with one or more substituents selected from the group consisting of —$NH_2$, —SH, —COOH, a $C_1$-$C_{10}$ alkyl group, and a $C_6$-$C_{14}$ aryl group,

-L is —$(CH_2)_{y1}$—C(═O)— or **—$(CH_2)_{y1}$—C(═O)—NH—, where y1 represents an integer of 0 or more and 10 or less, and x1 may be an integer of 0 to 10, may be an integer of 1 to 6, and may be an integer of 2 to 4. y1 may be an integer of 0 to 10, may be an integer of 1 to 6, and may be an integer of 1 to 3.

Examples of the $C_1$ to $C_{10}$ alkyl group include a methyl group, an ethyl group, an n-propyl group, an i-propyl group, an n-butyl group, an i-butyl group, and a tert-butyl group. Examples of the $C_6$ to $C_{14}$ aryl group include a phenyl group, a naphthyl group, an anthranyl group, and a phenanthrene group.

More specific examples of the amino acid residue that does not supply the sulfur atom of the thioether bond include an amino acid residue in which one of hydrogen atoms of the $CH_3$ moiety of the acetyl group of the amino acid residue derived from 2-amino-3-[acetylamino]propanoic acid, 2-amino-4-[acetylamino]butanoic acid, N-δ-acetylornithine, N-ε-acetyllysine, N-ζ-acetylhomolysine, and the like is substituted with a bond to an amino acid residue which is a counterpart in the thioether bond.

In an exemplary embodiment, the amino acid residue that supplies the sulfur atom of the thioether bond, among the amino acid residue $X^a$ and the amino acid residue $X^b$ after the formation of a thioether bond, is an amino acid residue represented by the following (t) or (u).

(t)

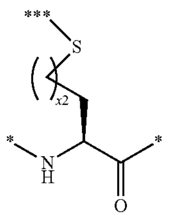

(u)

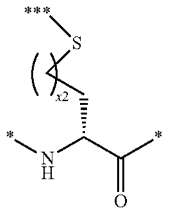

Here, in the formulae (t) and (u), * is a bonding site to an adjacent amino acid residue, *** is a bonding site to a carbon atom of an amino acid residue which is a counterpart in the thioether bond, x2 is an integer of 0 or more, and x2 pieces of carbon atoms and a carbon atom at a β-position may be substituted with one or more substituents selected from the group consisting of —$NH_2$, —SH, —COOH, a $C_1$-$C_{10}$ alkyl group, and a $C_6$-$C_{14}$ aryl group.

However, in a case where one of the amino acid residue $X^a$ and the amino acid residue $X^b$ is an amino acid residue of the (p) or the (q), in which x1 is 0, the other of the amino acid residue $X^a$ and the amino acid residue $X^b$ is not an L-cysteine residue or a D-cysteine residue. x2 may be an integer of 0 to 10, may be an integer of 0 to 6, and may be an integer of 1 to 4.

Examples of the $C_1$ to $C_{10}$ alkyl group include a methyl group, an ethyl group, an n-propyl group, an i-propyl group, an n-butyl group, an i-butyl group, and a tert-butyl group. Examples of the $C_6$ to $C_{14}$ aryl group include a phenyl group, a naphthyl group, an anthranyl group, and a phenanthrene group.

More specific examples of the amino acid residue that supplies the sulfur atom of the thioether bond include amino acid residue in which a hydrogen atom of the thiol group in the cysteine residue, the penicillamine residue, the homocysteine residue (the residue derived from 2-amino-4-mercaptobutanoic acid), or the residue derived from 2-amino-5-mercaptopentanoic acid is substituted with a bond to an amino acid residue which is a counterpart in the thioether bond.

Preferably, one of the amino acid residue $X^a$ and the amino acid residue $X^b$ is an amino acid residue of (p) or (q), and the other of the amino acid residue $X^a$ and the amino acid residue $X^b$ is a residue of (t) or (u). However, in a case where one of the amino acid residue $X^a$ and the amino acid residue $X^b$ is an amino acid residue of the (p) or the (q), in which x1 is 0, the other of the amino acid residue $X^a$ and the amino acid residue $X^b$ is not an L-cysteine residue or a D-cysteine residue.

The amino acid residue that does not supply the sulfur atom of the thioether bond, such as the amino acid residue of (p) or (q), may be present at the N-terminal of the cyclic segment, that is, may be the amino acid residue $X^a$ or may be present at the C terminal of the cyclic segment, that is, may be the amino acid residue $X^b$. Correspondingly to the above, the amino acid residue that supplies the sulfur atom of the thioether bond, such as the amino acid residue of (t) or (u), may be present at the C-terminal of the cyclic segment, that is, may be the amino acid residue $X^b$ or may be present at the N terminal of the cyclic segment, that is, may be the amino acid residue $X^a$.

The amino acid residue of the (p) or the (q) may be a residue selected from the following (a) to (h).

(a)

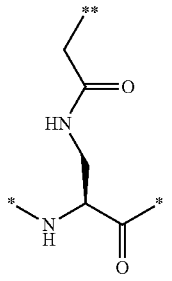

(b)

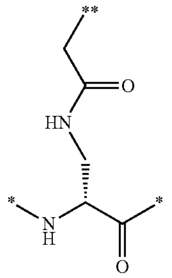

-continued (c)

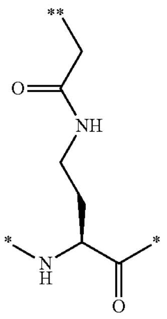

(d)

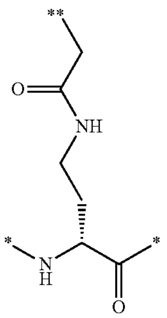

(e)

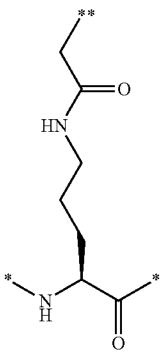

(f)

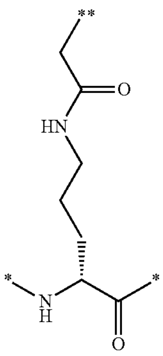

-continued (g)

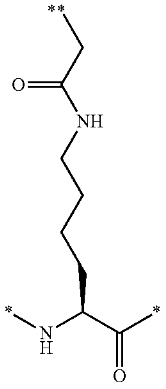

(h)

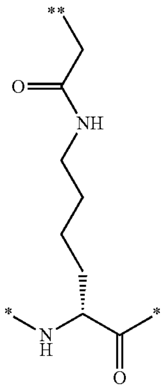

Here, in the formulae, * is a bonding site to an adjacent amino acid residue, and ** is a bonding site to a sulfur atom of an amino acid residue which is a counterpart in the thioether bond.

The amino acid residue of the (t) or the (u) may be selected from the group consisting of an L-homocysteine residue, a D-homocysteine residue, an L-penicillamine residue, a D-penicillamine residue, an L-cysteine residue, and a D-cysteine residue.

In the present disclosure, it was found that even in a case where amino acid residues are crosslinked with each other by a thioether bond that provides a high bond stability than a disulfide bond to prepare an integrin-binding cyclic peptide, the molecule stability of the cyclic peptide varies depending on the structure around the thioether bond. In the present disclosure, it was found that in a case where one of the amino acid residue $X^a$ and the amino acid residue $X^b$ is a cysteine residue, further improved molecule stability is obtained by designing the α carbon of the other amino acid residue of the amino acid residue $X^a$ and the amino acid residue $X^b$ to be separated from the sulfur atom of the cysteine residue by five or more atoms. Although it is not clear why further improved molecule stability can be obtained, it is presumed that the electron arrangement in the thioether bond is stabilized by increasing the carbon chain length from the crosslinking moiety to the cyclic peptide main chain, and thus a high bond stability is obtained.

Accordingly, for example, a combination of the amino acid residue of the (a) or the (b) and the L-cysteine residue or the D-cysteine residue is excluded from the possible combinations of the amino acid residue $X^a$ and the amino acid residue $X^b$.

A case where the amino acid residue of the (a) is bonded to the L-cysteine residue is shown below.

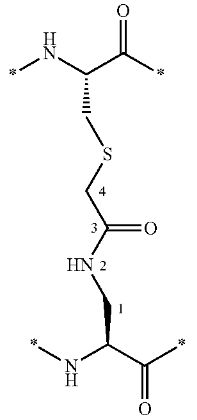 [SMILES: *N[C@@H](CNC(=O)CSC[C@H](N*)C(*)=O)C(*)=O]

Here, in the formula, * is a bonding site to an adjacent amino acid residue. In a case where the amino acid residue of (a) is bonded to the L-cysteine residue, the α carbon and the sulfur atom of the cysteine residue are separated by four atoms, that is, by one nitrogen atom and three carbon atoms. As described above, the number of atoms separating the α carbon of the amino acid residue which is a counterpart in the thioether bond from the sulfur atom of the cysteine residue means the number of atoms on a chain connecting the α atom and the sulfur atom, and atoms that do not participate in the chain, such as hydrogen atoms bonded to the atom on the chain are not counted.

Among the amino acid residue $X^a$ and the amino acid residue $X^b$, the amino acid residue that supplies the sulfur atom of the thioether bond may be an amino acid residue in which the number (the total number of carbon atoms, including a branch moiety in a case where the branch is present) of carbon atoms on the side chain having the sulfur atom is 1 to 10. However, among the amino acid residue $X^a$ and the amino acid residue $X^b$, the amino acid residue that supplies the sulfur atom of the thioether bond is preferably an amino acid residue in which the number (the total number of carbon atoms, including a branch moiety in a case where the branch is present) of carbon atoms on the side chain having the sulfur atom is 2 to 10, from the viewpoint of obtaining a higher molecule stability. In the amino acid residue that supplies the sulfur atom of the thioether bond, the number of carbon atoms on the side chain may be 2 to 6 or may be 2 or 3. From this viewpoint, the amino acid residue that supplies the sulfur atom of the thioether bond may be, for example, penicillamine (the number of carbon atoms on the side chain is 3), homocysteine (the number of carbon atoms on the side chain is 2), or the like. Here, the cysteine residue has one carbon atom on the side chain. The counting of carbon atoms on the side chain for penicillamine is described below. In the following structural formula, * represents a bonding site to an adjacent amino acid residue.

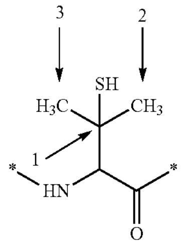 [SMILES: *NC(C(*)=O)C(C)(C)S]

Among the amino acid residue $X^a$ and the amino acid residue $X^b$, the amino acid residue that supplies the sulfur atom of the thioether bond may be an amino acid residue in which the main chain and the sulfur atom on the side chain are separated by 1 to 10 carbon atoms. However, among the amino acid residue $X^a$ and the amino acid residue $X^b$, the amino acid residue that supplies the sulfur atom of the thioether bond is preferably an amino acid residue in which the main chain and the sulfur atom on the side chain are separated by 2 to 10 carbon atoms from the viewpoint of obtaining more stable integrin binding property. That is, in the case of an amino acid residue derived from an α amino acid, it is preferable that the α carbon and the sulfur atom are separated by 2 to 10 carbon atoms. The main chain and the sulfur atom on the side chain may be separated by 2 to 6 carbon atoms or may be separated by 2 to 4 carbon atoms. Here, "may be an amino acid residue in which the main chain and the sulfur atom on the side chain are separated by X pieces of atoms" means that the amino acid residue is an amino acid residue in which a chain consisting of X pieces of carbon atoms connects between a carbon atom on the main chain of the cyclic peptide, where the carbon atom is the starting point of the side chain, and the sulfur atom on the side chain, and the number of carbon atoms in the branch moiety branched from the chain is not counted. In addition, in a case where a plurality of routes connecting the carbon atom, which is the starting point of the side chain, on the main chain of the cyclic peptide and the sulfur atom on the side chain are present due to the presence of the ring structure or the like, the carbon atoms on the shortest chain are counted.

For example, in the penicillamine residue, the α carbon and the sulfur atom are separated by one carbon atom. This is because, in the penicillamine residue, the carbon atoms in the two methyl groups, which are not contained in the chain connecting the α carbon and the sulfur atom, are not counted although the α carbon and the sulfur atom are connected by $-C(CH_3)_2-$ as shown in the following structural formula. Similarly, in the cysteine residue, the α carbon and the sulfur atom are separated by one carbon atom. In the homocysteine residue, the α carbon and the sulfur atom are separated by two carbon atoms.

Cysteine and penicillamine have a stronger racemization tendency than other sulfur atom-containing amino acids such as homocysteine. As a result, it is advantageous to use an amino acid such as a homocysteine residue, which satisfies the above-described regulation on the number of carbon atoms, in terms of controlling the three-dimensional structure as compared with the case of using cysteine, penicillamine, or the like, and the integrin binding property per unit amount tends to be capable of being improved since the proportion of stereoisomers having a low integrin binding property or having no integrin binding property can be reduced.

In the following structural formula, * represents a bonding site to an adjacent amino acid residue.

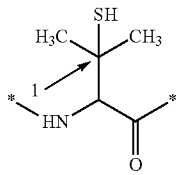 [SMILES: *NC(C(*)=O)C(C)(C)S]

From the viewpoint of obtaining a higher molecule stability, it is preferable that even in a case where the amino acid residue that supplies the sulfur atom of the thioether bond is not a cysteine residue, the α carbon of an amino acid residue that does not supply the sulfur atom of the thioether bond and the sulfur atom of an amino acid residue that supplies the sulfur atom of the thioether bond, among the amino acid residue $X^a$ and the amino acid residue $X^b$, are separated by five or more atoms. For example, regardless of the fact that the amino acid residue that supplies the sulfur atom of the thioether bond is a cysteine residue or not, the α carbon of the amino acid residue that does not supply the sulfur atom of the thioether bond and the sulfur atom of the amino acid residue that supplies the sulfur atom of the thioether bond may be separated by 5 to 9 atoms, and may be separated by 5 to 7 atoms.

In a case of forming a thioether bond by reacting a thiol group with an organic group having a halogen between an amino acid residue having the thiol group on the side chain and an amino acid residue having the organic group having a halogen, on the side chain, it is possible to form the thioether bond by reacting a linear peptide before cyclization in a neutral or basic buffer solution. For example, an aqueous solution containing a linear peptide may be slowly added dropwise to a Tris-HCl (pH 8.5) buffer solution and allowed to stand. Since the thioether bond formation reaction is highly reactive, the reaction proceeds rapidly under room temperature conditions without any particular heating. In the cyclization reaction, in addition to the cyclic peptide, an oligomer in which a plurality of noncyclic peptides are connected by intermolecular bonding may be formed depending on the reaction conditions. For this reason, in order to obtain only the cyclic peptide, it is preferable to purify the peptide after the cyclization reaction by reverse phase high performance liquid chromatography or the like.

The cyclic peptide according to the present disclosure contains at least one of the N-terminal region (the first segment) of the cyclic peptide or the C-terminal region (the second segment) of the cyclic peptide, where at least one of the first segment or the second segment may have a structure containing an amino acid residue having an immobilizing functional group in the side chain. The immobilizing functional group may be an amino group or a thiol group. The amino acid residue having an immobilizing functional group in the side chain may be an amino acid residue selected from the group consisting of an L-lysine residue, a D-lysine residue, an L-cysteine residue, a D-cysteine residue, an L-homocysteine residue, and a D-homocysteine residue. For details of the amino acid residue having an immobilizing functional group in the side chain, the description of the amino acid residue represented by $X^6$ or $X^7$ in Formula II can be referenced.

In the present disclosure, at least one of the N-terminal region of the cyclic peptide or the C-terminal region of the cyclic peptide may contain a lysine residue as the amino acid residue having an immobilizing functional group in the side chain. More specifically, at least one of the N-terminal region of the cyclic peptide or the C-terminal region of the cyclic peptide may contain one lysine residue, and alternatively, may consecutively contain two or more lysine residues, may consecutively contain 2 to 10 lysine residues, and may consecutively contain 2 to 5 lysine residues, as the amino acid residue having an immobilizing functional group in the side chain.

The amino acid residue having the above-described immobilizing functional group is preferably present at at least one of the N-terminal of the first segment or the C-terminal of the second segment of the cyclic peptide according to the present disclosure. For example, amino acid residues having an immobilizing functional group may be consecutively present at at least one of the N-terminal of the first segment or the C-terminal of the second segment of the cyclic peptide according to the present disclosure, and the number of consecutive amino acid residues having an immobilizing functional group may be, for example, 2 to 10 residues or may be 2 to 5 residues. More specifically, lysine residues may be consecutively present at at least one of the N-terminal of the first segment or the C-terminal of the second segment of the cyclic peptide according to the present disclosure, and the number of consecutive lysine residues may be, for example, 2 to 10 residues or may be 2 to 5 residues. In this case, the first segment or the second segment may be composed of only consecutive lysine residues; however, other amino acid residues may be optionally contained. For example, in the first segment or the second segment, the other amino acid residues may not present in a region between the consecutive lysine residues and the cyclic segment, and alternatively, the region between the consecutive lysine residues and the cyclic segment may be composed of amino acid residues of 1 to 20 residues, 1 to 10 residues, 1 to 5 residues, or 1 to 3 residues, selected from an alanine residue, a β-alanine residue, a glutamic acid residue, an aspartic acid residue, and a glycine residue. Alternatively, an additional lysine residue may reside between the amino acid residue selected from an alanine residue, a β-alanine residue, a glutamic acid residue, an aspartic acid residue, and a glycine residue, and the cyclic segment.

The first segment may be composed of any amino acid residues of 1 to 20 residues, 1 to 10 residues, 1 to 5 residues, or 1 to 3 residues. The first segment may contain or may not contain a lysine residue. In a case where a lysine residue is not contained, it may be composed of at least one kind of amino acid residue, having 1 to 20 residues, 1 to 10 residues, 1 to 5 residues, or 1 to 3 residues, selected from an alanine residue, a β-alanine residue, a glutamic acid residue, an aspartic acid residue, or a glycine residue. Similarly, the second segment may be composed of any amino acid residues of 1 to 20 residues, 1 to 10 residues, 1 to 5 residues, or 1 to 3 residues. The second segment may contain or may not contain a lysine residue. In a case where a lysine residue is not contained, it may be composed of at least one kind of amino acid residue, having 1 to 20 residues, 1 to 10 residues, 1 to 5 residues, or 1 to 3 residues, selected from an alanine residue, a β-alanine residue, a glutamic acid residue, an aspartic acid residue, or a glycine residue.

In the cyclic peptide according to the present disclosure, the dissociation constant (the dissociation constant regarding the binding to integrin) measured by the method described in "(2) Immobilization of cyclic peptide" and "(3) Evaluation of integrin binding property" in Examples is preferably 200 nM or less, more preferably 100 nM or less, and still more preferably 50 nM or less. The closer to 0 nM the dissociation constant is, the more preferable it is; however, from the practical viewpoint, examples of the lower limit value that can be combined with the above upper limit value include 0.1 nM or 0.5 nM. In addition, the cyclic peptide according to the present disclosure preferably has a residual rate of 30% or more, more preferably 50% or more, and still more preferably 70% or more, where the residual rate is measured by the method described in "(4) Evaluation of molecule stability" in Examples. The closer to 100% the residual rate is, the more preferable it is. For this reason, examples of the upper limit value that can be combined with the above lower limit value include 100%.

The integrin in the present disclosure is not particularly limited as long as it is an integrin that recognizes the RGD sequence. In Examples, the integrin binding property is evaluated using integrin αvβ5; however, the integrin is not limited to this, and the cyclic peptide according to the present disclosure can also bind to an integrin that recognizes an RGD sequence, such as integrin αVβ3.

In addition, in the present disclosure, the molecule stability of the cyclic peptide is measured by using the alkali resistance as an indicator; however, the molecule stability of the cyclic peptide is exhibited similarly for the resistance to stimuli other than alkali, such as X ray resistance, γ ray resistance, ultraviolet ray resistance, heat resistance, and chemical resistance. This is because the molecule stability basically represents that a molecule is more stable in terms of free energy. For example, due to having excellent alkali resistance, in a case where the cyclic peptide according to the present disclosure is used as an affinity ligand in a carrier for affinity chromatography and the carrier is used for cell purification, the integrin binding property is maintained even in a case of being repeatedly washed with alkali, and thus the cell separation cost can be reduced.

Examples of the cyclic peptide according to the present disclosure are shown in Table 3 to Table 7 below. In all cyclic peptides 1 to 165 shown in Table 3 to Table 7, all amino acid residues are amino acid residues that do not have an optical isomer, such as an L-amino acid residue and glycine. In the tables, Hcy represents a homocysteine residue, and Pen represents a penicillamine residue. Dab(acetyl) represents a 2-amino-4-acetylamino-butanoic acid residue, Dap(acetyl) represents a 2-amino-3-acetylamino-propanoic acid residue, Orn(acetyl) represents an N-δ-acetyl-ornithine residue, and Lys(acetyl) represents an N-ε-acetyl-lysine residue. One of hydrogen atoms on the methyl group in the acetyl group in the amino acid residue containing the above acetyl group is substituted with a bond to the sulfur atom in the amino acid residue, which is a bonding partner in the thioether bond, whereby intramolecular crosslinking by the thioether bond is formed. In addition, in the column of "Crosslinking moiety amino acid residue", the acetyl group is omitted. Although not shown in the table, the cyclic peptide 49 to the cyclic peptide 53 have a C-terminal having an amidated structure in which the C-terminal carboxylic acid is amide-bonded to $NH_2$. Further, βA in the cyclic peptide 51 represents a β-alanine residue, HmY in the cyclic peptide 68 represents a homotyrosine residue, and HmS in the cyclic peptide 73 represents a homoserine residue. In Table 3 to Table 7, the amino acid residues shown in parentheses indicate amino acid residues involved in the intramolecular crosslinking by the thioether bond.

TABLE 3

| Number | Amino acid sequence (N terminal -> C terminal) | Crosslinking moiety amino acid residue $X^a$ | $X^b$ | SEQ ID NO. |
|---|---|---|---|---|
| 1 | KKKG-(Hcy)-IPRGDNFR(Dab(acetyl))A | Hcy | Dab | 2 |
| 2 | KKKA-(Hcy)-IPRGDNFR(Dab(acetyl))A | Hcy | Dab | 3 |
| 3 | KKK-(Hcy)-IPRGDNFR(Dab(acetyl))A | Hcy | Dab | 4 |
| 4 | KKK-(Hcy)-IPRGDNFR(Dab(acetyl))G | Hcy | Dab | 5 |
| 5 | KKK-(Hcy)-IPRGDNFR(Dab(acetyl))D | Hcy | Dab | 6 |
| 6 | KKKG-(Hcy)-IPRGDNF(Dab(acetyl))A | Hcy | Dab | 7 |
| 7 | KKKG-(Hcy)-IPRGDNFR(Dab(acetyl)) | Hcy | Dab | 8 |
| 8 | KKKG-(Hcy)-PRGDNFR(Dab(acetyl))A | Hcy | Dab | 9 |
| 9 | KKK-(Hcy)-PRGDNFR(Dab(acetyl))A | Hcy | Dab | 10 |
| 10 | KKK-(Hcy)-IPRGDNF(Dab(acetyl))A | Hcy | Dab | 11 |
| 11 | KKK-(Hcy)-IPRGDNFR(Dab(acetyl)) | Hcy | Dab | 12 |
| 12 | KKK(Dap(acetyl))IPRGDNFR-(Hcy) | Dap | Hcy | 13 |
| 13 | KKK-(Hcy)-IPRGDNF(Dab(acetyl)) | Hcy | Dab | 14 |
| 14 | KKK-(Hcy)-VPRGDNF(Dab(acetyl)) | Hcy | Dab | 15 |
| 15 | KKK-(Hcy)-AIPRGDNFR(Dab(acetyl))A | Hcy | Dab | 16 |
| 16 | KKK-(Hcy)-IPRGDNFRA(Dab(acetyl))A | Hcy | Dab | 17 |
| 17 | KKK-(Hcy)-AIPRGDNFRA(Dab(acetyl))A | Hcy | Dab | 18 |
| 18 | KKK-(Hcy)-AAIPRGDNFR(Dab(acetyl))A | Hcy | Dab | 19 |
| 19 | KKK-(Hcy)-IPRGDNFRAA(Dab(acetyl))A | Hcy | Dab | 20 |
| 20 | KKKG-(Hcy)-AIPRGDNFRA(Dab(acetyl))A | Hcy | Dab | 21 |
| 21 | KKK-(Hcy)-VPRGDNFR(Dab(acetyl))A | Hcy | Dab | 22 |
| 22 | KKK-(Hcy)-DPRGDNFR(Dab(acetyl))A | Hcy | Dab | 23 |

TABLE 3-continued

| Number | Amino acid sequence (N terminal -> C terminal) | Crosslinking moiety amino acid residue $X^a$ | $X^b$ | SEQ ID NO. |
|---|---|---|---|---|
| 23 | KKK-(Hcy)-EPRGDNFR(Dab(acetyl))A | Hcy | Dab | 24 |
| 24 | KKK-(Hcy)-YPRGDNFR(Dab(acetyl))A | Hcy | Dab | 25 |
| 25 | KKK-(Hcy)-IPRGDSFR(Dab(acetyl))A | Hcy | Dab | 26 |
| 26 | KKK-(Hcy)-IPRGDNYR(Dab(acetyl))A | Hcy | Dab | 27 |
| 27 | KKKG-(Hcy)-LPRGDNFR(Dab(acetyl))A | Hcy | Dab | 28 |
| 28 | KKKG-(Hcy)-LPRGDSFR(Dab(acetyl))A | Hcy | Dab | 29 |
| 29 | KKKA-(Hcy)-VPRGDNYR(Dab(acetyl))D | Hcy | Dab | 30 |
| 30 | KKKA-(Hcy)-IPRGDNYR(Dab(acetyl))D | Hcy | Dab | 31 |
| 31 | KKKA-(Hcy)-LPRGDNYR(Dab(acetyl))D | Hcy | Dab | 32 |
| 32 | KKKA-(Hcy)-YPRGDNYR(Dab(acetyl))D | Hcy | Dab | 33 |
| 33 | KKKA-(Hcy)-EPRGDSYR(Dab(acetyl))D | Hcy | Dab | 34 |
| 34 | KKKA-(Hcy)-EPRGDNFR(Dab(acetyl))D | Hcy | Dab | 35 |
| 35 | KKKA-(Hcy)-EPRGDNYD(Dab(acetyl))D | Hcy | Dab | 36 |
| 36 | KKKA-(Hcy)-EPRGDNYE(Dab(acetyl))D | Hcy | Dab | 37 |
| 37 | KKKG-(Hcy)-EPRGDNYR(Dab(acetyl))D | Hcy | Dab | 38 |
| 38 | KKKD-(Hcy)-EPRGDNYR(Dab(acetyl))D | Hcy | Dab | 39 |
| 39 | KKKE-(Hcy)-EPRGDNYR(Dab(acetyl))D | Hcy | Dab | 40 |
| 40 | KKKA-(Hcy)-EPRGDNYR(Dab(acetyl))G | Hcy | Dab | 41 |

TABLE 4

| Number | Amino acid sequence (N terminal -> C terminal) | Crosslinking moiety amino acid residue $X^a$ | $X^b$ | SEQ ID NO. |
|---|---|---|---|---|
| 41 | KKKA-(Hcy)-EPRGDNYR(Dab(acetyl))A | Hcy | Dab | 42 |
| 42 | KKKA-(Hcy)-EPRGDNYR(Dab(acetyl))D | Hcy | Dab | 43 |
| 43 | KKKA-(Hcy)-EPRGDNYR(Dab(acetyl))E | Hcy | Dab | 44 |
| 44 | KKK-(Hcy)-EPRGDNYR(Dab(acetyl)) | Hcy | Dab | 45 |
| 45 | KKKA-(Hcy)-EPRGDNYR(Dab(acetyl)) | Hcy | Dab | 46 |
| 46 | KKK(Dap(acetyl))EPRGDNYR-(Hcy) | Dap | Hcy | 47 |
| 47 | KKKA(Dap(acetyl))EPRGDNYR-(Hcy) | Dap | Hcy | 48 |
| 48 | KKKA(Dap(acetyl))EPRGDNYR-(Hcy)-D | Dap | Hcy | 49 |
| 49 | KKK-(Hcy)-EPRGDNYR(Dab(acetyl)) | Hcy | Dab | 50 |
| 50 | KKKA-(Hcy)-EPRGDNYR(Dab(acetyl)) | Hcy | Dab | 51 |
| 51 | KKKβA-(Hcy)-EPRGDNYR(Dab(acetyl)) | Hcy | Dab | 52 |
| 52 | KKK(Dap(acetyl))EPRGDNYR-(Hcy) | Dap | Hcy | 53 |
| 53 | KKKA(Dap(acetyl))EPRGDNYR-(Hcy) | Dap | Hcy | 54 |
| 54 | KKKG-(Hcy)-IPRGDTFR(Dab(acetyl))A | Hcy | Dab | 55 |

TABLE 4-continued

| Number | Amino acid sequence (N terminal -> C terminal) | Crosslinking moiety amino acid residue $X^a$ | $X^b$ | SEQ ID NO. |
|---|---|---|---|---|
| 55 | KKKG-(Hcy)-IPRGDTFR(Dab(acetyl))G | Hcy | Dab | 56 |
| 56 | KKKA-(Hcy)-IPRGDTFR(Dab(acetyl))A | Hcy | Dab | 57 |
| 57 | KKK-(Hcy)-IPRGDTFR(Dab(acetyl))A | Hcy | Dab | 58 |
| 58 | KKKG-(Hcy)-IPRGDTF(Dab(acetyl))A | Hcy | Dab | 59 |
| 59 | KKKG-(Hcy)-IPRGDTFR(Dab(acetyl)) | Hcy | Dab | 60 |
| 60 | KKK-(Hcy)-IPRGDTF(Dab(acetyl))A | Hcy | Dab | 61 |

TABLE 5

| Number | Amino acid sequence (N terminal -> C terminal) | Crosslinking moiety amino acid residue $X^a$ | $X^b$ | SEQ ID NO. |
|---|---|---|---|---|
| 61 | KKK-(Hcy)-IPRGDTFR(Dab(acetyl)) | Hcy | Dab | 62 |
| 62 | KKK-(Hcy)-IPRGDTFA(Dab(acetyl)) | Hcy | Dab | 63 |
| 63 | KKK-(Hcy)-IPRGDTF(Dab(acetyl)) | Hcy | Dab | 64 |
| 64 | KKK-(Hcy)-VPRGDTF(Dab(acetyl)) | Hcy | Dab | 65 |
| 65 | KKK-(Hcy)-IPRGDVF(Dab(acetyl)) | Hcy | Dab | 66 |
| 66 | KKK-(Hcy)-VPRGDVF(Dab(acetyl)) | Hcy | Dab | 67 |
| 67 | KKKG-(Hcy)-AIPRGDTFRA(Dab(acetyl))A | Hcy | Dab | 68 |
| 68 | KKKG-(Hcy)-(HmY)-PRGDTFR(Dab(acetyl))A | Hcy | Dab | 69 |
| 69 | KKKG-(Hcy)-EPRGDTFR(Dab(acetyl))A | Hcy | Dab | 70 |
| 70 | KKKG-(Hcy)-VPRGDTFR(Dab(acetyl))A | Hcy | Dab | 71 |
| 71 | KKKG-(Hcy)-LPRGDTFR(Dab(acetyl))A | Hcy | Dab | 72 |
| 72 | KKKG-(Hcy)-IPRGDSFR(Dab(acetyl))A | Hcy | Dab | 73 |
| 73 | KKKG-(Hcy)-IPRGD-(HmS)-FR(Dab(acetyl))A | Hcy | Dab | 74 |
| 74 | KKKA-(Hcy)-VPRGDTFR(Dab(acetyl))A | Hcy | Dab | 75 |
| 75 | KKKA-(Hcy)-TPRGDTFR(Dab(acetyl))A | Hcy | Dab | 76 |
| 76 | KKKA-(Hcy)-ITRGDTFR(Dab(acetyl))A | Hcy | Dab | 77 |
| 77 | KKKA-(Hcy)-ISRGDTFR(Dab(acetyl))A | Hcy | Dab | 78 |
| 78 | KKKA-(Hcy)-IPRGDVFR(Dab(acetyl))A | Hcy | Dab | 79 |
| 79 | KKKA-(Hcy)-IPRGDAFR(Dab(acetyl))A | Hcy | Dab | 80 |
| 80 | KKKA-(Hcy)-IPRGDTPR(Dab(acetyl))A | Hcy | Dab | 81 |
| 81 | KKKA-(Hcy)-IPRGDTYR(Dab(acetyl))A | Hcy | Dab | 82 |
| 82 | KKKA-(Hcy)-IPRGDTFT(Dab(acetyl))A | Hcy | Dab | 83 |
| 83 | KKKA-(Hcy)-IPRGDTFS(Dab(acetyl))A | Hcy | Dab | 84 |
| 84 | KKKG-(Hcy)-IPRGDTFA(Dab(acetyl))G | Hcy | Dab | 85 |
| 85 | KKKA-(Hcy)-IPRGDTFA(Dab(acetyl))G | Hcy | Dab | 86 |
| 86 | KKKG-(Hcy)-IPRGDTFA(Dab(acetyl))A | Hcy | Dab | 87 |

TABLE 5-continued

| Number | Amino acid sequence (N terminal -> C terminal) | Crosslinking moiety amino acid residue $X^a$ | $X^b$ | SEQ ID NO. |
|---|---|---|---|---|
| 87 | KKKA-(Hcy)-IPRGDTFA(Dab(acetyl))A | Hcy | Dab | 88 |
| 88 | KKKA-(Hcy)-IPRGDTFG(Dab(acetyl))A | Hcy | Dab | 89 |
| 89 | KKKA-(Hcy)-VTRGDTFR(Dab(acetyl))A | Hcy | Dab | 90 |
| 90 | KKKA-(Hcy)-IPRGDAFA(Dab(acetyl))A | Hcy | Dab | 91 |
| 91 | KKKA-(Hcy)-VPRGDAFA(Dab(acetyl))A | Hcy | Dab | 92 |
| 92 | KKKA-(Hcy)-IPRGDSFA(Dab(acetyl))A | Hcy | Dab | 93 |
| 93 | KKKA-(Hcy)-IPRGDSFA(Dab(acetyl))G | Hcy | Dab | 94 |
| 94 | KKKG-(Hcy)-IPRGDSFA(Dab(acetyl))A | Hcy | Dab | 95 |
| 95 | KKKG-(Hcy)-IPRGDSFA(Dab(acetyl))G | Hcy | Dab | 96 |
| 96 | KKKA-(Hcy)-VPRGDSFA(Dab(acetyl))A | Hcy | Dab | 97 |
| 97 | KKKA-(Hcy)-VPRGDSFA(Dab(acetyl))G | Hcy | Dab | 98 |
| 98 | KKKG-(Hcy)-VPRGDSFA(Dab(acetyl))A | Hcy | Dab | 99 |
| 99 | KKKG-(Hcy)-VPRGDSFA(Dab(acetyl))G | Hcy | Dab | 100 |
| 100 | A-(Hcy)-IPRGDSFA(Dab(acetyl))AKKK | Hcy | Dab | 101 |

TABLE 6

| Number | Amino acid sequence (N terminal -> C terminal) | Crosslinking moiety amino acid residue $X^a$ | $X^b$ | SEQ ID NO. |
|---|---|---|---|---|
| 101 | KKK-(Hcy)-IPRGDSFA(Dab(acetyl)) | Hcy | Dab | 102 |
| 102 | KKK-(Hcy)-VPRGDSFA(Dab(acetyl)) | Hcy | Dab | 103 |
| 103 | (Hcy)-VPRGDTFA(Dab(acetyl))KKK | Hcy | Dab | 104 |
| 104 | KKK-(Hcy)-VPRGDTFA(Dab(acetyl)) | Hcy | Dab | 105 |
| 105 | KKKG-(Hcy)-VPRGDTFA(Dab(acetyl))G | Hcy | Dab | 106 |
| 106 | KKKG-(Hcy)-VPRGDTFA(Dab(acetyl))A | Hcy | Dab | 107 |
| 107 | KKKA-(Hcy)-VPRGDTFA(Dab(acetyl))G | Hcy | Dab | 108 |
| 108 | KKKA-(Hcy)-VPRGDTFA(Dab(acetyl))A | Hcy | Dab | 109 |
| 109 | A-(Hcy)-VPRGDTFA(Dab(acetyl))AKKK | Hcy | Dab | 110 |
| 110 | KKKKA-(Hcy)-VPRGDTFA(Dab(acetyl))A | Hcy | Dab | 111 |
| 111 | KKKKKA-(Hcy)-VPRGDTFA(Dab(acetyl))A | Hcy | Dab | 112 |
| 112 | KKKKKKA-(Hcy)-VPRGDTFA(Dab(acetyl))A | Hcy | Dab | 113 |
| 113 | KKKA-(Hcy)-VTRGDVFT(Dab(acetyl))A | Hcy | Dab | 114 |
| 114 | KKKG-(Hcy)-IPRGDTFR(Dap(acetyl))A | Hcy | Dap | 115 |
| 115 | KKKG-(Hcy)-IPRGDTFR(Orn(acetyl))A | Hcy | Orn | 116 |
| 116 | KKKG-(Hcy)-IPRGDTFR(Lys(acetyl))A | Hcy | K | 117 |
| 117 | KKKG(Dap(acetyl))IPRGDTFR-(Hcy)-A | Dap | Hcy | 118 |
| 118 | KKKG(Dab(acetyl))IPRGDTFR-(Hcy)-A | Dab | Hcy | 119 |
| 119 | KKKG(Orn(acetyl))IPRGDTFR-(Hcy)-A | Orn | Hcy | 120 |

TABLE 6-continued

| Number | Amino acid sequence (N terminal -> C terminal) | Crosslinking moiety amino acid residue $X^a$ | $X^b$ | SEQ ID NO. |
|---|---|---|---|---|
| 120 | KKKG(Lys(acetyl))IPRGDTFR-(Hcy)-A | K | Hcy | 121 |
| 121 | KKKA-(Hcy)-VPRGDTFA(Lys(acetyl))A | Hcy | K | 122 |
| 122 | KKKA(Dab(acetyl))VPRGDTFA-(Hcy)-A | Dab | Hcy | 123 |
| 123 | KKKA-(Hcy)-IPRGDSFA(Lys(acetyl))A | Hcy | K | 124 |
| 124 | KKKA(Dab(acetyl))IPRGDSFA-(Hcy)-A | Dab | Hcy | 125 |
| 125 | A-(Hcy)-VPRGDTFA(Dab(acetyl))A | Hcy | Dab | 126 |
| 126 | A-(Hcy)-IPRGDSFA(Dab(acetyl))A | Hcy | Dab | 127 |
| 127 | A-(Hcy)-IPRGDSFA(Dab(acetyl))G | Hcy | Dab | 128 |
| 128 | KKKG-(Pen)-IPRGDTFR(Dap(acetyl))A | Pen | Dap | 129 |
| 129 | KKKG-(Pen)-IPRGDTFR(Dab(acetyl))A | Pen | Dab | 130 |
| 130 | KKKG-(Pen)-IPRGDTFR(Orn(acetyl))A | Pen | Orn | 131 |
| 131 | KKKG-(Pen)-IPRGDTFR(Lys(acetyl))A | Pen | K | 132 |
| 132 | KKKG(Dap(acetyl))IPRGDTFR-(Pen)-A | Dap | Pen | 133 |
| 133 | KKKG(Dab(acetyl))IPRGDTFR-(Pen)-A | Dab | Pen | 134 |
| 134 | KKKG(Orn(acetyl))IPRGDTFR-(Pen)-A | Orn | Pen | 135 |
| 135 | KKKG(Lys(acetyl))IPRGDTFR-(Pen)-A | K | Pen | 136 |
| 136 | KKKA(Dab(acetyl))VPRGDTFA-(Pen)-A | Dab | Pen | 137 |
| 137 | KKKA(Dab(acetyl))IPRGDSFA-(Pen)-A | Dab | Pen | 138 |
| 138 | KKKG(Dab(acetyl))IPRGDTFR(C)A | Dab | C | 139 |
| 139 | KKKG(Orn(acetyl))IPRGDTFR(C)A | Orn | C | 140 |
| 140 | KKKG(Lys(acetyl))IPRGDTFR(C)A | K | C | 141 |

TABLE 7

| Number | Amino acid sequence (N terminal -> C terminal) | Crosslinking moiety amino acid residue $X^a$ | $X^b$ | SEQ ID NO. |
|---|---|---|---|---|
| 141 | KKK(Dab(acetyl))VPRGDTFA(C) | Dab | C | 142 |
| 142 | KKKA(Dab(acetyl))VPRGDTFA(C)A | Dab | C | 143 |
| 143 | KKK(Dab(acetyl))VPRGDNF(C) | Dab | C | 144 |
| 144 | KKK-(Hcy)-DPRGDTFA(Dab(acetyl)) | Hcy | Dab | 145 |
| 145 | KKK-(Hcy)-EPRGDTFA(Dab(acetyl)) | Hcy | Dab | 146 |
| 146 | KKK-(Hcy)-LPRGDTFA(Dab(acetyl)) | Hcy | Dab | 147 |
| 147 | KKK-(Hcy)-TPRGDTFA(Dab(acetyl)) | Hcy | Dab | 148 |
| 148 | KKK-(Hcy)-YPRGDTFA(Dab(acetyl)) | Hcy | Dab | 149 |
| 149 | KKK-(Hcy)-VSRGDTFA(Dab(acetyl)) | Hcy | Dab | 150 |
| 150 | KKK-(Hcy)-VTRGDTFA(Dab(acetyl)) | Hcy | Dab | 151 |
| 151 | KKK-(Hcy)-VPRGDVFA(Dab(acetyl)) | Hcy | Dab | 152 |

TABLE 7-continued

| Number | Amino acid sequence (N terminal -> C terminal) | Crosslinking moiety amino acid residue X^a | X^b | SEQ ID NO. |
|---|---|---|---|---|
| 152 | KKK-(Hcy)-VPRGDTFG(Dab(acetyl)) | Hcy | Dab | 153 |
| 153 | KKK-(Hcy)-VPRGDTFS(Dab(acetyl)) | Hcy | Dab | 154 |
| 154 | KKK-(Hcy)-VPRGDTFT(Dab(acetyl)) | Hcy | Dab | 155 |
| 155 | KKK-(Hcy)-TTRGDTFA(Dab(acetyl)) | Hcy | Dab | 156 |
| 156 | KKK-(Hcy)-TPRGDSFA(Dab(acetyl)) | Hcy | Dab | 157 |
| 157 | KKK-(Hcy)-TTRGDSFA(Dab(acetyl)) | Hcy | Dab | 158 |
| 158 | KKKA-(Hcy)-TPRGDTFA(Dab(acetyl)) | Hcy | Dab | 159 |
| 159 | KKK-(Hcy)-TPRGDTFA(Dab(acetyl))A | Hcy | Dab | 160 |
| 160 | KKKA-(Hcy)-TPRGDTFA(Dab(acetyl))A | Hcy | Dab | 161 |
| 161 | KKKA-(Hcy)-TTRGDSFA(Dab(acetyl))A | Hcy | Dab | 162 |
| 162 | KKKA-(Hcy)-IPRGDSFA(Dab(acetyl)) | Hcy | Dab | 163 |
| 163 | KKK-(Hcy)-IPRGDSFA(Dab(acetyl))A | Hcy | Dab | 164 |
| 164 | KKKA-(Hcy)-VPRGDTFA(Dab(acetyl)) | Hcy | Dab | 165 |
| 165 | KKK-(Hcy)-VPRGDTFA(Dab(acetyl))A | Hcy | Dab | 166 |

Among these cyclic peptides, the cyclic peptides 1 to 137 and the cyclic peptides 144 to 165 are preferable from the viewpoint of molecule stability. Further, the cyclic peptides 1 to 127 and the cyclic peptides 144 to 165 are more preferable from the viewpoint of the balance between molecule stability and integrin binding property. The cyclic peptides 1, 92, 108, and 160 are still more preferable, and the cyclic peptides 92, 108, and 160 are still more preferable. Even in a case of applying the above-described regulation of the addition, deletion, or substitution of the amino acid residue, or the above-described regulation of the sequence identity, it is preferable that a region between the crosslinking moiety amino acids of the cyclic segment in the above preferred cyclic peptide is applied as the reference sequence.

The sequence variation may be applied by considering the entire cyclic peptide as a reference sequence. As a result, an amino acid sequence, in which an amino acid residue is added, deleted, or substituted with respect to any one of the amino acid sequences of SEQ ID NO: 2 to SEQ ID NO: 166, is capable of being used as long as the requirements of the cyclic peptide according to the present disclosure are satisfied. However, the RGD region in the cyclic segment should not be modified. In a case of adding, deleting, or substituting an amino acid residue with respect to any one of the amino acid sequences of SEQ ID NO: 2 to SEQ ID NO: 166, the total number of amino acid residues added, deleted, or substituted is preferably 1 to 15, more preferably 1 to 10, still more preferably 1 to 5, even still more preferably 1 to 3, and even further still more preferably 1 or 2.

The cyclic peptide according to the present disclosure preferably has a sequence identity of 70% or more, more preferably has a sequence identity of 80% or more, and still more preferably has a sequence identity of 90%, with respect to any one of the amino acid sequences of SEQ ID NO: 2 to SEQ ID NO: 166. For example, the range of the amino acid sequence having a sequence identity of 70% or more with respect to the amino acid sequence of SEQ ID NO: 2 also includes the amino acid sequence of SEQ ID NO: 2 itself The present disclosure also provides a cell scaffold material (hereinafter, also referred to as a cell scaffold material according to the present disclosure) containing a base material and the cyclic peptide according to the present disclosure. Cells are supported by an extracellular matrix in vivo, and thus in a case where a cell scaffold material that reproduces the same state as above is used, it is possible to culture cells better. Examples of the base material for cell culture include a matrix composed of biodegradable polyesters such as polylactic acid, polyglycolic acid, and polycaprolactone, collagen or gelatin which is a heat-denatured product of collagen, glycoproteins such as fibronectin, or polysaccharides such as hyaluronic acid, chitin, and alginic acid. For example, in a case where the immobilizing functional group in the cyclic peptide according to the present disclosure is reacted with a functional group in the base material, the cyclic peptide according to the present disclosure can be bound to the base material. For example, in a case where the cyclic peptide according to the present disclosure has an amino group of a lysine residue as the immobilizing functional group, the amino group is reacted with a carboxy group on the base material to form an amide bond, whereby the cyclic peptide can be immobilized to the base material. In a case of using such a method, it is possible to obtain a cell scaffold material in which the cyclic peptide according to the present disclosure is bound to the surface of the base material. The amount of the cyclic peptide according to the present disclosure is not particularly limited; however, it may be 0.01% by mass to 100% by mass and may be 0.1% by mass to 50% by mass with respect to the base material.

The cell scaffold material according to the present disclosure can be applied onto any culture tool such as a petri dish, a flask, a plate (for example, a polystyrene well plate), a culture bag, a hollow fiber membrane, or beads. Since the cell scaffold material according to the present disclosure contains the cyclic peptide according to the present disclosure, it has a good binding property to integrin, and thus cells can adhere well to the cell scaffold material. Here, the cell to be cultured is not particularly limited as long as it is a cell of an organism expressing integrin; however, it may be any animal cell, may be any vertebrate animal cell, may be any mammal cell, and may be a human cell or a non-human mammal cell. Examples of the cell include an embryonic stem (ES) cell, an induced pluripotent stem (iPS) cell, a perinatal stem cell, an amniotic fluid-derived stem cell (AFSC), a mesenchymal stem cell (MSC) of any origin, any tissue-type progenitor cell or adult cell of which the differentiation direction has been determined, a mature cell, a normal cell, an affected cell, and a tumor cell. More specific examples thereof include a liver cell, a parenchymal cell, a stellate cell, an endothelial cell, a hepatocyte, a bile duct cell, a biliary tree cell, and a pancreatic cell. Examples of these cells are also applied to the cell separating material and the medium described later.

The present disclosure also provides a cell separating material (hereinafter, also referred to as a cell separating material according to the present disclosure) containing a holding material and the cyclic peptide according to the present disclosure. Since the cell separating material according to the present disclosure contains the cyclic peptide according to the present disclosure, it can bind to the integrin on the cell surface and capture cells. As a result, in a case where the cell separating material according to the present disclosure is used, for example, in affinity chromatography, cells can be efficiently separated from the cell suspension.

For example, in a case where an immobilizing functional group in the cyclic peptide according to the present disclosure is reacted with a functional group in the holding material, the cyclic peptide according to the present disclosure can be bound to the holding material. For example, in a case where the cyclic peptide according to the present disclosure has an amino group of a lysine residue as the immobilizing functional group, the amino group is reacted with a carboxy group on the holding material to form an amide bond, whereby the cyclic peptide can be immobilized to the holding material.

The holding material may be composed of a material selected from, for example, polysaccharides such as agarose, dextran, starch, cellulose, pullulan, chitin, chitosan, cellulose triacetate, and cellulose diacetate, and derivatives thereof, and vinyl-based polymers such polyacrylamide, polymethacrylamide, polyacrylate, polymethacrylate, polyalkyl vinyl ether, and polyvinyl alcohol. These materials may form a crosslinking structure. The crosslinking structure tends to improve mechanical strength. The holding material is preferably composed of one or more of the above materials.

In addition, the holding material is preferably porous, more preferably a porous membrane or porous particles, and still more preferably porous particles.

A cell separating material in which the cyclic peptide according to the present disclosure is immobilized to a water-insoluble holding material can also be used in affinity chromatography. Examples of the water-insoluble holding material include polysaccharides such as crystalline cellulose, crosslinked cellulose, crosslinked agarose, crosslinked dextran, and crosslinked pullulan, organic holding materials such as an acrylate-based polymer, and a styrene-based polymer, inorganic holding material such as a glass bead and silica gel, and composite holding materials obtained by combining these, such as an organic-organic type and an organic-inorganic type. The water-insoluble holding material is more preferably polysaccharides or an acrylate-based polymer and still more preferably polysaccharides such as agarose and cellulose from the viewpoint of alkali resistance. Examples of the commercially available product that can be used as a water-insoluble holding material include Cellufine (CELLUFINE is a registered trade name) GCL2000 (manufactured by INC Corporation) and Cellufine MAX (manufactured by INC Corporation), which are porous cellulose gels; Sephacryl (SEPHACRYL is a registered trade name) S-1000 SF (manufactured by GE Healthcare) in which allyl dextran and methylenebisacrylamide are covalently crosslinked; TOYOPEARL (TOYOPEARL is a registered trade name) (manufactured by Tosoh Corporation), TOYOPEARL AF-Carboxy-650 (manufactured by Tosoh Corporation), and TOYOPEARL GigaCap CM-650 (manufactured by Tosoh Corporation), which is an acrylate-based holding material; Sepharose (SEPHAROSE is a registered trade name) CL4B (manufactured by GE Healthcare), which is agarose-based crosslinked holding material; and Eupergit (EUPERGIT is a registered trade name) C250L (manufactured by Sigma-Aldrich Co., LLC.), which is a polymethacrylamide activated with an epoxy group. However, the water-insoluble holding material in the present disclosure is not limited to these holding materials or activated holding materials. In addition, the water-insoluble holding material that is used in the present disclosure preferably has a large surface area and is preferably a porous material having a large number of pores of a proper size in consideration of the using purpose and the using method of the present adsorbing material. The form of the holding material is not particularly limited. Any form such as a bead shape, a fibrous shape, a membrane shape, or a hollow yarn shape, is possible, and any form can be selected.

Examples of the method of immobilizing the cyclic peptide according to the present disclosure to a water-insoluble holding material include, which are not limited to, an immobilization method using an amino group of a lysine residue as described above. It is possible to adopt a method generally adopted in a case of immobilizing a protein or a polypeptide to a holding material. Examples thereof include a method in which a holding material is reacted with cyanogen bromide, epichlorohydrin, diglycidyl ether, tosyl chloride, tresyl chloride, hydrazine, or the like to activate the holding material or introduce a reactive functional group on the surface of the holding material and a reaction with the cyclic peptide according to the present disclosure is carried out for immobilization and an immobilization method in which a condensing reagent such as carbodiimide or a reagent having a plurality of functional groups in the molecule, such as glyceraldehyde, is added to a system in which a holding material and the cyclic peptide according to the present disclosure are present to carry out condensation and crosslinking In a case of immobilizing the cyclic peptide according to the present disclosure to a holding material, it is preferable to dissolve (disperse) the cyclic peptide according to the present disclosure in an aqueous solvent (an aqueous dispersion medium) or an organic solvent (an organic dispersion medium). The aqueous solvent (the aqueous dispersion medium) is not particularly limited; however, examples thereof include a 4-(2-hydroxyethyl)-1-piperazineethanesulfonic acid (HEPES) buffer solution, an acetate buffer solution, a phosphate buffer solution, a citrate buffer solution, and a Tris-hydrochloride buffer solution. The organic solvent (the organic dispersion medium) is not particularly limited; however, a polar organic solvent is preferable, and dimethyl sulfoxide (DMSO), N,N-dimethylformamide (DMF), or alcohol is particularly preferable. Examples thereof include methanol, ethanol, isopropyl alcohol (IPA), 2,2,2-trifluoroethanol (TFE), and 1,1,1,3,3,3-hexafluoro-2-propanol (HFIP).

The pH condition for immobilizing the cyclic peptide according to the present disclosure is not particularly limited, and may be any condition of acidic, neutral, or alkaline condition, and may be appropriately set according to, for example, the solvent (the dispersion medium) to be used.

For example, in a case of making the condition alkaline, a base such as diazabicycloundecene (DBU) or triethylamine (TEA) may be added to dimethyl sulfoxide (DMSO) or alcohol.

In a case where the above cell separating material is used as a packing material for affinity chromatography, the density of the cyclic peptide according to the present disclosure is not particularly limited; however, it is preferably 0.1 to 1,000 mmol/1 L packing material, more preferably 0.1 to 100 mmol/1 L packing material, and still more preferably 0.5 to 20 mmol/1 L packing material. Within this range, the using amount of the cyclic peptide according to the present disclosure is well balanced with the cell separation performance, and cells can be separated efficiently at a lower cost.

The cell that is separated by the cell separating material according to the present disclosure is not particularly limited as long as it is a cell of an organism expressing integrin; however, it may be any animal cell, may be any vertebrate animal cell, may be any mammal cell, and may be a human cell or a non-human mammal cell.

The present disclosure also provides a medium (hereinafter, also referred to as a medium according to the present disclosure) containing a culture component and the cyclic peptide according to the present disclosure. In a case where the cyclic peptide according to the present disclosure is contained in the medium, the binding of the integrin of the cell cultured in the medium to the cyclic peptide occurs, which provides an effect such as an increase in cell viability through apoptosis suppression due to signal transduction from the integrin. The culture component refers to a medium component for culturing cells. Here, the cell to be cultured is not particularly limited as long as it is a cell of an organism expressing integrin; however, it may be any animal cell, may be any vertebrate animal cell, may be any mammal cell, and may be a human cell or a non-human mammal cell. As the medium that is used as a culture component, an appropriate medium may be selected according to the kind of cells to be cultured. Examples thereof include Dulbecco modified Eagle's medium (DMEM), Eagle's minimum essential medium (MEM), F12, Ham, RPMI 1640, MCDB (MCDB 102, 104, 107, 131, 153, 199, or the like), L15, SkBM (registered trade name), RITC80-7, and MesenPro (Thermo Fisher Scientific, Inc.).

As the culture component, a medium such as the above-described medium may be used as it is in the state of the standard composition (for example, as it is in the state of having been sold), or the composition may be appropriately changed according to the cell kind or the cell conditions. Accordingly, the culture component is not limited to the one having a known composition, and one or two or more components may be added, removed, increased, or decreased.

The amino acids to be contained in the culture component are not particularly limited; however, examples thereof include L-arginine, L-cystine, L-glutamine, glycine, L-histidine, L-isoleucine, L-leucine, L-lysine, L-methionine, L-phenylalanine, L-serine, L-threonine, L-tryptophan, L-tyrosine, and L-valine.

The vitamins to be contained in the culture component is not particularly limited; however, examples thereof include calcium D-pantothenate, choline chloride, folic acid, i-inositol, niacinamide, riboflavin, thiamine, pyridoxine, biotin, lipoic acid, vitamin B12, adenine, and thymidine.

The electrolyte to be contained in the culture component is not particularly limited; however, examples thereof include $CaCl_2$, KCl, $MgSO_4$, NaCl, $NaH_2PO_4$, $NaHCO_3$, $Fe(NO_3)_3$, $FeSO_4$, $CuSO_4$, $MnSO_4$, $Na_2SiO_3$, $(NH_4)_6Mo_7O_{24}$, $NaVO_3$, $NiCl_2$, and $ZnSO_4$.

In addition to these components, the culture component may contain sugars such as D-glucose, sodium pyruvate, a pH indicator such as phenol red, putrescine, and an antibiotic.

The culture component may contain or may not contain serum. The content of the serum in the medium according to the present disclosure is preferably 0% by volume or more and 30% by volume or less, more preferably 0% by volume or more and 10% by volume or less, and still more preferably 0% by volume or more and 5% by volume or less, and particularly preferably 0% by volume or more and 2% by volume or less.

The content of the cyclic peptide according to the present disclosure in the medium according to the present disclosure is not particularly limited; however, it is, for example, 0.01 ng/mL to 10 mg/mL and may be 0.1 ng/mL to 1 mg/mL. In the medium according to the present disclosure, unlike the case of the cell scaffold material or the cell separating material, it is not particularly necessary to immobilize the cyclic peptide.

As described above, according to the present disclosure, it is possible to provide a cyclic peptide excellent in the binding property to integrin and excellent in the molecule stability, for example, in the alkali resistance, and a cell scaffold material, a cell separating material, and a medium, which contain the cyclic peptide.

EXAMPLES

The embodiments according to the present disclosure will be described in more detail with reference to Examples below; however, the embodiments are not limited thereto.

(1) Synthesis of Cyclic Peptide

Each of the cyclic peptides 1 to 146 shown in Table 3 to Table 7 and the cyclic peptides 147 and 148 shown in Table 8 below was synthesized by using a fully automated peptide synthesizer (PSSM-8, manufactured by Shimadzu Corporation). In a case where optical isomers are present in amino acid residues contained in the cyclic peptide prepared in Examples, all the amino acid residues are L-form isomers. That is, for example, the notation D in the peptide prepared in Example represents an L-aspartic acid residue. In Table 8, the amino acid residues shown in parentheses indicate amino acid residues involved in the intramolecular crosslinking by the thioether bond.

TABLE 8

| Number | Amino acid sequence (N terminal -> C terminal) | Crosslinking moiety amino acid residue $X^a$ | $X^b$ | SEQ ID NO. |
|---|---|---|---|---|
| 166 | KKKA(Dap(acetyl))EPRGDNYR(C) | Dap | C | 167 |
| 167 | KKK(Dap(acetyl))EPRGDNYR(C) | Dap | C | 168 |

(2) Immobilization of Cyclic Peptide

A commercially available CMS (a carboxymethyl dextran introduction type, manufactured by GE Healthcare) sensor chip was set in Biacore 3000, which is a surface plasmon resonance apparatus manufactured by GE Healthcare, the sensor was stabilized at a flow rate of 10 μL/min of a HEPES (4-(2-hydroxyethyl)-1-piperazineethanesulfonic acid) buffer solution (20 mM HEPES-HCl, 150 mM NaCl, pH 7.4) for surface plasmon resonance (SPR), and 70 μL of a mixed aqueous solution of 0.2 M 1-(3-dimethylaminopropyl)-3-ethylcarbodiimide (EDC) and 0.04 M N-hydroxysuccinimide (NHS) was added thereto. Here, the concentration unit M represents mol/L, and the same applies hereinafter. Then, 20 μL of the sample solution of each of the above cyclic peptides diluted to 0.2 g/L with the HEPES buffer solution was supplied to the sensor chip, blocking treatment was subsequently carried out with an ethanolamine solution, and washing was carried out with a sodium hydroxide aqueous solution, whereby immobilization was carried out. However, only for the cyclic peptides 125, 126, and 127, in which the number of lysine residues having an amino group as the immobilizing functional group was zero, the amount of the sample solution to be supplied to the sensor chip was set to 500 μL instead of 20 μL. Further, 70 μL of the mixed aqueous solution of 0.2 M EDC and 0.04 M NHS was added to another flow channel of the same sensor chip without immobilizing the sample, and then blocking treatment and washing treatment were carried out. Hereinafter, the obtained immobilization-treated sensor chip is referred to as an "immobilization-treated sensor chip A".

(3) Evaluation of Integrin Binding Property

After adding human integrin αvβ5 for 10 minutes at 25° C., which was diluted to 30 nM using a HEPES buffer solution to which magnesium chloride was added to 5 mM, in each flow channel of the immobilization-treated sensor chip A prepared in (1) above, the same HEPES buffer solution (containing 5 mM magnesium chloride) was allowed to flow as a running buffer for 30 minutes, and measurement was carried out with Biacore 3000. Then, a regeneration treatment of removing human integrin αvβ5 was carried out by allowing a 0.5 M EDTA aqueous solution to flow through each flow channel for 10 minutes. Further, the above-described measurement process consisting of adding integrin for 10 minutes, allowing a running buffer to flow for 30 minutes, carrying out measurement with Biacore 3000, and carrying out regeneration treatment with 0.5 M EDTA aqueous solution was carried out in the same manner for 100 nM human integrin αvβ5, 300 nM human integrin αvβ5, and 1,000 nM human integrin αvβ5. Dissociation constant between the cyclic peptide and human integrin αvβ5 was calculated from the difference between the value measured by Biacore 3000 in the flow channel immobilized with the cyclic peptide and the value measured by Biacore 3000 in the flow channel unimmobilized with the cyclic peptide, in a case where each concentration of human integrin αvβ5 was allowed to flow, and the integrin binding property was evaluated according to the following evaluation standards. It is preferable that the evaluation result satisfies the evaluation standard A, B, or C.

| (Evaluation standards for dissociation constant) |
|---|
| A . . . The dissociation constant is 50 nM or less. |
| B . . . The dissociation constant is more than 50 nM and 100 nM or less. |
| C . . . The dissociation constant is more than 100 nM and 200 nM or less. |
| D . . . The dissociation constant is more than 200 nM. |

The evaluation results are shown in the corresponding columns of Table 9 to Table 13.

In a case where the cyclic peptide exhibiting integrin binding property of ranks A to C is used, the specific binding between the cyclic peptide and integrin is possible, and thus more efficient cell control is possible.

(4) Evaluation of Molecule Stability

The molecule stability of the cyclic peptide was evaluated by analyzing the alkali-treated cyclic peptide aqueous solution by liquid chromatography mass spectroscopy (LC/MS).

The alkali treatment was carried out by the following method. A 500 μM cyclic peptide aqueous solution was prepared, an equivalent of 1 M sodium hydroxide aqueous solution was added to this aqueous solution, and the resultant mixture was incubated at 15° C. for 3 hours to obtain an alkali-treated cyclic peptide aqueous solution. The cyclic peptide residual rate was calculated by setting the total area of all peaks of the cyclic peptide before alkali treatment in LC/MS to 100% and determining the proportion of the total area of all peaks in LC/MS of the alkali-treated cyclic peptide aqueous solution, and the molecule stability was evaluated according to the following evaluation standards. It is preferable that the evaluation result satisfies the evaluation standard A, B, or C.

| (Evaluation standards for residual rate of cyclic peptide) |
|---|
| A . . . The residual rate of the cyclic peptide is 70% or more. |
| B . . . The residual rate of the cyclic peptide is 50% or more and less than 70%. |
| C . . . The residual rate of the cyclic peptide is 30% or more and less than 50%. |
| D . . . The residual rate of the cyclic peptide is less than 30%. |

The conditions of the LC/MS used for the evaluation of molecule stability were set as follows.

LC apparatus: Prominence series (pump, column oven, autosampler, detector) (manufactured by Shimadzu Corporation)

MS detector: LC/MS2010EV (manufactured by Shimadzu Corporation)

Column: Cadenza CD-C18, inner diameter 2.0 mm×length 250 mm, particle size: 3 μm (manufactured by Imtakt Corporation)

Eluent A: a solution (pH 3) containing 10 mM ammonium formate as a solute, where the solvent is 100% water.

Eluent B: a solution (pH 3) containing 10 mM ammonium formate as a solute, where the solvent is acetonitrile/water=90/10.

Flow rate: 0.2 mL/min

Injection volume: 4 µL

Gradient: 0% to 30%: Eluent B (0 to 30 minutes), 100%: Eluent B (30 to 40 minutes), 0%: Eluent B (40 to 60 minutes)

Column temperature: 45° C.

Ionization method: electrospray ionization (ESI) positive, ESI negative

The evaluation results are shown in the corresponding columns of Table 9 to Table 13.

In a case where the cyclic peptides exhibiting molecule stability of the ranks A to C are used, the cyclic peptide can be specifically bound to cells even in a case of being used for a long period of time or repeatedly, cell control is possible even in a case of being used in a long-term or repeated process, and thus the cost can be further reduced.

The evaluation results of the integrin binding property and the molecule stability of the cyclic peptides 1 to 167 are summarized in Table 9 to Table 13 below. As in Table 3 to Table 7, in the column of "Crosslinking moiety amino acid residue", the acetyl group is omitted.

TABLE 9

| Cyclic peptide | | | | | | |
|---|---|---|---|---|---|---|
| | Crosslinking moiety amino acid residue | | Performance evaluation | | | |
| Identification name | $X^a$ | $X^b$ | Binding activity | Stability | SEQ ID NO. | Note |
| Cyclic peptide 1 | Hcy | Dab | A | A | 2 | Example |
| Cyclic peptide 2 | Hcy | Dab | A | A | 3 | Example |
| Cyclic peptide 3 | Hcy | Dab | A | A | 4 | Example |
| Cyclic peptide 4 | Hcy | Dab | A | A | 5 | Example |
| Cyclic peptide 5 | Hcy | Dab | A | A | 6 | Example |
| Cyclic peptide 6 | Hcy | Dab | B | A | 7 | Example |
| Cyclic peptide 7 | Hcy | Dab | A | A | 8 | Example |
| Cyclic peptide 8 | Hcy | Dab | B | A | 9 | Example |
| Cyclic peptide 9 | Hcy | Dab | C | A | 10 | Example |
| Cyclic peptide 10 | Hcy | Dab | B | A | 11 | Example |
| Cyclic peptide 11 | Hcy | Dab | A | A | 12 | Example |
| Cyclic peptide 12 | Dap | Hcy | B | B | 13 | Example |
| Cyclic peptide 13 | Hcy | Dab | A | A | 14 | Example |
| Cyclic peptide 14 | Hcy | Dab | A | A | 15 | Example |
| Cyclic peptide 15 | Hcy | Dab | B | A | 16 | Example |
| Cyclic peptide 16 | Hcy | Dab | B | A | 17 | Example |
| Cyclic peptide 17 | Hcy | Dab | B | A | 18 | Example |
| Cyclic peptide 18 | Hcy | Dab | B | A | 19 | Example |
| Cyclic peptide 19 | Hcy | Dab | A | A | 20 | Example |
| Cyclic peptide 20 | Hcy | Dab | B | A | 21 | Example |
| Cyclic peptide 21 | Hcy | Dab | A | A | 22 | Example |
| Cyclic peptide 22 | Hcy | Dab | B | A | 23 | Example |
| Cyclic peptide 23 | Hcy | Dab | A | A | 24 | Example |
| Cyclic peptide 24 | Hcy | Dab | A | A | 25 | Example |
| Cyclic peptide 25 | Hcy | Dab | B | A | 26 | Example |
| Cyclic peptide 26 | Hcy | Dab | B | A | 27 | Example |
| Cyclic peptide 27 | Hcy | Dab | A | A | 28 | Example |
| Cyclic peptide 28 | Hcy | Dab | B | A | 29 | Example |
| Cyclic peptide 29 | Hcy | Dab | B | A | 30 | Example |
| Cyclic peptide 30 | Hcy | Dab | A | A | 31 | Example |
| Cyclic peptide 31 | Hcy | Dab | A | A | 32 | Example |
| Cyclic peptide 32 | Hcy | Dab | A | A | 33 | Example |
| Cyclic peptide 33 | Hcy | Dab | C | A | 34 | Example |
| Cyclic peptide 34 | Hcy | Dab | A | A | 35 | Example |
| Cyclic peptide 35 | Hcy | Dab | C | A | 36 | Example |
| Cyclic peptide 36 | Hcy | Dab | B | A | 37 | Example |
| Cyclic peptide 37 | Hcy | Dab | B | A | 38 | Example |
| Cyclic peptide 38 | Hcy | Dab | B | A | 39 | Example |
| Cyclic peptide 39 | Hcy | Dab | A | A | 40 | Example |
| Cyclic peptide 40 | Hcy | Dab | B | A | 41 | Example |

TABLE 10

| Cyclic peptide | | | | | | |
|---|---|---|---|---|---|---|
| | Crosslinking moiety amino acid residue | | Performance evaluation | | | |
| Identification name | $X^a$ | $X^b$ | Binding activity | Stability | SEQ ID NO. | Note |
| Cyclic peptide 41 | Hcy | Dab | B | A | 42 | Example |
| Cyclic peptide 42 | Hcy | Dab | B | A | 43 | Example |
| Cyclic peptide 43 | Hcy | Dab | B | A | 44 | Example |
| Cyclic peptide 44 | Hcy | Dab | B | A | 45 | Example |
| Cyclic peptide 45 | Hcy | Dab | B | A | 46 | Example |
| Cyclic peptide 46 | Dap | Hcy | B | B | 47 | Example |
| Cyclic peptide 47 | Dap | Hcy | B | B | 48 | Example |
| Cyclic peptide 48 | Dap | Hcy | A | B | 49 | Example |
| Cyclic peptide 49 | Hcy | Dab | B | A | 50 | Example |
| Cyclic peptide 50 | Hcy | Dab | C | A | 51 | Example |
| Cyclic peptide 51 | Hcy | Dab | C | A | 52 | Example |
| Cyclic peptide 52 | Dap | Hcy | B | B | 53 | Example |
| Cyclic peptide 53 | Dap | Hcy | B | B | 54 | Example |
| Cyclic peptide 54 | Hcy | Dab | A | A | 55 | Example |
| Cyclic peptide 55 | Hcy | Dab | A | A | 56 | Example |
| Cyclic peptide 56 | Hcy | Dab | A | A | 57 | Example |
| Cyclic peptide 57 | Hcy | Dab | A | A | 58 | Example |
| Cyclic peptide 58 | Hcy | Dab | A | A | 59 | Example |
| Cyclic peptide 59 | Hcy | Dab | A | A | 60 | Example |
| Cyclic peptide 60 | Hcy | Dab | A | A | 61 | Example |

TABLE 11

| Cyclic peptide | | | | | | |
|---|---|---|---|---|---|---|
| | Crosslinking moiety amino acid residue | | Performance evaluation | | | |
| Identification name | $X^a$ | $X^b$ | Binding activity | Stability | SEQ ID NO. | Note |
| Cyclic peptide 61 | Hcy | Dab | A | A | 62 | Example |
| Cyclic peptide 62 | Hcy | Dab | A | A | 63 | Example |
| Cyclic peptide 63 | Hcy | Dab | A | A | 64 | Example |
| Cyclic peptide 64 | Hcy | Dab | A | A | 65 | Example |
| Cyclic peptide 65 | Hcy | Dab | B | A | 66 | Example |
| Cyclic peptide 66 | Hcy | Dab | A | A | 67 | Example |
| Cyclic peptide 67 | Hcy | Dab | A | A | 68 | Example |
| Cyclic peptide 68 | Hcy | Dab | A | A | 69 | Example |
| Cyclic peptide 69 | Hcy | Dab | A | A | 70 | Example |
| Cyclic peptide 70 | Hcy | Dab | A | A | 71 | Example |
| Cyclic peptide 71 | Hcy | Dab | A | A | 72 | Example |
| Cyclic peptide 72 | Hcy | Dab | B | A | 73 | Example |
| Cyclic peptide 73 | Hcy | Dab | B | A | 74 | Example |
| Cyclic peptide 74 | Hcy | Dab | A | A | 75 | Example |
| Cyclic peptide 75 | Hcy | Dab | A | A | 76 | Example |
| Cyclic peptide 76 | Hcy | Dab | B | A | 77 | Example |
| Cyclic peptide 77 | Hcy | Dab | A | A | 78 | Example |
| Cyclic peptide 78 | Hcy | Dab | A | A | 79 | Example |
| Cyclic peptide 79 | Hcy | Dab | B | A | 80 | Example |
| Cyclic peptide 80 | Hcy | Dab | B | A | 81 | Example |
| Cyclic peptide 81 | Hcy | Dab | B | A | 82 | Example |
| Cyclic peptide 82 | Hcy | Dab | B | A | 83 | Example |
| Cyclic peptide 83 | Hcy | Dab | A | A | 84 | Example |
| Cyclic peptide 84 | Hcy | Dab | A | A | 85 | Example |
| Cyclic peptide 85 | Hcy | Dab | A | A | 86 | Example |
| Cyclic peptide 86 | Hcy | Dab | A | A | 87 | Example |
| Cyclic peptide 87 | Hcy | Dab | A | A | 88 | Example |
| Cyclic peptide 88 | Hcy | Dab | A | A | 89 | Example |
| Cyclic peptide 89 | Hcy | Dab | A | A | 90 | Example |
| Cyclic peptide 90 | Hcy | Dab | A | A | 91 | Example |
| Cyclic peptide 91 | Hcy | Dab | A | A | 92 | Example |
| Cyclic peptide 92 | Hcy | Dab | A | A | 93 | Example |
| Cyclic peptide 93 | Hcy | Dab | A | A | 94 | Example |
| Cyclic peptide 94 | Hcy | Dab | A | A | 95 | Example |
| Cyclic peptide 95 | Hcy | Dab | A | A | 96 | Example |

TABLE 11-continued

| Cyclic peptide | | | | | | | |
|---|---|---|---|---|---|---|---|
| | Crosslinking moiety amino acid residue | | Performance evaluation | | | | |
| Identification name | $X^a$ | $X^b$ | Binding activity | Stability | SEQ ID NO. | Note |
| Cyclic peptide 96 | Hcy | Dab | A | A | 97 | Example |
| Cyclic peptide 97 | Hcy | Dab | A | A | 98 | Example |
| Cyclic peptide 98 | Hcy | Dab | A | A | 99 | Example |
| Cyclic peptide 99 | Hcy | Dab | A | A | 100 | Example |
| Cyclic peptide 100 | Hcy | Dab | A | A | 101 | Example |

TABLE 12

| Cyclic peptide | | | | | | |
|---|---|---|---|---|---|---|
| | Crosslinking moiety amino acid residue | | Performance evaluation | | | |
| Identification name | $X^a$ | $X^b$ | Binding activity | Stability | SEQ ID NO. | Note |
| Cyclic peptide 101 | Hcy | Dab | A | A | 102 | Example |
| Cyclic peptide 102 | Hcy | Dab | A | A | 103 | Example |
| Cyclic peptide 103 | Hcy | Dab | A | A | 104 | Example |
| Cyclic peptide 104 | Hcy | Dab | A | A | 105 | Example |
| Cyclic peptide 105 | Hcy | Dab | A | A | 106 | Example |
| Cyclic peptide 106 | Hcy | Dab | A | A | 107 | Example |
| Cyclic peptide 107 | Hcy | Dab | A | A | 108 | Example |
| Cyclic peptide 108 | Hcy | Dab | A | A | 109 | Example |
| Cyclic peptide 109 | Hcy | Dab | A | A | 110 | Example |
| Cyclic peptide 110 | Hcy | Dab | A | A | 111 | Example |
| Cyclic peptide 111 | Hcy | Dab | A | A | 112 | Example |
| Cyclic peptide 112 | Hcy | Dab | A | A | 113 | Example |
| Cyclic peptide 113 | Hcy | Dab | B | A | 114 | Example |
| Cyclic peptide 114 | Hcy | Dap | A | B | 115 | Example |
| Cyclic peptide 115 | Hcy | Orn | A | A | 116 | Example |
| Cyclic peptide 116 | Hcy | K | A | A | 117 | Example |
| Cyclic peptide 117 | Dap | Hcy | A | B | 118 | Example |
| Cyclic peptide 118 | Dab | Hcy | A | A | 119 | Example |
| Cyclic peptide 119 | Orn | Hcy | A | A | 120 | Example |
| Cyclic peptide 120 | K | Hcy | B | A | 121 | Example |
| Cyclic peptide 121 | Hcy | K | A | A | 122 | Example |
| Cyclic peptide 122 | Dab | Hcy | A | A | 123 | Example |
| Cyclic peptide 123 | Hcy | K | A | A | 124 | Example |
| Cyclic peptide 124 | Dab | Hcy | B | A | 125 | Example |
| Cyclic peptide 125 | Hcy | Dab | A | A | 126 | Example |
| Cyclic peptide 126 | Hcy | Dab | A | A | 127 | Example |
| Cyclic peptide 127 | Hcy | Dab | A | A | 128 | Example |
| Cyclic peptide 128 | Pen | Dap | A | B | 129 | Example |
| Cyclic peptide 129 | Pen | Dab | B | A | 130 | Example |
| Cyclic peptide 130 | Pen | Orn | A | A | 131 | Example |
| Cyclic peptide 131 | Pen | K | B | A | 132 | Example |
| Cyclic peptide 132 | Dap | Pen | A | A | 133 | Example |
| Cyclic peptide 133 | Dab | Pen | B | A | 134 | Example |
| Cyclic peptide 134 | Orn | Pen | A | A | 135 | Example |
| Cyclic peptide 135 | K | Pen | B | A | 136 | Example |
| Cyclic peptide 136 | Dab | Pen | A | A | 137 | Example |
| Cyclic peptide 137 | Dab | Pen | B | A | 138 | Example |
| Cyclic peptide 138 | Dab | C | B | C | 139 | Example |
| Cyclic peptide 139 | Orn | C | A | C | 140 | Example |
| Cyclic peptide 140 | K | C | B | C | 141 | Example |

TABLE 13

| Cyclic peptide | | | | | | |
|---|---|---|---|---|---|---|
| | Crosslinking moiety amino acid residue | | Performance evaluation | | | |
| Identification name | $X^a$ | $X^b$ | Binding activity | Stability | SEQ ID NO. | Note |
| Cyclic peptide 141 | Dab | C | A | C | 142 | Example |
| Cyclic peptide 142 | Dab | C | A | C | 143 | Example |
| Cyclic peptide 143 | Dab | C | A | C | 144 | Example |
| Cyclic peptide 144 | Hcy | Dab | A | A | 145 | Example |
| Cyclic peptide 145 | Hcy | Dab | A | A | 146 | Example |
| Cyclic peptide 146 | Hcy | Dab | A | A | 147 | Example |
| Cyclic peptide 147 | Hcy | Dab | A | A | 148 | Example |
| Cyclic peptide 148 | Hcy | Dab | A | A | 149 | Example |
| Cyclic peptide 149 | Hcy | Dab | A | A | 150 | Example |
| Cyclic peptide 150 | Hcy | Dab | A | A | 151 | Example |
| Cyclic peptide 151 | Hcy | Dab | A | A | 152 | Example |
| Cyclic peptide 152 | Hcy | Dab | A | A | 153 | Example |
| Cyclic peptide 153 | Hcy | Dab | A | A | 154 | Example |
| Cyclic peptide 154 | Hcy | Dab | B | A | 155 | Example |
| Cyclic peptide 155 | Hcy | Dab | A | A | 156 | Example |
| Cyclic peptide 156 | Hcy | Dab | B | A | 157 | Example |
| Cyclic peptide 157 | Hcy | Dab | A | A | 158 | Example |
| Cyclic peptide 158 | Hcy | Dab | A | A | 159 | Example |
| Cyclic peptide 159 | Hcy | Dab | A | A | 160 | Example |
| Cyclic peptide 160 | Hcy | Dab | A | A | 161 | Example |
| Cyclic peptide 161 | Hcy | Dab | B | A | 162 | Example |
| Cyclic peptide 162 | Hcy | Dab | A | A | 163 | Example |
| Cyclic peptide 163 | Hcy | Dab | A | A | 164 | Example |
| Cyclic peptide 164 | Hcy | Dab | A | A | 165 | Example |
| Cyclic peptide 165 | Hcy | Dab | A | A | 166 | Example |
| Cyclic peptide 166 | Dap | C | A | D | 167 | Comparative Example |
| Cyclic peptide 167 | Dap | C | B | D | 168 | Comparative Example |

As can be seen from the results in Table 9 to Table 13, the cyclic peptides 1 to 165 according to the present disclosure have a practically sufficient integrin binding property and a practically sufficient molecule stability. All of the cyclic peptides 1 to 165 according to the present disclosure had a residual rate value of more than 35% in the evaluation of molecule stability. On the other hand, in the cyclic peptide 166 and the cyclic peptide 167, in which the sulfur atom of the cysteine residue and the α carbon of another amino acid residue were separated by four or fewer atoms, a practically sufficient molecule stability could be obtained. In particular, both the cyclic peptide 166 and the cyclic peptide 167 had a value of a residual rate of less than 25% in the evaluation of molecule stability.

In addition, the cyclic peptides 1 to 137 and the cyclic peptides 144 to 165, where the amino acid residue in which the number (the total number of carbon atoms, including a branch moiety in a case where the branch is present) of carbon atoms on the side chain containing the sulfur atom is 2 to 10 is one of amino acid residues involved in the intramolecular crosslinking, have an improved molecule stability as compared with the cyclic peptides 138 to 143, where the cysteine residue in which the number of carbon atoms on the side chain having the sulfur atom is one is one of amino acid residues involved in the intramolecular crosslinking Further, for example, as can be seen from the comparison between the cyclic peptide 116 and the cyclic peptide 131, the cyclic peptide, where the amino acid residue in which the carbon atom of the main chain and the sulfur atom on the side chain are separated by 2 to 10 carbon atoms is one of amino acid residues involved in the intramolecular crosslinking, tends to exhibit an improved integrin binding property as compared with the case where the amino acid residue such as a penicillamine residue, in which the carbon atom in the main chain and the sulfur atom on the side chain are separated by one carbon atom is one of amino acid residues involved in the intramolecular crosslinking Next, a cell scaffold material was prepared using the obtained peptide, and an iPS cell culture experiment was carried out.

(Surface Treatment of Polystyrene Plate)

Using a plasma treating device (SCB-106 manufactured by SAKIGAKE-Semiconductor Co., Ltd.), a 6-well plate (manufactured by Corning Incorporated) made of polystyrene was subjected to surface treatment in an ammonia gas under the conditions of a gas pressure of 10 Pa, an output of 700 W, and a treatment time of 5 minutes.

(Preparation of CMD Coating Well)

9.5 g of distilled water was added to 0.5 g of sodium carboxymethyl dextran (manufactured by Meito Sangyo Co., Ltd., trade name: "CMD", molecular weight: 1 million, hereinafter may be also referred to as "CMD") and stirred so that CMD was sufficiently dissolved, whereby a 5% by weight CMD solution was prepared.

Next, 1 mL of distilled water was added to 383.4 mg of 1-ethyl-3-(3-dimethylaminopropyl)carbodiimide hydrochloride (manufactured by Nacalai Tesque, Inc., hereinafter may be also referred to as "EDC") to prepare an EDC solution. Next, 1 mL of distilled water was added to 57.5 mg of N-hydroxysuccinimide (manufactured by FUJIFILM Wako Pure Chemical Corporation, hereinafter may be also referred to as "NHS") to prepare an NHS solution.

Next, 0.05 mL of the EDC solution and 0.05 mL of the NHS solution were added to 10 g of the CMD solution prepared above and stirred, and 1 mL of the obtained CMD-containing coating solution was immediately added dropwise to one of wells of the polystyrene plate subjected to surface treatment as described above. After allowing the polystyrene plate to stand at room temperature for 1 hour, the well was sufficiently washed with distilled water to remove the CMD-containing coating solution, whereby a CMD coating well was obtained.

(Preparation of Ligand Coating Well)

1 mL of an HBS-N buffer (manufactured by GE Healthcare Japan Corporation) was added to 0.2 mg of the cyclic peptide 92 to prepare a cyclic peptide solution. Next, 1 mL of distilled water was added to 76.7 mg of EDC to prepare an EDC solution. Next, 1 mL of distilled water was added to 11.5 mg of NHS to prepare an NHS solution. Next, 1 mL of distilled water was added to 1 mL of ethanolamine (manufactured by Bio-Rad Laboratories, Inc., trade name: "ProteOn ethanolamine HCL") to prepare an ethanolamine solution.

Next, 0.5 mL of the NHS solution was added to 0.5 mL of the EDC solution prepared as described above and stirred, and 1 mL of the obtained mixed solution was immediately added dropwise to the CMD coating well. After allowing the polystyrene plate to stand for 7 minutes, the well was sufficiently washed with distilled water to remove the mixed solution from the well. Further, 1 mL of the above cyclic peptide solution was added dropwise to the well, and the well was allowed to stand for 25 minutes and then washed sufficiently with distilled water to remove the cyclic peptide solution. Further, 1 mL of the ethanolamine solution was added dropwise to the well, and after allowing to stand for 7 minutes, the well was sufficiently washed with distilled water to remove the ethanolamine solution to obtain a well (hereinafter referred to as a "ligand coating well") having a cell scaffold material, on which the cyclic peptide 92 was immobilized on CMD as a base material.

(γ Ray Sterilization Treatment)

The ligand coating well prepared as described above was sealed in a sterilization bag and subjected to γ ray sterilization treatment in an irradiation facility No. 1 manufactured by RADIA INDUSTRY Co., Ltd. under the condition of a dose of 25 kGy. As a result of the above, a γ ray irradiated cell scaffold material (hereinafter, referred to as an "irradiated cell scaffold material A") was obtained.

(Evaluation of iPS Cell Culture Performance of Peptide)

As the iPS cell, a 01434 clone established by Fujifilm Cellular Dynamics, Inc. was used. The iPS cell was seeded in a culture polystyrene plate having the irradiated cell scaffold material A on the surface at a split rate=1:6, cultured for three days in a feeder-free ES and iPS cell culture medium (Stem Cell Technologies, product name: mTeSR1), and then the iPS cells were stripped to single cells and collected by treatment with a cell dissociation reagent (manufactured by Thermo Fisher Scientific, Inc., product name: TrypLE Select). From the obtained cell suspension, the number of cells was measured using a cell viability autoanalyzer (manufactured by Beckman Coulter Inc., product name: Vi-Cell XR) and used to determine whether or not the ceFlls had proliferated. The obtained results were evaluated according to the following criteria. The evaluation results are shown in Table 14. In Table 14, Hcy represents a homocysteine residue, Dab(acetyl) represents a 2-amino-4-acetylamino-butanoic acid residue, and Dap(acetyl) represents a 2-amino-3-acetylamino-propanoic acid residue.

| Evaluation standards for iPS cell culture performance |
|---|
| A: Proliferation of iPS cells was observed. |
| B: No proliferation of iPS cells was observed. |

TABLE 14

| | Cyclic peptide | Amino acid sequence (N terminal -> C terminal) | Crosslinking moiety amino acid residue | | Evaluation result of culture performance |
|---|---|---|---|---|---|
| Example | Cyclic peptide 92 | KKKA-(Hcy)-IPRGDSFA(Dab(acetyl))A (SEQ ID NO: 93) | Hcy | Dab | A |
| Comparative Example | Cyclic peptide 167 | KKK(Dap(acetyl))EPRGDNYRC (SEQ ID NO: 168) | Dap | C | B |

From the results shown in Table 14, it can be seen that in a case where a cell scaffold material containing the cyclic peptide 92 corresponding to the cyclic peptide according to the present disclosure is used, iPS cells proliferate, whereas in a case where a cell scaffold material containing the cyclic peptide of the cyclic peptide 167 (Comparative Example) is used, cyclic, iPS cells do not proliferate. This shows that the cell scaffold material containing the cyclic peptide according to the present disclosure is more stable against γ rays and the like than the cell scaffold material containing the cyclic peptide of Comparative Example, and has good cell proliferation performance even in a case where sterilization treatment with γ rays or the like is carried out.

The disclosure of JP2019-108962 filed on Jun. 11, 2019, is incorporated in the present specification by reference in its entirety.

All documents, patent applications, and technical standards described in the present specification are incorporated herein by reference, to the same extent as in the case where each of the documents, patent applications, and technical standards is specifically and individually described.

SEQUENCE LISTING

International application based on the International Patent Cooperation Treaty 19F00785W1JP20022558_25. app

What is claimed is:

1. A cyclic peptide comprising:

a cyclic segment comprising an RGD sequence and having 8 to 14 amino acid residues, a thioether bond being formed between an amino acid residue $X^a$ located on a most N-terminal side of the cyclic segment and an amino acid residue $X^b$ located on a most C-terminal side of the cyclic segment, wherein one of the amino acid residue $X^a$ and the amino acid residue $X^b$ is a 2-amino-4-acetylamino-butanoic acid residue, an N-δ-acetyl-ornithine residue, or an N-ε-acetyl-lysine residue, and the other one of the amino acid residue $X^a$ and the amino acid residue $X^b$ is an L-homocysteine residue or a D-homocysteine residue, wherein the α carbon of the 2-amino-4-acetylamino-butanoic acid residue, the N-δ-acetyl-ornithine residue, or the N-ε-acetyl-lysine residue is separated from the sulfur atom of the L-homocysteine residue or the D-homocysteine residue by five or more atoms, and wherein the cyclic segment comprises an amino acid sequence having 80% or more sequence identity to the amino acid sequence IPRGDNFR (SEQ ID NO: 1), IPRGDSFA (SEQ ID NO: 170), VPRGDTFA (SEQ ID NO: 171), or TPRGDTFA (SEQ ID NO: 172).

2. The cyclic peptide according to claim 1, further comprising at least one of a first segment between the cyclic segment and an N-terminal of the cyclic peptide or a second segment between the cyclic segment and a C-terminal of the cyclic peptide, wherein the at least one of the first segment or the second segment comprises an amino acid residue having an immobilizing functional group in a side chain.

3. The cyclic peptide according to claim 2, wherein the immobilizing functional group is an amino group or a thiol group.

4. The cyclic peptide according to claim 2, wherein the amino acid residue having the immobilizing functional group in a side chain is selected from the group consisting of an L-lysine residue, a D-lysine residue, an L-cysteine residue, a D-cysteine residue, an L-homocysteine residue, and a D-homocysteine residue.

5. The cyclic peptide according to claim 4, wherein the amino acid residue having the immobilizing functional group in a side chain is selected from the group consisting of an L-lysine residue, a D-lysine residue, an L-cysteine residue, and a D-cysteine residue.

6. The cyclic peptide according to claim 2, wherein, in a case of being present, each of the first segment and the second segment has a length of 1 to 20 amino acid residues.

7. The cyclic peptide according to claim 1, wherein the cyclic peptide comprises a plurality of the cyclic segments, and amino acid sequences of the respective cyclic segments may be the same or different from each other.

8. The cyclic peptide according to claim 7, wherein the plurality of the cyclic segments are connected to each other by a connecting moiety having a length of 1 to 20 amino acid residues.

9. The cyclic peptide according to claim 1, wherein a total number of amino acid residues is 8 to 50.

10. The cyclic peptide according to claim 1, wherein the cyclic peptide is represented by Formula II':

$$R^N-X^8_{v0}-X^6_{t0}-X^9_{p0}-X^a-X^t_{v5}-X^1-X^2-R-D-G-X^3-X^4-X^5_{v6}-X^t_{v7}-X^b-X^{10}_{q0}-X^7_{u0}-X^{11}_{w0}-R^c \quad (II')$$

wherein in Formula II', $X^a$ represents the amino acid residue $X^a$, $X^b$ represents the amino acid residue $X^b$;

$X^8$, $X^9$, $X^{10}$ and $X^{11}$ each independently represent any amino acid residue, where in a case where a plurality of $X^8$'s, $X^9$'s, $X^{10}$'s or $X^{11}$'s are present, the plurality of $X^8$'s, $X^9$'s, $X^{10}$'s or $X^{11}$'s may be the same or different from each other;

$R^N$ represents an N-terminal group; $R^C$ represents a C-terminal group;

$X^6$ and $X^7$ each independently represent an amino acid residue having an immobilizing functional group in a side chain, where in a case where a plurality of $X^6$'s or $X^7$'s are present, the plurality of $X^6$'s or $X^7$'s may be the same or different from each other;

p0 and q0 are integers and respectively satisfy $0 \le p0 \le 15$ and $0 \le q0 \le 15$;

t0 and u0 are integers and respectively satisfy $0 \le t0 \le 5$ and $0 \le u0 \le 5$;

v0 and w0 are integers and respectively satisfy $0 \le v0 \le 5$ and $0 \le w0 \le 5$; and p0, q0, t0, u0, v0, and w0 further satisfy $0 \le p0+q0+t0+u0+v0+w0 \le 39$;

$X^t$ represents any amino acid residue, and in a case a plurality of X's are present, the plurality of X's may be the same or different from each other;

$X^1$ represents I, V, D, E, Y, L, T, or homotyrosine;

$X^2$ represents P, T, or S;

$X^3$ represents N, S, T, V, A or homoserine;

$X^4$ represents F, Y, or P;

$X^5$ represents R, D, E, A, T, S, or G;

v5 and v7 each independently represent an integer of 0 to 6; and v6 represents 0 or 1.

11. The cyclic peptide according to claim 10, wherein the cyclic peptide satisfies at least one selected from the group consisting of the following (i) to (v):

(i) an amino acid residue represented by $X^1$ is I, V, or T;

(ii) an amino acid residue represented by $X^2$ is P;

(iii) an amino acid residue represented by $X^3$ is S or T;

(iv) an amino acid residue represented by $X^4$ is F; and (v) v6 represents 1, and an amino acid residue represented by $X^5$ is A.

12. A cell scaffold material comprising:

a base material; and the cyclic peptide according to claim 1.

13. A cell separating material comprising:

a holding material; and the cyclic peptide according to claim 1.

14. A medium comprising:

a culture component; and the cyclic peptide according to claim 1.

* * * * *